US006730506B2

(12) United States Patent
Yan et al.

(10) Patent No.: US 6,730,506 B2

(45) Date of Patent: May 4, 2004

(54) ISOLATED HUMAN KINASE PROTEINS

(75) Inventors: Chunhua Yan, Boyds, MD (US); Karen A. Ketchum, Germantown, MD (US); Valentina Di Francesco, Rockville, MD (US); Ellen M. Beasley, Darnestown, MD (US)

(73) Assignee: Applera Genomics, Norwalk, CT (US)

( * ) Notice: Subject to any disclaimer, the term of this patent is extended or adjusted under 35 U.S.C. 154(b) by 20 days.

(21) Appl. No.: 10/224,562

(22) Filed: Aug. 21, 2002

(65) Prior Publication Data

US 2003/0022229 A1 Jan. 30, 2003

Related U.S. Application Data

(62) Division of application No. 09/801,861, filed on Mar. 9, 2001, now Pat. No. 6,492,154.

(60) Provisional application No. 60/265,151, filed on Jan. 31, 2001.

(51) Int. Cl.[7] .......................... C07K 1/00; C12Q 1/68; C12N 5/00; C12N 15/00; C12N 9/12

(52) U.S. Cl. .......................... 435/194; 530/350; 435/6; 435/252.3; 435/320.1; 435/325

(58) Field of Search .......................... 435/194, 252.3, 435/6, 320.1, 325; 530/350

(56) References Cited

FOREIGN PATENT DOCUMENTS

WO WO 99/33962 A 7/1999

OTHER PUBLICATIONS

Database Swissprot Online? EBI, Hinxton, Cambridgeshire, UK; (Dec. 1, 2001) Hadano et al: "ALSCR7 Ser_thr_pkinase." Database Accession No. Q96Q40: XP002216746.

Database EBI Online? EBI, Hinxton, Cambridgeshire, UK (Dec. 7, 2000) Plowman et al: "Sequence 47 from Patent WO 00/73469 (Protein Kinases)" Database Accession No. AX056403; XP002216747.

Database EPOP Online? EBI, Hinxton, Cambridgeshire, UK (Dec. 7, 2000) Plowman et al: "Sequence 165 from Patent WO 00/73469 (Protein Kinases)" Database Accession No. AX056521; XP002216748.

Database EMBL Online? EBI, Hinxton, Cambridgeshire, UK: (Apr. 9, 1999) Sulston and Waterson: "*Homo sapiens* BAC close RP11–182H9 from 2, complete sequence." Database Accession No. AC007242; XP002216749.

Johnston, M: "Gene chips: Array of hope for understanding gene regulation" Current Biology, vol. 8, No. 5 (Feb. 1998), pp. R171–R174 (XP000905195).

Hanks, S.K. et al: "Use of Degenerate Oligonucleotide Probes to Identify Clones That Encode Protein Kinases" Methods in Enzymology, Academic Press Inc., vol. 200 (1991), pp. 525–532 (XP001096015).

Hanks, S.K.: "Homology probing: Identification of cDNA clones encoding members of the protein–serine kinase family" Proceedings of the National Academy of Sciences of USA, National Academy of Science, vol. 84 (Jan. 1987), pp. 388–392.

Lazzaro, M.A., et al: "A Novel ede2 Related Protein Kinase Expressed in the Nervous System" Journal of Neurochemistry, vol. 69, No. 1 (1997), pp. 348–364 (XP002103363).

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 46 Drawing Sheets

SPLICE FORM 1 (cDNA sequence):

```
   1 GTGAGTCATA TGAAAGCTCC ACGCTGCTGA CCTCTGGCAA AAAGGGAGAG
  51 AACAAGGATA GGAGAGGCAG TGGGGGAAAG GTTCAAGTGC GGGTTTTCTC
 101 CTTGAACCTA GAAGATTATG GGTCAAGAGC TGTGTGCAAA GACTGTACAG
 151 CCTGGATGCA GCTGCTACCA TTGTTCAGAG GGAGGCGAGG CACACAGCTG
 201 TCGGAGGAGT CAGCCTGAGA CCACGGAGGC TGCGTTCAAG CTAACAGACC
 251 TAAAAGAAGC ATCATGTTCC ATGACTTCAT TTCACCCCAG GGGACTTCAA
 301 GCTGCCCGTG CCCAGAAGTT CAAGAGTAAA AGGCCACGGA GTAACAGTGA
 351 TTGTTTTCAG GAAGAGGATC TGAGGCAGGG TTTTCAGTGG AGGAAGAGCC
 401 TCCCTTTTGG GGCAGCCTCA TCTTACTTGA ACTTGGAGAA GCTGGGTGAA
 451 GGCTCTTATG CGACAGTTTA CAAGGGGATT AGCAGAATAA ATGGACAACT
 501 AGTGGCTTTA AAAGTCATCA GCATGAATGC AGAGGAAGGA GTCCCATTTA
 551 CAGCTATCCG AGAAGCTTCT CTCCTGAAGG GTTTGAAACA TGCCAATATT
 601 GTGCTCCTGC ATGACATAAT CCACACCAAA GAGACACTGA CATTCGTTTT
 651 TGAATACATG CACACAGACC TGGCCCAGTA TATGTCTCAG CATCCAGGAG
 701 GGCTTCATCC TCATAATGTC AGACTTTTCA TGTTTCAACT TTTGCGGGGC
 751 CTGGCGTACA TCCACCACCA ACACGTTCTT CACAGGGACC TGAAACCTCA
 801 GAACTTACTC ATCAGTCACC TGGGAGAGCT CAAACTGGCT GATTTTGGTC
 851 TTGCCCGGGC CAAGTCCATT CCCAGCCAGA CATACTCTTC AGAAGTCGTG
 901 ACCCTCTGGT ACCGGCCCCC TGATGCTTTG CTGGGAGCCA CTGAATATTC
 951 CTCTGAGCTG GACATATGGG GTGCAGGCTG CATCTTTATT GAAATGTTCC
1001 AGGGTCAACC TTTGTTTCCT GGGGTTTCCA ACATCCTTGA ACAGCTGGAG
1051 AAAATCTGGG AGGTGCTGGG AGTCCCTACA GAGGATACTT GGCCGGGAGT
1101 CTCCAAGCTA CCTAACTACA ATCCAGGTAA TATTGATCTG AGCTTTTGAA
1151 TACTCTGAGA ATTAGTAATG TAAGGAGAGC ATTGGCCACG CTAACAGGGC
1201 GTTCTTGTAT TGTGAACTCA GCGGCAAAGA TGGGTGTAGA GGAATTTCTA
1251 CATTCATATA TTCCCTGACT AATCTTTGTA TGAGGAAGAC ACTGAAAGAG
1301 TAGCTGAGGT TAGACCAGTT CCCCAGCTCT GTAAAACACA AGTAGCAAGC
1351 TGAATAGAAT TTGAAATGAC TATTACTGTG GATTCCACAT CCATTGTCAA
1401 ATACCCAATG GCTCAAAAGA ACAACTCAAA AGATGGGCTC ACTTTTGGGC
1451 CCCCTGACTG TCATAAGTGT ATTGATTAGT ATTGAATTGC ATATGTATAA
1501 AAAGAAAGCT AATGCAACAG AACAGAGGTA GAGGCTCGCT AGGCCTAGGA
1551 CATGCCAAGT AAGCTGTCTG TAGGTTATAC TTACTAAGAG TTCATTCATT
1601 GCCTGTAAAC CTGACACTTG GTCATTGTCT CTCACACATT TCATCTTTCA
1651 AGACTGGCTT CTGGGATCGA TTTAGAAGTG CTGGAAGTGT TATCCATGGG
1701 GGAATTCTTT GAGAAGCTGT CGCAGGGCCA CATCAGAGGG ATCAGATTAA
1751 GCAGTAGTCA CTTCAAGGAT GTTGAGACAG AGGGGAGGAG ACAGGCACTG
1801 AACTACAGGA TGAAGGATCA TATTAGAAGC TGAAGAAGCA AATAAAGCCC
1851 ATGCCAAAGC TGAGCTCTCA CTGGCAGGGT TGAAGGGGAG GTAGAAAGGT
1901 ACAGATAACG ACAAGATTAG GGTGGATATG CTCCAAGCCA GATTTTTCTA
1951 GTCTTTATGG TCTTACATTG TTCCATTACT AAAAATGAAA TCTTCCCAAA
2001 TTGTTGTCCT TACTTTTTTT TTTTTTTTTT GAGATGGAGT TTTGCTCTTA
2051 TCGCCCAGGC TGGAGTGCAG TGAGCCGAGA TTGCGCCACT GCATGTCCGC
2101 AGTCCGACCT GGGCGACAGA GCGAGACTCC GTCTCAAAAC TAAAAAAAAA
2151 AAAAAAAAAA AAAAAAAAAA AAAAAAAAAA AAAAAAAAAA AAAAAAAAAA
2201 AAA   (SEQ ID NO:1)
```

FEATURES:

```
5'UTR:        1-117
Start Codon:  118
Stop Codon:   1147
3'UTR:        1150
```

SPLICE FORM 2 (transcript sequence):

```
   1 ATGGGTCAAG AGCTGTGTGC AAAGACTGTA CAGCCTGGAT GCAGCTGCTA
```

FIGURE 1A

```
  51 CCATTGTTCA GAGGGAGGCG AGGCACACAG CTGTCGGAGG AGTCAGCCTG
 101 AGACCACGGA GGCTGCGTTC AAGCTAACAG ACCTAAAAGA AGCATCATGT
 151 TCCATGACTT CATTTCACCC CAGGGGACTT CAAGCTGCCC GTGCCCAGAA
 201 GTTCAAGAGT AAAAGGCCAC GGAGTAACAG TGATTGTTTT CAGGAAGAGG
 251 ATCTGAGGCA GGGTTTTCAG TGGAGGAAGA GCCTCCCTTT TGGGGCAGCC
 301 TCATCTTACT TGAACTTGGA GAAGCTGGGT GAAGGCTCTT ATGCGACAGT
 351 TTACAAGGGG ATTAGCAGAA TAAATGGACA ACTAGTGGCT TTAAAAGTCA
 401 TCAGCATGAA TGCAGAGGAA GGAGTCCCAT TTACAGCTAT CCGAGAAGCT
 451 TCTCTCCTGA AGGGTTTGAA ACATGCCAAT ATTGTGCTCC TGCATGACAT
 501 AATCCACACC AAAGAGACAC TGACATTCGT TTTTGAATAC ATGCACACAG
 551 ACCTGGCCCA GTATATGTCT CAGCATCCAG GAGGGCTTCA TCCTCATAAT
 601 GTCAGACTTT TCATGTTTCA ACTTTTGCGG GGCCTGGCGT ACATCCACCA
 651 CCAACACGTT CTTCACAGGG ACCTGAAACC TCAGAACTTA CTCATCAGTC
 701 ACCTGGGAGA GCTCAAACTG GCTGATTTTG GTCTTGCCCG GGCCAAGTCC
 751 ATTCCCAGCC AGACATACTC TTCAGAAGTC GTGACCCTCT GGTACCGGCC
 801 CCCTGATGCT TTGCTGGGAG CCACTGAATA TTCCTCTGAG CTGGACATAT
 851 GGGGTGCAGG CTGCATCTTT ATTGAAATGT TCCAGGGTCA ACCTTTGTTT
 901 CCTGGGGTTT CCAACATCCT TGAACAGCTG GAGAAAATCT GGGAGGTGCT
 951 GGGAGTCCCT ACAGAGGATA CTTGGCCGGG AGTCTCCAAG CTACCTAACT
1001 ACAATCCAGA ATGGTTCCCA CTGCCTACGC CTCGAAGCCT TCATGTTGTC
1051 TGGAACAGGC TGGGCAGGGT TCCTGAAGCT GAAGACCTGG CCTCCCAGAT
1101 GCTAAAAGGC TTTCCCAGAG ACCGCGTCTC CGCCCAGGAA GCACTTGTTC
1151 ATGATTATTT CAGCGCCCTG CCATCTCAGC TGTACCAGCT TCCTGATGAG
1201 GAGTCTTTGT TTACAGTTTC AGGAGTGAGG CTAAAGCCAG AAATGTGTGA
1251 CCTTTTGGCC TCCTACCAGA AAGGTCACCA CCCAGCCCAG TTTAGCAAAT
1301 GCTGGTGA  (SEQ ID NO:4)
```

FEATURES:
Start Codon: 1
Stop Codon: 1306

Homologous proteins:
Top 10 BLAST Hits

| | Score | E |
|---|---|---|
| **SPLICE FORM 1:** | | |
| CRA\|18000005115058 /altid=gi\|6755044 /def=ref\|NP_035204.1\| PFTA... | 391 | e-107 |
| CRA\|18000005205923 /altid=gi\|6912584 /def=ref\|NP_036527.1\| PFTA... | 390 | e-107 |
| CRA\|18000005100533 /altid=gi\|2392814 /def=gb\|AAB70455.1\| (U6239... | 389 | e-107 |
| CRA\|151000011260745 /altid=gi\|12002201 /def=gb\|AAG43234.1\| (AF1... | 386 | e-106 |
| CRA\|1000682315356 /altid=gi\|5579351 /def=gb\|AAD45514.1\| (AF1524... | 367 | e-100 |
| CRA\|89000000195020 /altid=gi\|7292375 /def=gb\|AAF47781.1\| (AE003... | 367 | e-100 |
| CRA\|1000682315355 /altid=gi\|5579349 /def=gb\|AAD45513.1\| (AF1524... | 367 | e-100 |
| CRA\|1000682315353 /altid=gi\|5579343 /def=gb\|AAD45510.1\| (AF1523... | 367 | e-100 |
| CRA\|1000682315354 /altid=gi\|5579347 /def=gb\|AAD45512.1\| (AF1524... | 367 | e-100 |
| CRA\|1000682315352 /altid=gi\|5579341 /def=gb\|AAD45509.1\| (AF1523... | 367 | e-100 |
| **SPLICE FORM 2:** | | |
| CRA\|18000005115058 /altid=gi\|6755044 /def=ref\|NP_035204.1\| PFTA... | 469 | e-131 |
| CRA\|18000005205923 /altid=gi\|6912584 /def=ref\|NP_036527.1\| PFTA... | 468 | e-131 |
| CRA\|18000005100533 /altid=gi\|2392814 /def=gb\|AAB70455.1\| (U6239... | 467 | e-131 |
| CRA\|151000011260745 /altid=gi\|12002201 /def=gb\|AAG43234.1\| (AF1... | 465 | e-130 |
| CRA\|1000682315356 /altid=gi\|5579351 /def=gb\|AAD45514.1\| (AF1524... | 422 | e-117 |
| CRA\|1000682315355 /altid=gi\|5579349 /def=gb\|AAD45513.1\| (AF1524... | 422 | e-117 |
| CRA\|1000682315354 /altid=gi\|5579347 /def=gb\|AAD45512.1\| (AF1524... | 422 | e-117 |
| CRA\|1000682315353 /altid=gi\|5579343 /def=gb\|AAD45510.1\| (AF1523... | 422 | e-117 |
| CRA\|1000682315352 /altid=gi\|5579341 /def=gb\|AAD45509.1\| (AF1523... | 422 | e-117 |
| CRA\|18000005045994 /altid=gi\|1524004 /def=emb\|CAA67862.1\| (X995... | 421 | e-116 |

FIGURE 1B

BLAST dbEST hits:

| Score | | E |
|---|---|---|
| **SPLICE FORM 1:** | | |
| gi\|9806331 /dataset=dbest /taxon=960... | 1334 | 0.0 |
| gi\|2140968 /dataset=dbest /taxon=9606 ... | 575 | e-162 |
| gi\|2028058 /dataset=dbest /taxon=9606 ... | 377 | e-102 |
| gi\|13132599 /dataset=dbest /taxon=960... | 319 | 8e-85 |

FIGURE 1C

SPLICE FORM 2:

| | | |
|---|---|---|
| gi\|9806331 /dataset=dbest /taxon=960... | 1334 | 0.0 |
| gi\|2140968 /dataset=dbest /taxon=9606 ... | 954 | 0.0 |
| gi\|2028058 /dataset=dbest /taxon=9606 ... | 377 | e-102 |
| gi\|2140870 /dataset=dbest /taxon=9606 ... | 283 | 5e-74 |

EXPRESSION INFORMATION FOR MODULATORY USE:
SPLICE FORM 1:
library source (from BLAST dbEST hits):
gi|9806331 Uterus-endometrium adenocarcinoma cell line
gi|2140968 testis
gi|2028058 Lung fibroblast cell line
gi|13132599 Kidney renal cell adenocarcinoma Tissue Expression:
Whole brain SPLICE FORM 2:
library source (from BLAST dbEST hits):
gi|9806331 Uterus endometrium adenocarcinoma line
gi|2140968 Testis
gi|2028058 Lung fibroblast
gi|2140870 Testis

FIGURE 1D

```
SPLICE FORM 1:
    1 MGQELCAKTV QPGCSCYHCS EGGEAHSCRR SQPETTEAAF KLTDLKEASC
   51 SMTSFHPRGL QAARAQKFKS KRPRSNSDCF QEEDLRQGFQ WRKSLPFGAA
  101 SSYLNLEKLG EGSYATVYKG ISRINGQLVA LKVISMNAEE GVPFTAIREA
  151 SLLKGLKHAN IVLLHDIIHT KETLTFVFEY MHTDLAQYMS QHPGGLHPHN
  201 VRLFMFQLLR GLAYIHHQHV LHRDLKPQNL LISHLGELKL ADFGLARAKS
  251 IPSQTYSSEV VTLWYRPPDA LLGATEYSSE LDIWGAGCIF IEMFQGQPLF
  301 PGVSNILEQL EKIWEVLGVP TEDTWPGVSK LPNYNPGNID LSF  (SEQ ID
NO:2)

SPLICE FORM 2:
    1 MGQELCAKTV QPGCSCYHCS EGGEAHSCRR SQPETTEAAF KLTDLKEASC
   51 SMTSFHPRGL QAARAQKFKS KRPRSNSDCF QEEDLRQGFQ WRKSLPFGAA
  101 SSYLNLEKLG EGSYATVYKG ISRINGQLVA LKVISMNAEE GVPFTAIREA
  151 SLLKGLKHAN IVLLHDIIHT KETLTFVFEY MHTDLAQYMS QHPGGLHPHN
  201 VRLFMFQLLR GLAYIHHQHV LHRDLKPQNL LISHLGELKL ADFGLARAKS
  251 IPSQTYSSEV VTLWYRPPDA LLGATEYSSE LDIWGAGCIF IEMFQGQPLF
  301 PGVSNILEQL EKIWEVLGVP TEDTWPGVSK LPNYNPEWFP LPTPRSLHVV
  351 WNRLGRVPEA EDLASQMLKG FPRDRVSAQE ALVHDYFSAL PSQLYQLPDE
  401 ESLFTVSGVR LKPEMCDLLA SYQKGHHPAQ FSKCW  (SEQ ID NO:5)

FEATURES:
Functional domains and key regions:
SPLICE FORM 1:
[1] PDOC00005 PS00005 PKC_PHOSPHO_SITE
Protein kinase C phosphorylation site

Number of matches: 2
      1       27-29 SCR
      2       70-72 SKR

[2] PDOC00006 PS00006 CK2_PHOSPHO_SITE
Casein kinase II phosphorylation site

Number of matches: 3
      1       31-34 SQPE
      2       75-78 SNSD
      3     279-282 SELD

[3] PDOC00007 PS00007 TYR_PHOSPHO_SITE
Tyrosine kinase phosphorylation site

            108-114 KLGEGSY

[4] PDOC00008 PS00008 MYRISTYL
N-myristoylation site

Number of matches: 8
      1         2-7 GQELCA
      2       59-64 GLQAAR
      3      98-103 GAASSY
      4     112-117 GSYATV
      5     126-131 GQLVAL
      6     141-146 GVPFTA
      7     155-160 GLKHAN
```

FIGURE 2A 8 244-249 GLARAK

[5] PDOC00100 PS00107 PROTEIN_KINASE_ATP
Protein kinases ATP-binding region signature 109-132 LGEGSYATVYKGISRINGQLVALK

FIGURE 2B

[6] PDOC00100 PS00108 PROTEIN_KINASE_ST
Serine/Threonine protein kinases active-site signature 220-232 VLHRDLKPQNLLI

[7] PDOC00170 PS00191 CYTOCHROME_B5_1
Cytochrome b5 family, heme-binding domain signature 188-195 YMSQHPGG SPLICE FORM 2:
[1] PDOC00005 PS00005 PKC_PHOSPHO_SITE
Protein kinase C phosphorylation site Number of matches: 3

| | | |
|---|---|---|
| 1 | 27-29 | SCR |
| 2 | 70-72 | SKR |
| 3 | 343-345 | TPR |

[2] PDOC00006 PS00006 CK2_PHOSPHO_SITE
Casein kinase II phosphorylation site

Number of matches: 4

| | | |
|---|---|---|
| 1 | 31-34 | SQPE |
| 2 | 75-78 | SNSD |
| 3 | 279-282 | SELD |
| 4 | 377-380 | SAQE |

[3] PDOC00007 PS00007 TYR_PHOSPHO_SITE
Tyrosine kinase phosphorylation site 108-114 KLGEGSY

[4] PDOC00008 PS00008 MYRISTYL
N-myristoylation site

Number of matches: 8

| | | |
|---|---|---|
| 1 | 2-7 | GQELCA |
| 2 | 59-64 | GLQAAR |
| 3 | 98-103 | GAASSY |
| 4 | 112-117 | GSYATV |
| 5 | 126-131 | GQLVAL |
| 6 | 141-146 | GVPFTA |
| 7 | 155-160 | GLKHAN |
| 8 | 244-249 | GLARAK |

[5] PDOC00100 PS00107 PROTEIN_KINASE_ATP
Protein kinases ATP-binding region signature 109-132 LGEGSYATVYKGISRINGQLVALK

[6] PDOC00100 PS00108 PROTEIN_KINASE_ST
Serine/Threonine protein kinases active-site signature

FIGURE 2C 220-232 VLHRDLKPQNLLI

FIGURE 2D

[7] PDOC00170 PS00191 CYTOCHROME_B5_1
Cytochrome b5 family, heme-binding domain signature 188-195 YMSQHPGG <u>Membrane spanning structure and domains:</u>
(SPLICE FORMS 1 & 2)

| Helix | Begin | End | Score | Certainty |
|---|---|---|---|---|
| 1 | 283 | 303 | 0.776 | Putative |

FIGURE 2E

```
BLAST Alignment to Top Hit:
SPLICE FORM 1:
>CRA|18000005115058 /altid=gi|6755044 /def=ref|NP_035204.1|
PFTAIRE
            protein kinase 1 [Mus musculus] /org=Mus musculus
            /taxon=10090 /dataset=nraa /length=469
          Length = 469

 Score =  391 bits (993), Expect = e-107
 Identities = 184/240 (76%), Positives = 208/240 (86%)
 Frame = +1

Query: 406 FGAASSYLNLEKLGEGSYATVYKGISRINGQLVALKVISMNAEEGVPFTAIREASLLKGL 585
            FG A SY  LEKLGEGSYATVYKG S++NG+LVALKVI +  EEG PFTAIREASLLKGL
Sbjct: 129 FGKADSYEKLEKLGEGSYATVYKGKSKVNGKLVALKVIRLQEEEGTPFTAIREASLLKGL 188

Query: 586 KHANIVLLHDIIHTKETLTFVFEYMHTDLAQYMSQHPGGLHPHNVRLFMFQLLRGLAYIH 765
            KHANIVLLHDIIHTKETLT VFEY+HTDL QYM QHPGGLHP NV+LF+FQLLRGL+YIH
Sbjct: 189 KHANIVLLHDIIHTKETLTLVFEYVHTDLCQYMEQHPGGLHPDNVKLFLFQLLRGLSYIH 248

Query: 766 HQHVLHRDLKPQNLLISHLGELKLADFGLARAKSIPSQTYSSEVVTLWYRPPDALLGATE 945
             +++LHRDLKPQNLLIS  GELKLADFGLARAKS+PS TYS+EVVTLWYRPPD LLG+TE
Sbjct: 249 QRYILHRDLKPQNLLISDTGELKLADFGLARAKSVPSHTYSNEVVTLWYRPPDVLLGSTE 308

Query: 946 YSSELDIWGAGCIFIEMFQGQPLFPGVSNILEQLEKIWEVLGVPTEDTWPGVSKLPNYNP 1125
            YS+ LD+WG GCIF+EM QG  FPG+ +I +QLE+I+ VLG P EDTWPGV  LP++ P
Sbjct: 309 YSTCLDMWGVGCIFVEMIQGVAAFPGMKDIQDQLERIFLVLGTPNEDTWPGVHSLPHFKP 368
(SEQ ID NO:6)

>CRA|18000005205923 /altid=gi|6912584 /def=ref|NP_036527.1|
PFTAIRE
            protein kinase 1 [Homo sapiens] /org=Homo sapiens
            /taxon=9606 /dataset=nraa /length=451
          Length = 451

 Score =  390 bits (990), Expect = e-107
 Identities = 184/245 (75%), Positives = 209/245 (85%)
 Frame = +1

Query: 406 FGAASSYLNLEKLGEGSYATVYKGISRINGQLVALKVISMNAEEGVPFTAIREASLLKGL 585
            FG A SY  LEKLGEGSYATVYKG S++NG+LVALKVI +  EEG PFTAIREASLLKGL
Sbjct: 111 FGKADSYEKLEKLGEGSYATVYKGKSKVNGKLVALKVIRLQEEEGTPFTAIREASLLKGL 170

Query: 586 KHANIVLLHDIIHTKETLTFVFEYMHTDLAQYMSQHPGGLHPHNVRLFMFQLLRGLAYIH 765
            KHANIVLLHDIIHTKETLT VFEY+HTDL QYM +HPGGLHP NV+LF+FQLLRGL+YIH
Sbjct: 171 KHANIVLLHDIIHTKETLTLVFEYVHTDLCQYMDKHPGGLHPDNVKLFLFQLLRGLSYIH 230

Query: 766 HQHVLHRDLKPQNLLISHLGELKLADFGLARAKSIPSQTYSSEVVTLWYRPPDALLGATE 945
             +++LHRDLKPQNLLIS  GELKLADFGLARAKS+PS TYS+EVVTLWYRPPD LLG+TE
Sbjct: 231 QRYILHRDLKPQNLLISDTGELKLADFGLARAKSVPSHTYSNEVVTLWYRPPDVLLGSTE 290

Query: 946 YSSELDIWGAGCIFIEMFQGQPLFPGVSNILEQLEKIWEVLGVPTEDTWPGVSKLPNYNP 1125
            YS+ LD+WG GCIF+EM QG  FPG+ +I +QLE+I+ VLG P EDTWPGV  LP++ P
Sbjct: 291 YSTCLDMWGVGCIFVEMIQGVAAFPGMKDIQDQLERIFLVLGTPNEDTWPGVHSLPHFKP 350

Query: 1126 GNIDL 1140L
Sbjct: 351  ERFTL 355  (SEQ ID NO:7)
```

FIGURE 2F

```
SPLICE FORM 2:
>CRA|18000005115058 /altid=gi|6755044 /def=ref|NP_035204.1|
PFTAIRE
           protein kinase 1 [Mus musculus] /org=Mus musculus
           /taxon=10090 /dataset=nraa /length=469
          Length = 469

 Score =  469 bits (1195), Expect = e-131
 Identities = 225/330 (68%), Positives = 270/330 (81%)

Query: 97  FGAASSYLNLEKLGEGSYATVYKGISRINGQLVALKVISMNAEEGVPFTAIREASLLKGL 156
            FG A SY  LEKLGEGSYATVYKG S++NG+LVALKVI +  EEG PFTAIREASLLKGL
Sbjct: 129 FGKADSYEKLEKLGEGSYATVYKGKSKVNGKLVALKVIRLQEEEGTPFTAIREASLLKGL 188

Query: 157 KHANIVLLHDIIHTKETLTFVFEYMHTDLAQYMSQHPGGLHPHNVRLFMFQLLRGLAYIH 216
            KHANIVLLHDIIHTKETLT VFEY+HTDL QYM QHPGGLHP NV+LF+FQLLRGL+YIH
Sbjct: 189 KHANIVLLHDIIHTKETLTLVFEYVHTDLCQYMEQHPGGLHPDNVKLFLFQLLRGLSYIH 248

Query: 217 HQHVLHRDLKPQNLLISHLGELKLADFGLARAKSIPSQTYSSEVVTLWYRPPDALLGATE 276
            +++LHRDLKPQNLLIS  GELKLADFGLARAKS+PS TYS+EVVTLWYRPPD LLG+TE
Sbjct: 249 QRYILHRDLKPQNLLISDTGELKLADFGLARAKSVPSHTYSNEVVTLWYRPPDVLLGSTE 308

Query: 277 YSSELDIWGAGCIFIEMFQGQPLFPGVSNILEQLEKIWEVLGVPTEDTWPGVSKLPNYNP 336
            YS+ LD+WG GCIF+EM QG   FPG+ +I +QLE+I+ VLG P EDTWPGV  LP++ P
Sbjct: 309 YSTCLDMWGVGCIFVEMIQGVAAFPGMKDIQDQLERIFLVLGTPNEDTWPGVHSLPHFKP 368

Query: 337 EWFPLPTPRSLHVVWNRLGRVPEAEDLASQMLKGFPRDRVSAQEALVHDYFSALPSQLYQ 396
            E F + + +SL   WN+L  V  AEDLAS++L+  P++R+SAQ AL H+YFS LP +L++
Sbjct: 369 ERFTVYSSKSLRQAWNKLSYVNHAEDLASKLLQCSPKNRLSAQAALSHEYFSDLPPRLWE 428

Query: 397 LPDEESLFTVSGVRLKPEMCDLLASYQKGH 426
            L D  S+FTV  VRL+PE  + ++ K +
Sbjct: 429 LTDMSSIFTVPNVRLQPEAGESMRAFGKNN 458  (SEQ ID NO:8)


>CRA|18000005205923 /altid=gi|6912584 /def=ref|NP_036527.1| PFTAIRE
           protein kinase 1 [Homo sapiens] /org=Homo sapiens
           /taxon=9606 /dataset=nraa /length=451
          Length = 451

 Score =  468 bits (1191), Expect = e-131
 Identities = 224/330 (67%), Positives = 270/330 (80%)

Query: 97  FGAASSYLNLEKLGEGSYATVYKGISRINGQLVALKVISMNAEEGVPFTAIREASLLKGL 156
            FG A SY  LEKLGEGSYATVYKG S++NG+LVALKVI +  EEG PFTAIREASLLKGL
Sbjct: 111 FGKADSYEKLEKLGEGSYATVYKGKSKVNGKLVALKVIRLQEEEGTPFTAIREASLLKGL 170

Query: 157 KHANIVLLHDIIHTKETLTFVFEYMHTDLAQYMSQHPGGLHPHNVRLFMFQLLRGLAYIH 216
            KHANIVLLHDIIHTKETLT VFEY+HTDL QYM +HPGGLHP NV+LF+FQLLRGL+YIH
Sbjct: 171 KHANIVLLHDIIHTKETLTLVFEYVHTDLCQYMDKHPGGLHPDNVKLFLFQLLRGLSYIH 230

Query: 217 HQHVLHRDLKPQNLLISHLGELKLADFGLARAKSIPSQTYSSEVVTLWYRPPDALLGATE 276
            +++LHRDLKPQNLLIS  GELKLADFGLARAKS+PS TYS+EVVTLWYRPPD LLG+TE
Sbjct: 231 QRYILHRDLKPQNLLISDTGELKLADFGLARAKSVPSHTYSNEVVTLWYRPPDVLLGSTE 290

Query: 277 YSSELDIWGAGCIFIEMFQGQPLFPGVSNILEQLEKIWEVLGVPTEDTWPGVSKLPNYNP 336
            YS+ LD+WG GCIF+EM QG   FPG+ +I +QLE+I+ VLG P EDTWPGV  LP++ P
Sbjct: 291 YSTCLDMWGVGCIFVEMIQGVAAFPGMKDIQDQLERIFLVLGTPNEDTWPGVHSLPHFKP 350

Query: 337 EWFPLPTPRSLHVVWNRLGRVPEAEDLASQMLKGFPRDRVSAQEALVHDYFSALPSQLYQ 396
            E F L + ++L   WN+L  V  AEDLAS++L+  P++R+SAQ AL H+YFS LP +L++
Sbjct: 351 ERFTLYSSKNLRQAWNKLSYVNHAEDLASKLLQCSPKNRLSAQAALSHEYFSDLPPRLWE 410
```

FIGURE 2G

```
Query: 397 LPDEESLFTVSGVRLKPEMCDLLASYQKGH 426
           L D  S+FTV  VRL+PE  + + ++ K +
Sbjct: 411 LTDMSSIFTVPNVRLQPEAGESMRAFGKNN 440  (SEQ ID NO:9)

>CRA|18000005100533 /altid=gi|2392814 /def=gb|AAB70455.1| (U62391)
           PFTAIRE kinase [Mus musculus] /org=Mus musculus
           /taxon=10090 /dataset=nraa /length=423
          Length = 423

 Score =  467 bits (1190), Expect = e-131
 Identities = 224/330 (67%), Positives = 269/330 (80%)

Query: 97  FGAASSYLNLEKLGEGSYATVYKGISRINGQLVALKVISMNAEEGVPFTAIREASLLKGL 156
            FG A SY  LEKLGEGSYATVYKG S++NG+LVALKVI +  EEG PFTAIREASLLKGL
Sbjct: 83  FGKADSYEKLEKLGEGSYATVYKGKSKVNGKLVALKVIRLQEEEGTPFTAIREASLLKGL 142

Query: 157 KHANIVLLHDIIHTKETLTFVFEYMHTDLAQYMSQHPGGLHPHNVRLFMFQLLRGLAYIH 216
           KHANIVLLHDIIHTKETLT VFEY+HTDL QYM +HPGGLHP NV+LF+FQLLRGL+YIH
Sbjct: 143 KHANIVLLHDIIHTKETLTLVFEYVHTDLCQYMDKHPGGLHPDNVKLFLFQLLRGLSYIH 202

Query: 217 HQHVLHRDLKPQNLLISHLGELKLADFGLARAKSIPSQTYSSEVVTLWYRPPDALLGATE 276
            +++LHRDLKPQNLLIS  GELKLADFGLARAKS+PS TYS+EVVTLWYRPPD LLG+TE
Sbjct: 203 QRYILHRDLKPQNLLISDTGELKLADFGLARAKSVPSHTYSNEVVTLWYRPPDVLLGSTE 262

Query: 277 YSSELDIWGAGCIFIEMFQGQPLFPGVSNILEQLEKIWEVLGVPTEDTWPGVSKLPNYNP 336
           YS+ LD+WG GCIF+EM QG   FPG+ +I +QLE+I+ VLG P EDTWPGV  LP++ P
Sbjct: 263 YSTCLDMWGVGCIFVEMIQGVAAFPGMKDIQDQLERIFLVLGTPNEDTWPGVHSLPHFKP 322

Query: 337 EWFPLPTPRSLHVVWNRLGRVPEAEDLASQMLKGFPRDRVSAQEALVHDYFSALPSQLYQ 396
           E F +   +SL  WN+L  V  AEDLAS++L+  P++R+SAQ AL H+YFS LP +L++
Sbjct: 323 ERFTVYNSKSLRQAWNKLSYVNHAEDLASKLLQCSPKNRLSAQAALSHEYFSDLPPRLWE 382

Query: 397 LPDEESLFTVSGVRLKPEMCDLLASYQKGH 426
           L D  S+FTV  VRL+PE  + + ++ K +
Sbjct: 383 LTDMSSIFTVPNVRLQPEAGESMRAFGKNN 412  (SEQ ID NO:10)
```

Hmmer search results (Pfam):

SPLICE FORM 1:

| Model | Description | Score |
|---|---|---|
| E-value | N | |
| PF00069 | Eukaryotic protein kinase domain | 247.7 |
| 1.6e-70 | 1 | |
| CE00031 | CE00031 VEGFR | 14.3 |
| 0.0002 | 1 | |
| CE00359 | E00359 bone_morphogenetic_protein_receptor | 7.1 |
| 0.25 1 | | |
| CE00022 | CE00022 MAGUK_subfamily_d | 6.0 |
| 0.11 1 | | |
| CE00287 | CE00287 PTK_Eph_orphan_receptor | -59.4 |
| 0.00019 | 1 | |
| CE00292 | CE00292 PTK_membrane_span | -61.0 |
| 1.9e-05 | 1 | |
| CE00286 | E00286 PTK_EGF_receptor | -76.4 |
| 1.9e-06 | 1 | |
| CE00291 | CE00291 PTK_fgf_receptor | -87.0 |
| 0.00095 | 1 | |
| CE00290 | CE00290 PTK_Trk_family | -100.0 |
| 1.4e-08 | 1 | |

FIGURE 2H

| | | | |
|---|---|---|---|
| CE00016 | CE00016 GSK_glycogen_synthase_kinase | -152.6 | |
| 3.5e-08 | 1 | | |
| CE00288 | CE00288 PTK_Insulin_receptor | -196.5 | |
| 0.0012 | 1 | | |

Parsed for domains:

| Model | Domain | seq-f | seq-t | | hmm-f | hmm-t | | score | E-value |
|---|---|---|---|---|---|---|---|---|---|
| CE00022 | 1/1 | 204 | 231 | .. | 126 | 153 | .. | 6.0 | 0.11 |
| CE00359 | 1/1 | 222 | 247 | .. | 274 | 299 | .. | 7.1 | 0.25 |
| CE00031 | 1/1 | 204 | 247 | .. | 1051 | 1094 | .. | 14.3 | 0.0002 |
| CE00290 | 1/1 | 106 | 307 | .. | 1 | 282 | [] | -100.0 | 1.4e-08 |
| CE00288 | 1/1 | 106 | 310 | .. | 1 | 269 | [] | -196.5 | 0.0012 |
| PF00069 | 1/1 | 103 | 326 | .. | 1 | 220 | [. | 247.7 | 1.6e-70 |
| CE00286 | 1/1 | 103 | 335 | .. | 1 | 263 | [] | -76.4 | 1.9e-06 |
| CE00287 | 1/1 | 104 | 335 | .. | 1 | 260 | [] | -59.4 | 0.00019 |
| CE00016 | 1/1 | 1 | 340 | [. | 1 | 433 | [] | -152.6 | 3.5e-08 |
| CE00292 | 1/1 | 104 | 341 | .. | 1 | 288 | [] | -61.0 | 1.9e-05 |
| CE00291 | 1/1 | 104 | 341 | .. | 1 | 285 | [] | -87.0 | 0.00095 |

SPLICE FORM 2:

| Model | Description | Score | E-value | N |
|---|---|---|---|---|
| PF00069 | Eukaryotic protein kinase domain | 263.6 | 2.6e-75 | 1 |
| CE00031 | CE00031 VEGFR | 14.3 | 0.0002 | 1 |
| CE00359 | E00359 bone_morphogenetic_protein_receptor | 7.1 | 0.25 | 1 |
| CE00022 | CE00022 MAGUK_subfamily_d | 6.0 | 0.11 | 1 |
| CE00016 | CE00016 GSK_glycogen_synthase_kinase | -42.5 | 3.2e-14 | 1 |
| CE00287 | CE00287 PTK_Eph_orphan_receptor | -55.2 | 0.0001 | 1 |
| CE00292 | CE00292 PTK_membrane_span | -63.9 | 2.8e-05 | 1 |
| CE00286 | E00286 PTK_EGF_receptor | -76.4 | 1.9e-06 | 1 |
| CE00291 | CE00291 PTK_fgf_receptor | -88.8 | 0.0012 | 1 |
| CE00290 | CE00290 PTK_Trk_family | -94.9 | 6.1e-09 | 1 |
| CE00288 | CE00288 PTK_Insulin_receptor | -196.5 | 0.0012 | 1 |

Parsed for domains:

| Model | Domain | seq-f | seq-t | | hmm-f | hmm-t | | score | E-value |
|---|---|---|---|---|---|---|---|---|---|
| CE00022 | 1/1 | 204 | 231 | .. | 126 | 153 | .. | 6.0 | 0.11 |
| CE00359 | 1/1 | 222 | 247 | .. | 274 | 299 | .. | 7.1 | 0.25 |
| CE00031 | 1/1 | 204 | 247 | .. | 1051 | 1094 | .. | 14.3 | 0.0002 |
| CE00288 | 1/1 | 106 | 310 | .. | 1 | 269 | [] | -196.5 | 0.0012 |
| CE00286 | 1/1 | 103 | 335 | .. | 1 | 263 | [] | -76.4 | 1.9e-06 |
| CE00292 | 1/1 | 104 | 335 | .. | 1 | 288 | [] | -63.9 | 2.8e-05 |
| CE00291 | 1/1 | 104 | 339 | .. | 1 | 285 | [] | -88.8 | 0.0012 |
| CE00290 | 1/1 | 106 | 354 | .. | 1 | 282 | [] | -94.9 | 6.1e-09 |
| CE00287 | 1/1 | 104 | 367 | .. | 1 | 260 | [] | -55.2 | 0.0001 |
| PF00069 | 1/1 | 103 | 387 | .. | 1 | 278 | [] | 263.6 | 2.6e-75 |
| CE00016 | 1/1 | 1 | 434 | [. | 1 | 433 | [] | -42.5 | 3.2e-14 |

FIGURE 2I

```
   1 TATAGGCCAA TGCTGTGGCT CACGCGTGTA TTCCCAGCAC TTTGGGAGGC
  51 AGGAGGATCG CTTGAGCTCA GGAATTGGAG ACAAGCCTAC GTAACATAGT
 101 GAAACCTCTG TCTGTACAAA TAATAAAAGA ATTTTCCAGG CATGGTGGCG
 151 TGCACCCCCA GTGCCAGCTA TTTGGGAGGC TGAGGTAGGA GGAATGCTTG
 201 AAGCCAGGAG TTGAAGACAA GCCTAGGCAA CATAGTGAGA CCCTGTGTCT
 251 ATAAAAAATA ATTAGCTGGT TGTCTTGGCA CAGGCCTGCA GCTAGCTACT
 301 CGGAAGACTG AGGTGGGAGG ATCACTGAGC CCAGGAGGCT GAGGCTGCAG
 351 TGAACAGTGA TCACCCAGCT GGATTCCAGC CTGGAAGACA GAGGGAGACC
 401 CTGTTTCCAA AAAAAAAAAA AAAAAAAAAT GCAAGAAAAG ACATCATAAA
 451 CTTGACCTGG GACATAACTT TTATGTGATG AAATTCACAA TCTTTTAGGA
 501 AGAAATTAGC ATTTCTGATA AAATGTATTA TAATTATATT ATTATAAATT
 551 CAAATGGAAT TAAATATTCT GAGAAACTAG CTTCTCACTC TCTCAGTTGT
 601 CAGTCAAAAC TTTAATGGTC TTTGGCCGGG TGCGGTGGCT CACGCCTGTA
 651 ATCCCAGCAC TTTGGGAGGC CGAGGCGGGT GGATCACAAG GTTAGGAGAT
 701 CGAGACCATC CTGGCTAACA CGGTGAAACC TCGTCTCTAC TAAAAATACA
 751 AAAAATTAGC CGGGTGCGGT GCCAGACGCC TGTAGTCCCA GCTGCTCAGG
 801 AGGCTGAGGC AGGAGAATGG TGTGAACCCG GGAGGCGGAG CTTGCAGTGA
 851 GCCGAGATTG CGCCACTGCA CTCCAGCCTG GGCGACAGTG CGAGACTCTG
 901 TCTCAAAAAA AAAAAAAAAA AAAAGTTGAA TGGTCTTTGA GCCAAGTAGT
 951 CTTCCTTTTC TTCTTCTTCT TTTTTTTTTT TTTTCAAAAA ATATCTCTAG
1001 ATTGAATCTT GGAATTGGCT TAAGTCTCTT CTCTTGTGGC AATTTTGAAA
1051 TGAAAAAATA CATGCTCATA ATTAAATTAC CTGAACATTT TAAAAAACCA
1101 TCATGAGGTT CAAATATCAA ATATTCATAA ATATTGTTGT GATAATAGAC
1151 ATAACTCTTA TTTTTTCCCT TAATAATGAT TGTTTATATA TCCTCCATTC
1201 TGTCTCACTT TATGATTAGT ATATTATAGT GGCAATAATC TTAGGAATCT
1251 AACAGAGAAA AGTGTTGCAT TTGAAGACTA CAGACTGCAA ACCAATTTAA
1301 GCCAGATTCC TTGACATGTT GTGCTGTTAA TATAGTACTT TACATATAGT
1351 AAACATTAAT TACATATATG TGGAAGGAAG CAAGCAAGAA AGGAAGAAAG
1401 TATTTCATTC AAACTCCTCT CTCTCCATCA CCATTGGCTA ATATCATCAT
1451 TTGTACAGTT AAGAACAACA TAGGTGCTCA CCACATAGTT TTTGAATAAA
1501 TGAATGAATG GCAACCCTTC TAAGACTATT GGATACACTA TTGTTTGAAG
1551 GCAAAGAGAT GCAGTAGATA TTTTCAACTT TTTTCCTGTT TTATGATTCT
1601 GTGGTTTCTT TGACTACTAA AAGTTAGCTA GGTAGCAAAT TTGTTTTAAA
1651 GTCTGAAAAC CAAAATGCTT TCAGATAAAA GGTAGGGAGA AAAATACTCC
1701 TCAACATGTC CACTTTAGCA CCAGGAAAAC CTAATATCAA TATCACCATC
1751 AATGATATCA TATAAATATC ATTGCATAGA TAAGCAATGT CAATCCCTAA
1801 AAACTATGTA TACCAATAGC ACTAACTTGT GGCCAGAACA AGAACCTTAA
1851 CTGTGCCAAA TTTTATTCTA TTCAATAACA GCTGCCTCGT TTTCAGTTGT
1901 GCACATCTGA ATGCAAGCAA TCCCTGTCTG ATGTGGAGTT TCTTGCACTG
1951 ATAAGGAAAA ACTGCTGAAG TTGTGAGGCT GCTCCAGGCA GAGCCATCAT
2001 GTGAGTCATA TGAAAGCTCC ACGCTGCTGA CCTCTGGCAA AAAGGGAGAG
2051 AACAAGGATA GGAGAGGCAG TGGGGGAAAG GTTCAAGTGC GGGTTTTCTC
2101 CTTGAACCTA CAAGATTATG GGTCAAGAGC TGTGTGCAAA GACTGTACAG
2151 CCTGGATGCA GCTGCTACCA TTGTTCAGAG GGAGGCGAGG CACACAGCTG
2201 TCGGAGGAGT CAGCCTGAGA CCACGGAGGC TGCGTTCAAG GTATTTGTAT
2251 CCCAGGAGAG AGCATCTTTC TCTATTGATA AACCAAGGAG TTCAGACACT
2301 CCCTTTTTGT AGCGGGATCT GATTCTTCTG CGGTAGGTCT AAACCAATAA
2351 AATGAAAATT CTATTAAAGT CACAGAAAAT TTATGGCTGT AGTTATCAAA
2401 TTTGGGGAAT TTCTTGTAAA CCAAAAGGGA AAAATAATCC TTGGCTTTGG
2451 GCTGCACGAA ACTCACTTGG CTTGAAGTCG AGAAAGTAGT TCTCTCAAAA
2501 TCTCTAAGGT CCTAAATTAC AGAGCTGAAA CTTAAAAGGC AAGCTGCAGT
2551 ATTAGTTGGT ATGCTATGGA TTTGAAACTT TAGTAATTAG TTCATGATTA
2601 TTAGCAATGC CATAGATTAT TCCCCTACAG CAATAAATTA AGTGGACATG
2651 AAAAAAAAAA GCCAGACTTA AACAGAAAAA AGTTGCAAAA CATCCATCAA
2701 AGAGATTTAG GTTAACCTGA ATGTTAAAGA CACATTTTTA GGTGAAGAAA
```

FIGURE 3A

2751 GAATGTAGTA TTTCAGGAGT TGATACCATT ATGGTCTTTT TCAGGGATCT
2801 TTCAAGAAAA GTGCCTTTTG GGGGTACAGG AAGCTTAGAA AACATTTGAA
2851 GAGTGAAAAT GAGGCAAATA AAGAAAAAAT GGTTTTACCA GGCACTGAAT
2901 CTTTACTTTG CATAAATTTT ATTTCTGCTC TTTCTTTTTT CTCTAGCTAA
2951 CAGACCTAAA AGAAGCATCA TGTTCCATGA CTTCATTTCA CCCCAGGGGA
3001 CTTCAAGCTG CCCGTGCCCA GAAGTTCAAG AGTAAAAGGC CACGGAGTAA
3051 CAGTGATTGT TTTCAGGAAG AGGATCTGAG GCAGGGTTTT CAGTGGGTGA
3101 GTGAGCAGCT GATGTTGATC AAGAAGAATT TAATGTGAGC TTGTCTACGG
3151 AGGCCGGCCC TTGCTTCCAG GGCAATTACT GAGCGAGCCT TCCCAAGTCT
3201 GCTCTGGCAA TGCTGTCTAA TTTCCCTGGG GAAAAAAAGT CAACACTAAA
3251 AAAAAGTGTT CTTTCTCTCT TCCCTTTCAC CCGCTCCTTT TCCCCATTCC
3301 CCTAGAGCAG AGGAAGAGCC TCCCTTTTGG GGCAGCCTCA TCTTACTTGA
3351 ACTTGGAGAA GCTGGGTGAA GGCTCTTATG CGACAGTTTA CAAGGGGATT
3401 AGCAGGTGAG TGACACATAG CTGGGAGAGA CTTTAGAGAT GAGAGTCCCG
3451 CCCCCCCAAT TTCATATTAT AAAGCCAGGT GAGACATCAT AGAAGTTCAT
3501 AGCACTCAGG ACCTGTGCAA GACACCATGG CCGACAGGGA GAGAGACATG
3551 ATAACTTAAA CAGCCTTGAA AGAAAAACAA ACCTGCCCTG CCCTAATTAA
3601 AATCAGCCCA CTTAAATGTT TATCAGCCTT TCCCTTCTTG CATTCAATTC
3651 AGAGAATTCA AAGAAAATAG ACATTCTCTA CTACTGACCC AAAGAACAAT
3701 TATCACTCTT CAGGCCTGTG GGAGGCACAG TTGGTAAAGC GTCTCTAACA
3751 GGTTTTTTAT ATCCCTCCCT AAATCACAAT GACAGAGTTT TGTAATGGCA
3801 ACCTGGAATT TGCTGCTTCA TTCCTCCACC TGGCCTTTAT AGAAGAAACT
3851 GAAGTTGGTT TCTGCAAATT ATGGTACATG CAAAAGATGA TAAATCCTAG
3901 ATTTTTTATA TTTGCAAAAT ACACAAAATG TCTGGAGAAT AAAAATACTG
3951 CTTATCCAAA AGCTAAGTAC TAATTTTGGT AAACAACCAA CTTTGTTAAA
4001 TATATGTAAA AGATCCATGA ATTCCCCTTT TAGTCAAGGT GGGAAAGTTG
4051 GATGGTCGCT TTTTTCTTTA TGTTACTCCA ATAGAGAGAA AAGTAATGGC
4101 TCAATAGTGG TTAAATATTA ATTTTAAAAA TATAGCTGAT CCGAGTGCAG
4151 TGGTGTTTAC AACTACTTGA TCACAACCAG TTACAGATTT CTTTGTTCCT
4201 TCTCCACTCC CACTGCTTCA CTTAACTGGC CAAAAACGAA AAAAGAAAAA
4251 TTTTATATAA CTACTACAAG ACTAAATATT TATTATTTAT CTTAGTATTT
4301 ATGCTGTTAT TATTATTTTT ACTTGTTAAA ACAGGATTGT AGGGGACATA
4351 CAGTTTTATT TTATTTTATT ATTTATATAT TTATTTATTT ATTTTGGAAT
4401 GGAATCTCTG TCACCCACGC TGGAGTGCAG TGGTGCGATC TCAGATGACT
4451 GCAACCTCTG CCTCCTGAGT TCAAGCAACT CTCCTGCCCC TGGCCCTTTA
4501 TACTTTCTTA ATCTGTTTTA GTCATGGTGT ACCTTAACTT TTTTCAATGC
4551 TGAGAACATC TGCAATAAAG GACCACATTT TATTTTATTC TAAGCTTCCT
4601 CATATCAATT TGGCCATGGT AACTGTTTTC AAGGTGGCTC GGAACGGGGG
4651 CACCCTGGAA CATACTTGGA TACATGGGCA CCATGGACAC TTCTGATCCT
4701 CTCTTCTGAG TTCTGACTTT GATTGTTCTG CACAGACCTT TCCAGCCCGA
4751 AGTTTACACA GAATTCACTT ATCTTTTCTT CTAGTTACTT TATGTTTTCT
4801 TTTTCATTTA ACTCTTTCAT CTACTGGGAA TTTATATTGT ATATTCACAA
4851 TCACCCCAGC TCCATTTATT AGATTTTCTT TTCTCTGATG GTTTGAAATG
4901 CTGCCATGAT TATATATTAG ATCTCACGAA TACTTGAAAT TCTTTCTGTT
4951 CTAATCTTTT AAAAATCATG TTTCCTTAAT CTATCTTTTC TTATATTTGT
5001 GCTGCATGAT TTTAATTATT GTTGCTTTAG GCTATTTTTA GAATATATCA
5051 AAACTCTACG TTAGAGAATT ATTGACATCT TTGCATTATT AGATTTTCTA
5101 ATACAAATAT CCTGTAAATA TCTAATACAA CAGTCTCTGG ATGGTCACTG
5151 TACAAGACCC TATAGAATCC CTACCCTCCA TTCCCCGGCA CACACTCAGC
5201 TCCTCCCTGT CCTCATCTCC TTCCCCTCTC CTGCTTCAAT GACAGACTGC
5251 TCCTGCCTCA GTCAAGGACT TTTAACTTGC TGTTCCCTCT GCCTGGAGCT
5301 GCCTTCCACT GTTCATGCAC ACAGCTGACT CCCCCTCGCC ATCAGATTCC
5351 TGGTTCAAGT GTTACCTTAT TTATAAAACT GTAGTCCCAG CTAGTCCAGG
5401 GAGGCTGGAG GCAGGAGAAT CACTTGAACT TTGGAGGCAG AGGTTGCAGT
5451 GAGCTGAGAT CGGCACCACC GCACTCCAGC CTGGGTGAGA GTGACACTGT

FIGURE 3B

```
5501 CTCAAAAAAA AAAAAAAGCA TTTTCTCTTA TAAACATATT TGCCAAAAAA
5551 CTTTTTGCAG GGTTTGGGGG AGAATTTCAC AGAACCATGT TCTGAGGAAA
5601 ATACTTACCT CATAAAACTC TAAAACAAAA TTTCAAAGAC ATGATAAGGC
5651 AAACAAAAGA AACTGGGGAA AAGTATATGC AAAATAGTTC AATAAAAAGG
5701 TGGGCAAATC GGCAAATCAC AAGAAAAACA GAAAAGATCC ATAAACTTAT
5751 GAAAAGTCAG TTTCACATAT GGTTAAAGAA ATATAAATTA AAATGCGATA
5801 AACCTTTTTA CTTTTCAAAT AGGCCAAAAA AAAAAAGAAG ATGAAAGCGA
5851 AAAGCCAACC CACATGATAG GGCTATGACA GAGGGACACA GGAGCCAACT
5901 GAAAGAGCTT CCAAAGGACA AAGCTGCAAA AATATGAGCA ACCAAAAAAA
5951 GTGGTATTAA ATTATAACCC AAAGTATAAA ATAAATATCT ATGAGTCCGT
6001 ACTGATATAA ATAAATGATT CAATACATTA ACAAATGGGA GAGAAGAAAC
6051 AAATCTCTCA TGCCAAATAA ATACAAATAA TTTATGTAGA TAATATACCT
6101 TCAAAGAGGT ACAGCATAAC TCTCCACTCC TTAAGTGTGG GTCATTCATA
6151 GTGGCATTTC TCTAAAAGTA CAGTATGAAA AAGGGGGAGA AAGAGTAACT
6201 TTAGAGTAGA GAAACCTGAC CAACACTATC TCAGACAGGT GACTAAGGTC
6251 AACATCAAAA GTCATAAATC ATGATGATGG TATGCACTCT TTTTTTTTTT
6301 TTTTTTTTTT TTCTCAGATG GAGTCTCACT CTGTCGCCCA GGCTGGGGTG
6351 CAGTGGCGCA ATCTCAGCTC ACTGCAACCT CCGGCTCCCG GGTTCAAGCG
6401 ATTCTCCTCT CAGCCTCCTG AGTAGCTGGG ATCACAGGCG CGTGCCACCA
6451 TACCCGGCTA ATTTTTTGTA TTTTAGTAGA GACGGGGTTT CACCATGTTG
6501 CCCAGGCTGG TCTCAAACTC CCGAGCTCAG GCAATCCACC CACCTCAACC
6551 TCCCAAAGTG CTAGGATTAC AGGCATGAGC CACTGCGCCT GGCTGAGGGT
6601 ATGCACTTTT TTTTTTTTTG AGACGGAGTC TTGCTCTGTC GCCCAGGCTG
6651 GAGTGCAGTG GCACGATCTT GGCTCACTGC AAGCTCCGCC TCCCAGGTTC
6701 ACGCCATTCT CCTGCCTCAG CCTCCCCAGT AGCTGGGACT ACAAGGTGCC
6751 CCACCACCCA CACCCGGCTA ATTTTTTGTA TTTTTAGTAG AGACGGGGTT
6801 TCACTGTGTT AGGCAGGATG GTCTCGATCT CCTGACCTCC TGATCCACCG
6851 GCCTTCGCCT CCCAAAGTGC TGGGATTACA GGCGTGAGCC ACTGTGCCCG
6901 GCCTGATGAA ATGTTAAATC TTTATTAAAT ATCGGATTGT ACAAGAATGA
6951 ACTATAAGAG AAAAGTTACA TGGAGGAAAA AAGGTTACTA ACAATATGAT
7001 TTTAATCCCA CTGTATTAAA AACAATGGAT TTATACCTGC ATTAAAATCT
7051 TCTCTATTCT CAGCACTTAG CTGATATGAA TAAAATGATG AATGAGGGGA
7101 CAGTAGGAGG AAATGAAGAG AGAGAGAATA ATGGTGTGGC CTGGGAAGAT
7151 CAGGTAGCAC TTAGAAGCCC GCTGCAAGAA TTTGGCTTTT ATTCTAAGTA
7201 ATGCGTGGAG ATATGGTGGC TTTTGAACAG AAAAGTGACT TGTCCTGATT
7251 GTCATTTGAA AAGTATGCCT CCAACTACTA CTGCTGAGAG TAAATAGTAG
7301 GAGTGCAAGT GTGCTCAGCA GGGAAACTGT TAGAAGACCA CTACAAGGCT
7351 GGGCTTGGTG GCTCGTGCCT GTAATCCCAG CACTTTGGGA GCCTGACGTG
7401 GGCAGATCAC CTGAGGTCAG GAGTTCGAGA CCAGCCTGGC CAAAATGGTG
7451 AAACCCCCAT CTCTGCTAAA AATACAAAAA TTAGCCAGGT GTGGTGGGGG
7501 TCCCCTGTAA TCCCAGCTTC TTGGGAGGCT GAGGCAGGAG AATTGCTTGA
7551 ACCCAGGAGG TGGAGGTTGC AGTGAGCCAA GATCGTGCCA CTGTACTCCA
7601 GCCTGGGCAA CAGAGCGAGA TTCTGTCTCA AAAAAAAAAA AAAAAAACAA
7651 AAAAACAAAA AAACACTACA ATAAGTCAGA TGAAAAATAA TAATAAGCTC
7701 CAAATTTTCT ATAATGGACA TATATATATA TATCACTTTA GTAAAGAGGG
7751 AAAATGCTTT GGAATATATA TGTTATATAT GTATTGATAC ATGTTAAACT
7801 TTTTATTTTG AGAAAATTAT AGATTTATAT GCTAGAATAT ATTTTGAAGT
7851 GAAAGTGCTT TTGTTAAGCC ATCTTTGGTA TAAATTGCTG CTTTGAACCA
7901 CCTCAATAAG TGTGTGCCCC TCAATCCCTC TCTTCTAGAA TAAATGGACA
7951 ACTAGTGGCT TTAAAAGTCA TCAGCATGAA TGCAGAGGAA GGAGTCCCAT
8001 TTACAGCTAT CCGAGAAGGT AAGAACAGCA GAAATGGACC CAATAGATCT
8051 GTTTTGAGTC CTTGATTTGG TAAAAAATGT ATTGCATTGA TCCATTCAGC
8101 ATCTAGTTTT GATTCTTCTG GAATACTATA ATTACATTTT TATTTTTCAT
8151 ACAAGTTTTT CAAGAAATTT ACACTGCTAT TTTATTACTT AATTTTGAGG
8201 AAATTGAGAT TTAAAACTAT TATATCACTT GACCAAAACT ATAAATTCAC
```

FIGURE 3C

```
8251 TGAGCAATTA CTAATACTTT CCATGTGTTT GGCCTCATGC TAGGTGCTAA
8301 GGCTATACCT ATATAACCTC AGAAAATTCC TATAAAAGAG AAAATATATA
8351 ATCACACAAA TTCTTACTGG GAAATTTGCC TGAACATAAC ATGTTGTTAG
8401 CTAGCACTTG GAGATTCTCC AGAAGGCATG CATGTTTAGT GTTACTGCCT
8451 GTATTTTCTC TGTGCCCTGG ACAGTACAGC AAATGGGTGA GGAACCTGGT
8501 GTCAAATGGA CTTGGGTTTG CAGCACAGGT CCACCAATCA CTAGTGGTAT
8551 GATGTTGGGT AGGTTACTTT AGCTATTTAT TACTCAGTTT CTTGCAGGAA
8601 GAGGATAATA GTGGTACCTA TTTCATGGAG TTGTTATGAG TATTCAACAA
8651 GAATATGTAT ATAAAGCACT TATCACAGAG TCAGTTTTTC AGAGTTCAAC
8701 AAATGTTGAC CATTTTTATT CCATTCTTCT TTTCCTGGGT AATGTCTTAT
8751 TTACCATCAA GATAACTAAT ACTTTATAAC ATAAACATCA AGAAGCCAAC
8801 ATAGTGAAAT GAATCATTAA AAATATAATT TATCAACCTT TATTGCATGA
8851 GCCATTTGAA ATAAGATGAT GATAGGATTG CTATGCATTT CAGCAAAATC
8901 CCAGAGAAAT GGCACTTCCC TGGCCTTATT TTCTCCCACT TTTAACTACT
8951 TATCTTCTGT TCTTTACTGA GCACATGCTA TATGCAGAGT ATGCTGCTGG
9001 ATGCTGTGAA GGATGAGAAG AGAAACCCAT GTCTTTGTTC TATCATTTGC
9051 AGTCTTAACA GAGCACATGA TTCAAGTTAC AAGTGTATAA AAGACATAAA
9101 CTAAGATGAG AGCAAGTTAG TCTCAGTGTG ACTGATGGAG TCACTAGATT
9151 TTGAACTGAG CTTGGAAGGA TAGGTTATGC AAACAAGCAT GGAAAAAGCA
9201 ATTCAGAAAA TGAGTTTATA ACTGAATTTG ATACCCTTTT CAAAAGTCTT
9251 TCAGAGCCCC TGAGGAATAC ATCATTTTGA ATTTAATTGG AAGGGCCAAA
9301 TGGGCTATTG GTTTAGCCAG AGATTCATCC TGGTAGGATC AGGTGCATTC
9351 TGGGAGAAGG CATGGTTTTA AGTGTTTAAT ATAATGGAAA CTGCATTAAC
9401 TAATGTACTT ATTAATGGTC TCCATGAAAG GATGATCAGA TTTGGAAAGA
9451 GATGTATGGA TAGGTTAAAG AGTATTTGTG AACGTAATAG AAATTCCCAG
9501 GTCACCCGCA TAAGAGGAAG GTTTCCTTTG TGAGCTTGAG TTTGCCAATT
9551 GCTTAAGATT GGCTTTGCTT AGATATTGCC CACAGCCAAG TTTTTCAGGT
9601 TGACATTTAA CTGTAACAGT GAAACCTTTT GCCAGGTTTG CTAACAGATG
9651 GTTCTCAGCA TGGTTCAGAA AACCTGGATC CGTTTTCTTC TGTATGCTAA
9701 ATGTTTCTTT CATTGCATAT TTACGGAGGA ATTGCCTCTC CATCACAGGT
9751 GTTTACAATT ACATTTAGTA GTCAACTGTG GACTTTCTTG GTTTGTTTTA
9801 TGGACTTACC TTACCGAATG CTTTGCTCGT GTAATATTAA AAACCACAAG
9851 AGGATTTCTG ACACATTGGA GGTTGTTAGG AATCCAATTT CCAACAATGA
9901 ATGTTTCTTT TTACACCACT ATAAAAGCTT GGAGCCCTTG TTAAAAGAGC
9951 CCTCTCCCCT CAAGAAGATA TGAGGCTTTA TTCGAAAACT TTGGCACTGT
10001 CCCATTTTTC CTGTAAGAAC TTTAAGGATG TGAGACCAGG GAGACAGGAG
10051 GTTAAATGAG AAGGGCTGGA AGGCAAAGTA AGAACAGCTG GAGTTCATTA
10101 GCTAAAATCC AGGGTCACTA GCTAAAAAGG CAACCGAAAG GCACGTGCAG
10151 GAAAACTGAA CAAGTAATGC AGCCCTCTTT AAAAAGCCTT GAAGCAGGAA
10201 TTGCTTTTCC TGAACAATTT GGCTGCCCTG ATGGTATAGC AGCCAAAGAT
10251 TTATTAAGTA TGATTTTACT ACATATATGG TCTCTTTCTA TACAGGTAGA
10301 ATACATGTGG CAATTTACTA GTCTGGTCAT TTGGAGTACT ATTTTCATTT
10351 GACCTTAACA TGTGATATTA TGAAACTAGC AAAAGTATGA ACAGCACTAA
10401 GGAACATTTT TTTTTTTTTT TTTTGAGACG AAGTTTTGCT CTTGTTGCCC
10451 AGGCTGGAGT GCAATGGCAC AATCTTGGCT TACTGCAACC TCTGCCTTCG
10501 GGGTTCAAGC AATTCTCCTG CCTCAGCCTC CGGAGTAGCT GGGATTACAG
10551 GCATGTGCCA CCACACCCAG CTAATTTTGT ATTTTTAGTA GAGACAGGGT
10601 TTCCCCATGT TGGCCAGGCT GGTCTTGAAC TCCTGACCTC AAGTGATCTG
10651 CGTGTCTCAG CCTCCCAAGG GAAATATATC TTAATACATG TGTCAGTGCT
10701 TTTCATACTT CTTTCAATCC TCTTAACAAT CTTTAGAGAT AGATATTATT
10751 AATATTATTC CACTATATGG TGGTGATTCA AACCAAATCT CTCTGATTCA
10801 AAAATTCATA GGCTTTCTAC GCACCCACTG TAGAAATATT CATTTAGCAC
10851 CTACTATGAC CAGGTACTCT GCCGAACTGC TAGATACACA GCAATACACA
10901 AAATAGATGT GTTCCCTACC ACCCTCATTC CTTTGCTAAT TAAGAAAAGC
10951 AGAGGCCTTC ATAGTGCCTT GGAAATCTCT CATAATTGAC TCTAGAATTG
```

FIGURE 3D

```
11001 TATTTTAAGT GTTGATTTTT ACAACTAGGA GGAAATACTT TCATTTGAAT
11051 AGGCTAATGT GTTATGTTTT TACATAGTAC AACATTTCTT AGTTTTATGA
11101 AACTTTATAG CAATATCTTA ATATAATGTG CATTGTTTTA AATATTTTTG
11151 TTCAAGTGGT CAACTTTTGG TTTAAACTGA GGACTTTCAG CCTGTTAATA
11201 GCATTTTTCT TAGGAAGGAG TCATATAACT AATCTTTTTT GAGGACAAGG
11251 CATATGACAT AATCTCCCCC TTCCCCTACA TAATGTATAT TTTTAAAACC
11301 TTTATACCAA CCCTAGGAAG TAAAATGTGC TATTTTTGTT GTAGAGATAA
11351 AGAAATTCTA GCCTCAGAGA GGTTAGTTAA CTTGTCTGAG GTCACAGAGA
11401 TAGTAATCAG AGTTGTTAGA ATCCATTTCT ATTCTATTTA AAATCCCTTC
11451 TACTTTATTA TGATGAATTT GGAAATGCTT AACTAAAGTA TTTATTGTTT
11501 AGCAACAGTA AAAATAAAAA TAGAAATCTG TTTTTATTAT ACATTTTATA
11551 TAAACGTTAA GGAAAATGCA GAAGAAGTAT TTTTTTAATC TTTAATTTTA
11601 GATTCAAGGG GTACATGTCC AGGTTTGTTA CATGAGTATA TTGCATGATG
11651 CTGAGGTATC TTGTCACCCA AATAGTGAGT ATAGTACCTG ATAGGTAGTT
11701 TTTCAACCCG TGTCCCTCTC CCTTCCTCTC CCCTTTTGGA GTCCCTGGTG
11751 TAGTGTCTAT TATTCCCATC TTATGTCTGT GTGTTCCCAA TACCCCCAGT
11801 TATTAGCTTT CACTTGTAAG TGAGAACATG TGGTATTTGT TTTCTGTTCC
11851 TGGGTTAATT CACTTAGGAT AATGGCCTCC ATCTGCATCC ATGTTGCTGC
11901 TAAGGAAATG GTTTTTTTTT TTTTTTTTTT TTGTGGCTGC ATAGTGTTTT
11951 ATGGTGCCAG TGTACAAATT TTCTTTATCC AATCCACCAT TGCTGGGCAC
12001 CTAGGTTGAG TCCATGTCTT TGCTATTGTG AATAGTGCTG TGACGAACAT
12051 AAAAGTCTAG GTGTCTTTTT GACAGAACGA TTTATTTTCC TTTGGGTATA
12101 TACCCAGGAA TGGAATTGCT GGGTCAAATG GTAATTCTGT TTTTGGTTTT
12151 TTTGAGGCAG GAGATGGGAC TCGACTCCAG AGATGGGGCT TGAACACTAA
12201 ACCAAATTTA GGACTAGCCA AAACAGGGCC TGGGGGGAGG CAGCTTTCCA
12251 GAAGACACAC CCACCAGTGT GCCATGTCAG TTTACCATTG CCATGGCAAC
12301 ACCTGAAAGT TACCACCCTT TCCCGTAGCA ACAACCTGAC AACCTGGAAT
12351 TACCACTCTT TTCCTAAAAC TTTCTGCATA AACTGCCCCT TAATTTGCAT
12401 ATAACTAAAA GTGGGTATAA ATATAACTGT AGAGCTACCT ATGAGCTGCT
12451 ACTCTGGGCA CACTGCCTAT GTGGCAGCCC TGCTCTGCAA GGAGAGGTAC
12501 ACCCGCTGCT GCTGAACACT GCTGCTTCAA TAAAAGCTGC TGTCTAACAC
12551 CACAGGCTCA CCCTTGAATT CTTTCCTGGG TGAAGCCAAG AACCCTCCCA
12601 GGCTAAGCCC CAGTTTTGGG ACTTGCCTGC CCTGCCTCAC TTTGAGAAAT
12651 TTCTAAACTG TTTTCCACAG TGGCTGAACT AATTAACATT CCCACCCACA
12701 GTGTATAAGC ACTCCCTTTT CTTCTCAAGC TTACCAGCAT CCATTAACTT
12751 TTTACTTCTA AATAATAGCC TTTTTGACTG GTGTGAGATG GTATCTCATT
12801 GAGGTTTTGA TTTGCATTTC TCTGATGATT CGTGATGTTG AGCAATTTTT
12851 TCATATGTTT GTTGGCCACT TGTGTGTCCA AAAGAAATAT TTTAAAGAAA
12901 ATAATACATC ATGTTGTATA TTCATCAATT CTGATTCTAT CATTGATTCT
12951 ACAGTGCCGG TAATTGCAGT GTTTAAATTA GAAACAGTCT CAGCTAAGAA
13001 TCTTTTAAGA TCATTCTCTA GTAGAAAAAC ATTACAAAGT AATGATTCCC
13051 AATCCATATA TGAGAAAACT GAGCCAAAAA TAGGCTAAGG AGCCTCCCTA
13101 AGGTCATACA ATGAGGCAGG GGAGGAGGCT GATTAGAACT TCTGAATTGC
13151 CAATGACCAC AAATAGTCTA GGGTAGGCCT GGTTGACAGA AAGTCTGCCA
13201 TTGAACACCA TCATATCACA TGACAAATAC AGCAAATTCA TTGTGCATAG
13251 TTACGTCTTT ATAAAACAAA ATAATGCCAG GATAATGGTA TGTGATCAGC
13301 ATTACAATTC CAAAGATACC AAGACAACTA CTTATCTGAC ACTTGTCTTA
13351 GTATTTCTCT AACATTTATC TAAAATTATT TCAATTATTT CTTTTCTCGG
13401 AATGCATAAC TTGACTCATT GACTTGATTT ATGATTCTCA GATCAAAGGA
13451 AATGTAACAA CAGGGACTAG AAACACTTTT TTATTCAATG TCCAATGAGG
13501 GTTGGGGAGG ACTCCATCAT TGACTCATTA TATAATTCCT CATAAACTCA
13551 TTACAATTGG CCTGGCTTTC ATTAATTCAT GAGCACTTAT TGAGCACCAC
13601 ATGCCAGGCC TGTGCTAGTG CTGGAGATGC AAAGACAAGG GCAAGTTCAA
13651 TCCATGCCCT CAATGAGTTT ACAGCCTAAA GACGACTTTG ACTACCAGGC
13701 CTTCATTACA TAGAGCGACA TCCTAGGACT TGGAGAATCA GCTTTCCTCT
```

FIGURE 3E

```
13751 GGAGCCTTAA AGACATCCCT ATTTACTTTT GTGTCTTTTC TTTGAAGAAA
13801 AACAAAAATA AGTATACATA GGATACATTA ATAATAAAAA AACAGTATTT
13851 TATGAGACTC AGAATGCTAA TTTTAGGATC TTTGCCCTTC TCAGTTGACT
13901 TTTGTGTCCC TCAACTGTTT AGTCTGCAGG ACAGATATCA CATCCTGCTG
13951 TGCAGTTTAT AAAATGTCCT TAAAATTAGA AGAAAGAAAG GCCTTGTCTT
14001 CCTGGGTTTA AGACCCACAC ATCTGAGGCT GTAGGCATTT CAGATCCCTC
14051 TGGTGGATGG ACCAAAATGA TAAACAATAC TGTGAGATAA ATGCTTTAAA
14101 CATCATCTGC TCTTTCATCT GAATTCCCTA TTCATTATTC GGCAACATTC
14151 ACAGTTTTCA TATAACGATT TCAGTAGTTC TAGGGCACCA GAAAAGCAGT
14201 ACTAGGAATG GCCATAAAGC ATAGAATATT TATAATCTAA TGAGGGAGAC
14251 AACTAAAAGA AAGAAGGAAT AAAAGCATCT TCAACAGAAA CACCCTTTAC
14301 CAACCAACTA GAGGTATAGA AATGATATTA GGTAATTAGT GACCACTAAT
14351 TTAAAGATAA ATATTTATTG AGTGCCAGAC ATTGTTCCAG GCACTGAGTA
14401 TATAGCAATA AGCAAAAAAA ACAAAACAAA ACAAAACAAA AGTGCCCACT
14451 CTCAATGGAG TTTATATTCT CAATTGTGGA GACAGACAAT AAACAAATAT
14501 TTATATATAA AATGTCAGAT GGTGGTGACA GGCACTATGG AAAAGAATAA
14551 AGCAGGGCCC AGAGAGAGAG GGTAGGATGG GGTAGAGGTG GGATGGGGTG
14601 GAGGGCTGCT GAGGTGGGAT GGAGTAGAGG GCTGCTATCT CACCTAGAAT
14651 GGTCAAGGAA GTCTGCACCT ATATGTATCA CTTGAGCGGA GGCTCTGAAG
14701 AAAGTGAGGG AGGATGAAGG CAGAGAGGTG AGAAGAGAGG ATTACAGGAA
14751 AAGACATTGG CAAGTGTAAA ATCCTGGGGT GGAAATGTGT TTGCAAGTGT
14801 GTCTAAGGAA CAGCTAGGAG GCCAGTGAGG CTAAAGCCAA GTGAGCAAAG
14851 ATGGGAGTGT GAGGAGATGA CAGGTCACGA TGGGCACAGC CAACAGTAGG
14901 GTGGGCAGGA AATCGCAAGT CCTTTGAATT TACTCTGCAG GAGATGAGAG
14951 GCCACTGGAG GGTTTGGAAC CAGGAGGCAC ATGCCCTAAC TCATTTGAGA
15001 AGGATAGCAG TGTCTGGCTG TCCTGTGAAG AAGTGGCCAT AGGAGGAAAG
15051 CAGGGAAGCA GGCATTTGCA ATAATTCAGC CAACATATGA TAGTGGCTTG
15101 GTCCAGGGTG CTGGCAGAAG ATATGGCAAG GGAGGGGTTC TGGACAATTT
15151 GGAAGGTAAT GCCAATAGAT TTGTATGTGA TAAAAAGTTG AGAGGACTTG
15201 ACGTGTACGA GTGGTTAATC TTCATAAAAT GGATGAATGG TTAAAAAGAT
15251 TTCCGCAAAG AAACTGTGGG TTGAAGGTAA AACTAGTAAC TCCAATGTAA
15301 GTGAACAACA GAGAAATACA AAACAGACAT TTTTCCTACT CCTACAAAAA
15351 CTGTAATTAT CAAGAAGACG ACATGAAGTT TATACCCAGT ATTGTTAGCA
15401 GGAAGCCTCA TTCCAAGTAG ATATTTTTCC TTGGCCATTT TAGCAAGTGA
15451 GAGCATGAGG CCATCATAAT GAACAAATCA TGCCATCATG ATTTAAAAAG
15501 AAGCATCTGG AGTTTTAGTA ATATAGTTAG GTGAGACTAA AATTATACTA
15551 AACATAAAAT TAAAATATCT TAACAATATT CTTAGCAATT TCAGCTTTAC
15601 CATATCCTTT TGAAATCTAA TTTTGCTATA TGCTTTGTAA CATAGGGGTG
15651 GGGGAAAGAG AGAAATTTAT GAGATAATTT ATAAATAAAA ATACACCTAA
15701 AGTATAAGCA TTCTCAACTG ATGGTCAGAA AATATGGAAG GTATTCAAAA
15751 CTCTAGCAGA AACATACCAT AAACAAGATT TTAAGACTGA AAGTAGACGT
15801 TTAGTGGGGT TCAGGGTGAA AGGCAGGGGC AAGAAGCTGG CAAGAAGAGG
15851 GAAGGGATAC TAATTCTAAT TTGCCTCTGT AATGCTTTAC ATTTACCAAG
15901 GTTCCACAAA TGGTATCTGA TTCCATCCTC ATATCAACCC TATGAAGTAA
15951 GTCAGAAAAG ACGATGTCTC TTTTCCTAAG GAATGAATTG AGACTTAGGT
16001 TGAGATACTC TCCAGAGCTT ACTCAGATAG GAAGTGACAG GGCCAGGATT
16051 CATATTAGGG CTTCTGGCTC CACAGACAGT TCTCCTTAAG ACTTTCAATA
16101 AATATGTTTG ACAAATTAAG TGCTTACTCT CGGCTGAGTG TGGTACTAGG
16151 TGGTGTGGCA GCATCTCAAA AAGGGGGAAA GTCACTCCCT CAATTCCCAT
16201 GTGGCCTTCA GTCTGAGACT AGGGAGATTA AACAGATGCC TGAGAAGCTG
16251 TTTATTACAT TTACAAAGCA ACACATTTGT CAAAGTGAAA TAATAAATTT
16301 AGCCCATAAG GACTCTGGGG GCAAAAAGTA AAAATTAAGG CATTAGTCAT
16351 TACAGCAAAT AAGGTTAACA GGTGTGATGG AGCTCCTTCG GCGTAAGTCA
16401 GCTTAAATTG ACAAGTAAAG AGAGAAATTC ACTGGCTCAC AGATCTGATA
16451 ACTACAGGCT GGTAGGGCAT AAGCAATATC ATCAGGAAGC CGTGTCTCTC
```

FIGURE 3F

16501 ATTACCCAAC ACTGGTTTGC TGTGCATTCA TTTTATTCCC AGGCATGTTG
16551 TCACCAGGTG TTGGTAATCT GACCCCAGCA ACTCCTGGCT AAATCCCACA
16601 GGTTTAGCTC TCACAATAGA AAAGAAAGCA CTTCTTTTCT AATGGCACCA
16651 GCAAAACAGG GTCTGCCAAA CTTGGGTTTT GTGCCTGTCT CTGAACCAAT
16701 CACTAGGGTA TAGGGGAGTG CCGTGCTCTG ATGGCCAGCC CTGGGTCATA
16751 TGCCCATTCT TGGGTAGAGG CCGGGTCAGT TCCACCAGAT GAGCATGGTC
16801 TGAGGAAGAA GACGGTTGTT TTTCCAGGGG AAAATAGAAG TGCCCCCGCT
16851 AGAAGGGAGA ATGGCTGTCA GGAGGGCAAA ACGACAGATT CACTAAAATA
16901 GGTTGATGCC TAAAGAAAAT AATTTTATTC CTAAATTTAA GGGAGTATTT
16951 CAGTTGTTTT TAATCTTATG GAATTCTACA CTGGGAGGGA GTTGGTGCAG
17001 GAGATTCATG ATATGCAGGC ATAGGCTACA GAATAATGCT TTGAGTTTTT
17051 ATCCTTTACT TTTCCTTTCC TTTAAGCTTT AAAGACACGA TTTCTTCATG
17101 CAGGGTTGCC CTGAGGTGAG CCTCATCATC TCTTTTTTTT GAGATGGAGT
17151 CTCGCTCTGT CACCCAGGCC AGAGTGCAGT GGTGCAATCT TGGCTCACTG
17201 CAACCTCCAC CTCCCAGGTT CAAGTGATTC TCTTGCCTCA GCTTCCCGAG
17251 TGGCTGGGAT TACAGGTGTG CACCACCAGG CCCCACCACG CCCGGCTAAT
17301 TTTTGTATTT TTAGTAGAGA CGGGGTTTCA CCGCGTTGGC CAGGCTGGTC
17351 TCAAACTCCT GACCTCAGGT GATCCACCCA CCTCGGCCTC CCTGAGTGCT
17401 GGGATCACAA GCATGCGCTA CCACGCCCGG CCTCATGGTC TCTTTATTGT
17451 ACCTTTTCTA GTCTCTGCTT TCCTGAAGCC AGAGGTCTTC CTATCTCCAG
17501 AAGCTCCAAA GACACACTTT CAAACCCCTC CCAGTCACTT GGCCTTTTCT
17551 GATGACTTCT TTCCTTCAAG GCTGCCTTTA GTAACCGATT ATTGAAGAGG
17601 CAAGAGAAAG CCCTCAGCCT TCTCCACTTT CACCTCCCTG GGCTCCCCAA
17651 GTTTGGCCGA CTCCTCTTTT CAAGTTCACA TTTTCTCCTT TCCACAGAGG
17701 TTTGCAACAT TACCTTTAAG AAATCATCTC CAGTCTCTAT CACGTTTCAA
17751 CAGTTCTTTA CCCCATGCTT TTATCCCTGT CTCCCACCAA TCATATCCAC
17801 CGGCCCTATT GACCGCTTGT GGGAGTTAGA ATTTTGGAGA CTGGTCATAT
17851 GTCACAAAGT CCTGCTCTAG AAGGCAGAAC ACTCCATTTC CTGCTCCTCC
17901 AAAGCCCTTT ATCTCTCCAG GCCTCTCCTC CTGTAGCTCT GAAGCTGGAT
17951 TGATGAGATT CCCAGAGGGG AGCATTTAGT GCTCTGAGTG CTTTGATGAA
18001 ATTGATTAGG TAAATGGAAA CATATTTTTT GCAACCACTC TAGCCTGTAG
18051 AAACAATAAG TTGCAATGAT TTGCCATTTT TGAAATAATG AAGGTTCTTT
18101 GTAATTTTAA ATATTCTTTT GCCACAAGAG ATTGTTTTCC AGCAGTAAAA
18151 TAACCAGAAT GTTTGATTTG AAATGTTGAA AAAATATATA CCGTCTGATA
18201 TCTTTAGAGC AGCACTTTCA TTATCAATGA TGGATTTAAC ATTTTGTTTA
18251 ATTTTTCTAG CTTCTCTCCT GAAGGGTTTG AAACATGCCA ATATTGTGCT
18301 CCTGCATGAC ATAATCCACA CCAAAGAGAC ACTGACATTC GTTTTTGAAT
18351 ACATGGTGAG TTGTTCGAGC ATTTTACAAC ACTTGAGAAA AATAACCTGG
18401 TACTTGTATA ATGAATCTGT TAATATTTTA TGGCATGATA AAACTTTTAT
18451 TATAATGTGA AAAGTATCAT GGAAATTTTC ATTATTGTGA TTAGTAGAAC
18501 CTTATTGTTC CCACATCCAT CTTTGGTCCT GCTTCCTTAC CCATGACTTT
18551 TGCTGTCCCT TTTCCCCTCA TCAGCAATAA TAAATGAGGA TCTTGAGTTT
18601 ACCTTCTAAA TAAAACTTTT GCACTTATTT TTAATCTAAT TTTAATCACT
18651 ATCTGAGCAG AATCCAACAT TTTTTCATTG ACAATAAAGG TAAAAATCAC
18701 AAGATATTTA AAAATTGTAT GCAAGCTTGC TAAAGAATAA CTCATGTTGT
18751 ATTTTTGGAA GAAAAAATAT TTAAATAAGC AGAAAGAACT TATAAGGTAT
18801 GTGTACTTGA CTTGCCTCCA AGGACACTTG GAGAGTGAAA AATTCCTGCG
18851 TCGTTGTGTT CAGTGCCAGT CATTTAAAAT GAGCATCTCT GTGCTGAGAA
18901 ACAGGCTTTG TTCTAAGAGC AGCCAGTTAG AAAGACACAC TGTGTTTGAC
18951 CTTAACAGTG GGTTCTCAGA AAACCTGGTT ATATTCCTTT TGCACCTTAT
19001 TCTTAAAATT CTGTACTTCG TGATACCTTC TGACAGTCAA GTCAATGTTC
19051 TGCTTTAGGA TGCTATCTAA GCACCACTAA ATTCACTCAC TTCTCTTTCT
19101 CCGCTGTTTT ATTTAGCACA CAGACCTGGC CCAGTATATG TCTCAGCATC
19151 CAGGAGGGCT TCATCCTCAT AATGTCAGAG TGAGTACGTT AAGGGTCAGG
19201 ACCCTCTCCT GGCTTGCCCA CAGAAGGAGA ATTCTGAAAC AGACTGTCTC

FIGURE 3G

```
19251 ACAAAGCAAA GTCCTATGAT ACTAAATAAG AGGATGGACA TCACTGATAT
19301 TCCAGAAAAA AGTTTTGTTT TGTTTTCGTT TTTGTTTTTT TTTAAAAAGG
19351 AAAGAAAAAA GAAAAAGAGT TGCTGAGTTG CTTCTTAAGA TATGGAGCAA
19401 TGTTTTCTGA GCAACCTAAT GCTGTCAGTC ATGGCTACAT GCAAATGTGC
19451 CTTTAGATGA ATAAACGAGT GAAGGAGAAT TATACTAAAA GGAAAAAAGT
19501 AAAGCTAGGC CATCAAAAAA TAAATACCTT CTTCATATCA GATTACTGTG
19551 GTCTAAGGTG AAGTCTGCAA TACTTGTACT AGCAGATCCT ATTATATATG
19601 TGGCCCTAAC TCCCATTTTT CCAGTCATTA GAATCAAAAT AATAAACTCT
19651 TAATTAGCTA TAATTCTACA TCTGTTATAA ATTTTAGAAA CCATTTATAT
19701 TTCATACTTT TCATTCCCTA AGGTTTTATT GGCATTAATT AATTGATTGG
19751 CTCTTAAAAT AACCGTATGA AATTTGTATA TGATGTATTT ATTCATTTAA
19801 CTAATATTTA TTTATGTATT CATTTATTCA TTCATTTAAG AAATATTTAT
19851 TGAGTACTTA TTGCGTAATA AGTTCTGGGG TTTCAATAAT GAATAAGTTC
19901 TGTTTCTTAT TTTCAATGAG CTTAAAGTCC AGTAAGATAT ATGAACTTAA
19951 ATAGGCAGTG AGGGCCAGTC TTCAAGCAAC AGCAATGCAA GATGGCAGCC
20001 ACCATGGGCT CAGGCAATTT ATGAAAGCCA AATATACAGC CTTAAAATAG
20051 AATGTGGACC TAAATACCCA GAAGAACTCC CCTTTGTAAG ATTTGTAACA
20101 AAAATTAATA TGAGTAGAGT TAATAGTTCT AATGGAATGG TGAACCCAAG
20151 AGCCATATCA GCGCTAGCAA AATGGCAGAA TTCATATATC ATCAAAGTTA
20201 TCCTTCAAGA GCTTCAGCGC CTAATGATGT CTAAAGAAAA TGTGAAACGC
20251 CCTCAGCCAT CTGAAGGACA GTGTTACAGC AATTGATCAA AAAGAAAAAC
20301 CACAGGCCCT TCCCCTTCCC CCATACTTGA TGTAAGCAGT CTTCATTTTC
20351 CATAGTAGTA AATTTTCTAG ATACAGCTTG TAGAGCTCAA AGTACTGGAA
20401 AGAAAGCTCC CATTCAAAGG AAATTTATCT TAAGATACTG TAAATGATAC
20451 TAATTTTTGT ACATTTGGAA TATATAAGTT GTTAGCCTGG CGCGGTGGCT
20501 CACGCCTGTA ATCCCAGCCC TTTGGGAGGC CAGAGTGGGC AGATCATGAG
20551 GTCAGGAGTT TGAGACCAGC CTAGCCAACA TGGTGAAACC CCGTCTCTAC
20601 TAAAGATACA AAAAATTAGC CAGGTGTGGT GGCGCACACC TGTAACCCCA
20651 GCTGCTCGAG AGAGTGAGGC AGGAGAATTG CTTGAACCCA GGAGGCAGAG
20701 GTGCAGCGAG CAAAGATCAC ACCAATGCAC TGTAGCCTGG ATGACAGGGC
20751 AAGACTCCAA CTCAAAAAAA AAAAAAAAAA AGAAATATGT AAGTTGTGCT
20801 ATAACAAATA AATAGGCAGT GAGAAGCAAA GTGCTAAAGC CTATGACCAT
20851 GGTAACTAGG AATACTGTGG GAACACATAA TAAGGGAACC TAACCCAGTC
20901 CTGGAAGTAA GGTTTTGGAA AGGAATGTTT GAGGACAAAG GGTTAAAGAG
20951 AGTGAAAAAA AAAATTAAAA TACCAGTTTA GCTGTGTGGA GAATGGGATA
21001 GGGAGCTAAC TAGAGAAATC AAATAGGAAT GTTTCATGGT ATGTTAAGGA
21051 CCCTGGTAAG GGTGAAGACC ATTACATTAT CTGCACCATC GCGGGACTTT
21101 TTTTTTATGG TAATGCTTGG CAATTTAAAT AGAGGAGCAG AGAATGTAGA
21151 CAGTTGGATT GAGTCAGAGT TGAAGTTCTG CCAGACATGT GAAAGGAAGA
21201 GACAGGTAGG CAAGAGAGTT GAAGAGATTA TCAAGACAGA AGTTAATGTG
21251 CTGGCCAGTG GCATCTAGTC TGAGTCTAAT CTGAGGGAAG GAAGTGAAGA
21301 TAAGCAGCTT GCTGATAGTT ATGAAGAGAG TGGAAGGCTT CAAGGACCTA
21351 CAGGTGTTGA TTAAATAGAA GAATGATTGG AGAAAGAATA ACTGTGAGAG
21401 AGTGAGATTT TCAGGCTTGA GTGACTCTCA CATACCAGAC ACTGTGCTAA
21451 ATGCTTCAAA GACATGATCC CTGCCCTCAA GGGACTTACA GCCAAAAACA
21501 AGAGATAAGA AATACACACC AATACTATTA TAGGACACTT GTGTAGAATA
21551 TCAAGAAAGA AATACGATCT AGTACTGTAG ATGTGCAACG GCATCAAAGA
21601 TATCTTCTAG TTTCAAGAAG TTTCAGATCG GCCGGGCGCG GTGGCTCACG
21651 CCTGTAATCC CAGCACTTTG GGAGGCCGAG GCGGGTGGAT CACAAGGTCA
21701 GGAGATCAAG ACCATCCTGG TTAACACGGT GAAACCCCGT CTCTACAAAA
21751 AATATAAAAA ATTAGCCAGG CGTGGTGGCG GGCGCCTGTA GTCCCAGCTA
21801 CTCAGGAGGC TGAGGCAGGA GAATGGCGTG AACCCGGGAG GTAGAGTTTG
21851 CGTGAGCCGA GATCGCGCCA CTGCGCTCCA GCCTGGGCGA CAGAGTGAGA
21901 CTGCGTCTCA AAAAAAAAAA AAAAAAAAAA AAAGTTTCAG ATCTTAAACA
21951 CACTGCATTT CAACAGTCTA GAATAGGAGA GCATGTTACA GGGAGAGAAA
```

FIGURE 3H

```
22001 ATGTTTTCAG CAAAGGTACA GAGTAGGGAA ATAGAGGATA TGTTCAAGGA
22051 AGAGGACCCC AGAGTCATGG TTTGTTAGGG TTAGAGGAAA CACAGTGTTT
22101 TGCAATCTCC AGGTTCCATT AGTGCGTTAT GAAATCAATA TGGTGGTTAG
22151 CAACCTGCAT TTTAAAAAAT GAAATAAATG GATGAGAAGA GAATAGAAAA
22201 TATTAGCATG CATTACATTT TGAAAGAGCA AGTATTATTT TCTGCAACTT
22251 TTGCTCCAAT TGTAACTGTA CTTATATTTT TATGTATGGA TGTGAATACC
22301 AGATACATAT ATATTTCTTA CTGTAGACTG CAGTCAAAAA ATCTTTAAAG
22351 CACTGGCCTG GTCTAACTTC CTTATTTTGC AGAGGAGAAA TCCAAGATCT
22401 GAGAGGACAA ACATTTTGCC TGAGGTTATA GAACCAGCTT ATGCCATTGC
22451 TAAAAGTGAT TCTTAGTTAA AATTCTTTCC CACTAGTGCC ATACTGCACT
22501 TCTAGTTCTG TTGGCCTGAA ATACAGAATA TATTAGTGAA ACAGCATACA
22551 CAAGTCTGGG GAAATATATT GGGTAGGTGG CTGAGAGCCT CATTTTCTAA
22601 GAAATGTGGA CCTTAGGCAG GGTATGGTGG CTCACACCTA TAATTCCAGC
22651 ACTTTGGGAG GCCAAGTCAA GAAGATCGCT TGAACCCAAG AGTTCAAGAC
22701 TAGCATGGGC AACATAGCAA GACCTCATCT CTACAAAAAA TTTAAAAATC
22751 AGCTGAGCAT GGTGGCATAC GCCTGTAGTC CCACCTACCT GGGAAGCTAG
22801 GTGGGTGGAT CGCTTGACAC AGGAGTTTGA GGCTAAGGTG AGCCATGATC
22851 ACACAACTGC ACTCCAGCTT GAGTGACAGA GGAAGACCCT GTCCCTAAAA
22901 AAGAAAGAAA TGTGGATTTT ATTCCTTAGA CAGTACAGTC ATTAGTCATT
22951 AAGTTTGAGT TGAGAGAAAA TAATATGATC AGAAGAAATT TATATCACTG
23001 TGGTCTGTAG GATATATGAA AGGAAATAAG AGACTAGAGT CAGGGATTCC
23051 ACTTAAGTGT TTGTTTGTTT GTTTTGAGAC AGAGTCTCTT TTTGTTACCC
23101 AGGCTAGAGT GCAATGGTGC AGTCATGGCT CACCGCAGCC TCAAACTCCC
23151 AGCCTCAAAT TATCTTCCCA GCTCGGCCTC CCAAAGTGCT GGAATTACAG
23201 GTGTGAGCCA AAGGGTTTAT TGATGTGGTC TGGCCTAGTG CCTCTCAAAC
23251 TTCAGTGAGC AGACAAGTGA CCGGGAACCT GACTCAACAA GTCTGGGTTT
23301 AAGCCTGAGC CTCTGCATTC TAACATGAGT CAAGCTGATG CAGATGGTGC
23351 TGGTCAAGAG CCAAGCACTG AGCAGCAAGG ATCTAGTTAG CAATTAGTAA
23401 TCAAGGTTGA TATTATGGTA GTGACAATAA GAATGGAGAG GAATGTGAAA
23451 ATCAGTAACA AAGAAGAGTT CACCTCTTGG TAATGTGAGC ATGAGGAGGG
23501 AAAGGATGGG GCCAAACATA ACTGGTTTTG TGTTTGACTG ACGAGGAGAA
23551 TTGTAGCTCT ATTAACAGAA ATAGGAGAAG AAGTTGGTTT GGAGAGAAAG
23601 AGGAGTCCTG TTTCAGACGT GTTGAGGTCC CAGGTGAGAC AGGATCTCCA
23651 AAGGGAAATG AGCAGTAGGC AACCTAAAAG GAAATCTGTG CTCAGAAGGG
23701 AGCTGTGAGC TCGACGTGTA GATCTGAGGG TCATCAGCAC ATAGAGTTTA
23751 GAAGACAAGG AGTAGGCAAC CAAAAGAGCA AATACACAAA GAGAGGAGGA
23801 CTGATGATGA GACTTTTGCC TTTTAGGATG AGAAGAGGAA CAGGAAATGA
23851 AGGAATGAAG GGAAGCAGCT TGTAGGAATG TAGAGCATCT GAAAAAAAAA
23901 TACACACTGT CATGGAAGTC AAGGGAAGAA GAATTTCAAG AAGGAGGGTA
23951 TGGTGGACAG TATTACAAGC ATCAGGAATA CAGCTAAAAG TCATACTCTT
24001 GACTGCATTG ACCTTGTGGA TTTGTGAGGG ACACACTAAT AAATAAAGGA
24051 ATTTATTGTG GGTATATGGA GGCACAAAGG AAGAGGTTAT CCAAATCAAA
24101 GCAGGTGGGA GTAGGGATGA GTTCTCCAAG GTGGAGGCAT CAGTGAATGT
24151 GGGAAGGGGC ACAGAGCATC CATGCCCATC CCAGGCAAGC CACCCTCCAG
24201 AAGCCTCCAT GAGAGTTCAG CTATCCAGAA GGTCTCTGTA CCCTAATCTT
24251 TCTGGGTTTT GCATAGGCTT CATTGTGTAG GCATGATTTA TTAAACTATT
24301 GGCCACTGGT GATCAACTTA ACCTTCAACC CCTCTCCCCT CCCTAATCAT
24351 GCCTTGGTCT TTCCAGTGAC CAGTCCCTAT CCTAAGCTAC CCAATGGTCT
24401 GCCAGCTATC AGTCAACTCT ACAAAAAGAC ATCACTTTGG AGATTCTAAG
24451 GATTTTAGGA GTTGGCTGTC AGGAATTTAG TTGAAGATCA AATATATATT
24501 TCACAATATC ACAGTCGTGC TATTTTATAT CAGGCGCCAT TAAATGGTTT
24551 TAAACAAAGA GGTGATAAAT TCAGATTTTC TTTTTATAAA GCTTACACTG
24601 ATGACAGTGT GGTGAATAGA TTGGGATGAG GGCAATACTT TTTTTTTGAA
24651 ATGTTATATT CCCCTGACCC TACTTTCTCC TTGTTTTCTT CTACCTCTCT
24701 CCCCCTACTC ACACAGAAAA CTTCTCTCCC TCTACTCATT CCCTGAATGC
```

FIGURE 3I

```
24751 TGGTGTCTGT TAAGGTTCCA GCCTTGACAG TGAGGCTAAT CAGAACCACA
24801 GTGGTACAGA TGTGAGATGA TGGTGGGAGA AAGTGGACAG ATATGAGACC
24851 AATTACTTAG CCGGAACTGA CGGGAAAAAC AAGAGTCAGC GATATTTTTT
24901 TCTGGATCTG AGTATTAAAA TGGATGATGG TGCCATTCAC TGTGATAGAG
24951 AATCAGAAAG AAAAATTTAT TTTGGAGAGA TACCATGAAT TGTGTTTTAG
25001 ACATGCTAAG TTTGAGGTGA TTATGGGATG TACAGGCGAG CTCCAGACTG
25051 TGTGGGCCTA AAGTAGAAAG GCAATCTGAG TTGGAGATAA AGATTTTGAA
25101 ATCATCAGAA TACGGTTGTT CATTAGAGCA CTGTCAGTGG GTAAGATAGC
25151 TAAGGGAGCA TGTGTAGAGT GATAACAGAA GATCAAAGAC GGAACCCTAA
25201 GAATAACAAT ATGTTATTAT TTATTATTTT ATTATGTTTT ATTTTTTAAT
25251 TTTATTTTTA TTTATTTATT TATTTTTAGA CGGGAGTCTC GCTCTGCTGC
25301 CCAGGCTGGA GTGCAGTGGC GCAAACTCAG CTCACTGCAA CCTCCGCTTC
25351 CTGGGTTCAA GGGAGCCTCC TGCCTCAGCC TCTCAAGTAG CTGGGACTAC
25401 AGGCACCCAC CACCTCACCT GACTAATTTT TGTATTTTTA GTAGAGACGG
25451 GGTTTCACCA TGTTGGCCAG GCTGGTCTTG AACTTCTGAC CTTGAGTGAT
25501 TCACCTGCCT TGGCCTTCCA AAGTGCTGGG ATTACAGGTA TGAGCCACTG
25551 TGCCTGGCCT ATTTTTGTTT TTTATAGAGA TGGGGTCTTG CTATGTTGCC
25601 CAGGCTGGTC TCGAACTCCT GGACTCAAGC AATCCTCCTG CCTTGGCCTC
25651 TCAAAGTTCT GGGATTACAC ATGTGAGTCC CTGCGCCTGG CCAGAATATC
25701 AATATATTAG ATTTTAGTAG AAGTAGAACC TATGAAAAGA ACAGCCAGAG
25751 GGGCAGAAGA AAAATTAGGA GATTGTGGAA CCAAAAGAAG AGAGTGCCTC
25801 AGGAAGGAAG GCATGGTCTA TGATGCCAAA TGCTGCAAAG ATAAGGAATA
25851 AGAAGTATCC ATTGGGTTTC ATAGGAAAAG TCATGGGAAA CCATGGTAAA
25901 AAAACATTGT GAATGACACA ATCGTTGCAA AAGCATTTTT ATAGGGGGAT
25951 GAATTTTGTA TTTCAGAGGA CAAACAGTTC CATACAATGG CAAGATCTAG
26001 TGTGTGACCA CGGGAGTTAG TGTCTGAAGT GGATTGGAGA AGCAGATCAT
26051 TGGAGCTGAG GTTGGCTAGA GCTGTTCTCA TGGACACTAA TGTCATGGAG
26101 TCAACAGCTG TGATCCAAGT GCCCACATCT TCAGTGAATG ACAGAGAGGG
26151 ATTGAGAGTT CAGTGAATGA CCGCTAAAAG AAGAGTAATG GAAGATGTGG
26201 CTGGATGGCA TTAAAATCCA AGGGACAGGG GTTTTTACTT AAAAGTAGAG
26251 AAGTAATGGT TTTGAAGTGG TAGTGGGGAA AAGGGAGGCA GCTTATGACA
26301 CTTGTCAGTG GTCAAAGGTA TGAGGAAGTT ATAGAAAAAC TAACATCCAC
26351 TTGAGAATAT TATAGGGAAG CAGTGAGCTC AAGGTCTCAT TTAAGGAAAG
26401 GAGCCAAAAG GAAATTCACC AGAGGTTAGC TTTTAGGTAG TTTTTAAAGC
26451 AGGATTGAAG AATGGAGACT AAACAGTGAA AATGTTTGGG AGAGAGAGGA
26501 GCAATAGATA TGAGGCTAAA CAGAGGAAGC ACAGAACAGA ATGGAGATGA
26551 GTATGTTGGG AGGAAAAGGA ATAGTCAGAG GCTTATATTT TGAGTTGTGA
26601 CCAAGGAAGA CAGGGTGGGA ATCCTCGTGA GGTTATCTTG TTTCAGATTT
26651 CTAGTAGAAT GAGTCCCAGG GATTCCAGGG GGGATGGAAG GACTCAGGCT
26701 TCCCTATAAG GAGTTGGCTA ACGGATCTCA TTGGTTTTTG AGTAACTCCT
26751 GGCCCAGATG GCACTAGTTC AATGGAATTA TTTTGTTCCC CCAAAACTTA
26801 TTGAGTTGGA AACAGGTCTA ACTCCTGGGA TCTGGGAAGC CTTTCTGGAA
26851 AGAGTCACCC ACGATCTGGC TGATGTTGAA CTGTGCAGAC ACCATCATAT
26901 TTGGTTATGT TAGGATGCAA TAATTGGTGA AGCTTCTGTA GTGTTGAATG
26951 AAGAATCCAG GTTGGAAGGG ATGAAAGGGT GAGTGGGTGA TGAGGTTTGT
27001 CAGCACAGAC TGCAATTTTG AGAAATGTGG TTATAAAATA CCATACCTTA
27051 ATACCGCAGT GCTTTACCAC TCACAAATGC CTGTAGACGT ATCTGGCAGA
27101 GAGGAAAGGG GTTGAATGGC AAGAATGTGG GAAGGGACTG TGGCTAGTTA
27151 GTGAAAATAG TCTACACTTG GGACATAAAA GGCATTTCAA GCTGACCTAC
27201 TAAGAAGCTC TGTCTCTGAC TCAGCCAGCT GGCTCTCTCC TTCCCTGTCA
27251 TGTTTTCATT TTCTGTCTTT TCTCTAGTTT CTCAGGATGG TATAGTGGAG
27301 TCAGACAAGT CTGAATTTGA GTCTTGGCTC TGACTATTCC TAGACATGTT
27351 TTAAAAGTTA CATTGAGCCC TGGTTTTCTC TGTAAACTGA GGATAAGCAT
27401 GCTATCCCAA AGGTTGTATC CCTCACTGGT CACCAGCTTC CTGTCTTCTA
27451 TCCACCTGTC TTCCTCTTCC TCTTTCCCTA GTCCTGCATA TTGAAAAACA
```

FIGURE 3J

```
27501 TTTTTTTTTT TTTTTGAGAT GGAGTCTTGC TCTGCCACCC AGGCTGGAGT
27551 GCAGAGGCAC GATCCTGGCT CACTGCAACC TCTGCCTTCC AGGTTCAAGC
27601 AATTCTCCTG CCTCAGCCTC CCGAGTAGCT GGGATTATAA GCATATACCA
27651 CCACATCTGG CTAATTTTTG TATTTTTAGT AGAGATGGAG TTTCACCACA
27701 TTGGCCAGGC TGGTCTCGAA CTCCTGACCT CAGGTGATCG GCTCGCTTTG
27751 GCCTTCCAAA GTGCTGGGAT TATAGGCGTG GGCCACTGCG CCAGTCTGAA
27801 AAACGTATTT TTAAGCACAT ACTATCGTAT CTTCTTGTCT TTTACCTGGA
27851 ATTTAAGCTG GTTGTTTGTA TTACCTTTTC CATGGACATT TATATTTATA
27901 ACCAATCAGA AGGTTTAAAT GTCAGTGTAG GAATTTTGTG CTATGGAAGC
27951 TTCGTGGCTT GGTGAATGGT AAAATGAATA ATGTGTGTAT ATTTGAAGCA
28001 TCAGAAAGAG AAAATGCTGG GAAGATTCAT AGAACCAGTT AACATTTGAA
28051 CTAGGAGTCA TAAGAAATTT TTAAAATTCT TAAATGGTTT ATGAACCTGA
28101 TGTGGTAGCT ACATGAAACC TGCATAGCTG CAGGTATGCT ATGGTAGGTA
28151 AACTCTCCAT GCTCCTGCTT CCATTGGACC ATTTGGCTCC AATGTCTCCA
28201 GGTCTTTGTT AGATCAATAC TGGTCCTAGC ATCTCTGAAA GTCCTAGCTT
28251 TCTAAGATGC TGTTGAAAAA GAGGATTAAT CCACATAACT CTGCATCTGC
28301 CATTTTGCCC ATGTCCCAGG AATGCTGGGC CTAGCCCTTC CTTTCTGAAC
28351 TGCCAGAACA CGTTCTCAGT TGACATACGT CTTTGTAAAT ACTGATGTTG
28401 GTGTTTGAAT TCTCAATTGC CAATGGCACT GGAAAATAGC AAAAGATACT
28451 TGGAATACTA AGCATTCTTT TTTTCCCGTA AGTTTCTGTA GTGATGGGAA
28501 CCTAGTAATG GCTTTGGTTT CTGTGCCTCA TAACCACATG AAACATTTTT
28551 AATTTGGGGC TCAGAATGTG TTTTTCCCTT TTATTTCTCC ACCACTACCA
28601 TTTACCCTTT CTCCCTTCTT CCTCCTACAA TTTGTTCCTT ATTCTTTTTT
28651 GATTTTTTTT GAGGGGGGGG GGTCTAACTT ATTTTGGTCT CTCTTCCCTT
28701 TTCATCTGTA CTGTGTATTT CCCTTGTTTT CAACTTTGAA TTTAAGACTT
28751 TAAAAATAGC TTTAAAAAGA TAAAGATTTC TTTATTTTCT AATACCATCT
28801 AAAGATATAT TTTTTAGTGT GGTCTCCTTG TGTTGTGTTT TTAAAAGGGT
28851 TTCATATTGG AGAGCCTGGA AAACTTAAGC AGTTGTAAAC TTTAGAATAT
28901 CATTTCCAGG TCAACTTTGA TCTTATATGC CAAGTTCATC GGTGGGGAAA
28951 AAAATTAAAT CTTTCACATC TAAATCAATA ACTAGTGTTC CAAAGGAAAC
29001 TTCAAAGTTT CACTTTAGAT TTTTAAAGAA GGGTAATTCC TTCAGTATCA
29051 AAGAAATGAG ATGTCAGGAA AAGCCAGAAT CCCTTTGTTT AGGACACAGT
29101 CTAGTTACTT GACTTTTCTT GTCCTTTTTC TTCCCCCTCT GAATGTAAAA
29151 ATCTTCTTCT TCTTCTTTTT TTTTTTTTTT TTGGTCTCTC AAGAGACACT
29201 TTTACTATAT TCTTTGAGAT GACTGTTTTT GATTTAGAGG CGAAATCAGC
29251 ACGTGGTGGC TCAAATCTCC TTATGGATAG TGTTTCTTCC TTCCAGCTTT
29301 TCATGTTTCA ACTTTTGCGG GGCCTGGCGT ACATCCACCA CCAACACGTT
29351 CTTCACAGGG ACCTGAAACC TCAGAACTTA CTCATCAGTC ACCTGGGAGA
29401 GCTCAAACTG GCTGATTTTG GTAAGTCGCC CCTCGGGTCT CATTCTGGGC
29451 TGTGAACAAT GATGCTTTTG TGTGCACTTG TTTAAGCGTT GACTGGGCCT
29501 GGCCTTTGAA AACTGGAGGC CCAAGAACAT GATGCTTTGT GAGGATATCA
29551 AACTACCACA AAGGAAGTGT GAGGCACGAA ACAGGGAGGG ATTGGTAGCT
29601 TTCTAGGATT CCACCAAGTC CCAGTTTAGT CAGATGGCCA AAAGCTGGGC
29651 ACCCTTGCTG CCCCACTGCC AGTTTTGATA TAGAGACATT GGTAGAGTAA
29701 ACTGTACTTA GTAAGTTTTC CTAAATCTAA GTGAATATAC AAATTATATT
29751 GGAATAGATT GAGATTATCC CAAGATGATA AAGAGGTTAA CCCCAGATTG
29801 TAGCATGGAC TCCTGTCAGG ATGGAGACTC CAGGACACTT GTTCCTGCTC
29851 TCCTACCTTC TTTATATAAG TGTGAGATGC AAAGTTTTAT TCCCATTAAA
29901 GTGAAGCAGA TTTCCTCTAA GTATCACTGT ATCCTTCCAT TTTAGCACTT
29951 ATCGCAGTTT ATAATTATAT TCACACACAT AAATACATAC ATGCATACAT
30001 ACAAATATAT ATACATGTGT GAGCACACCC CCACACACAA ATATATATAG
30051 ATTTGCGTGA TGATTTTGTC TCAACTGGAC TGTAAGCATA ATGAGGGCAG
30101 CCTGGGTTTG TTTTTGCTTA TCATTTTATC CTTAGTGCCT GGTACCATAG
30151 TAGGTGCTTA ATAAGTACTT GTTGAAAAAC TGGCTCTATG TGAGCTAAGG
30201 AACCACTCTT CTCTGTTTGG CAGATGCCAA ATGGTGATAC TATCACTGCA
```

FIGURE 3K

```
30251 GTATTTATTC TGAGATGGCA GCTTTTATCC TGACATGTAA GCATTTAACA
30301 GATATTTGTT TATCAATTCT CCACAATAGC AAACTCATCT ATTGAAGTTT
30351 TTCCCAACAA TAGATCATGC AATTCTGTGA GATAAACAGC TGACTGACAG
30401 AAAGACTCAT TTTGCAGAAC AGTACTTAGA AATTCATCTA AGGTCCTACC
30451 AAACTAATTA ATTTGGATGA GCAGTCCCTA CCGTTTATCT ACTAAACTGG
30501 GCTTTCCTGG AGTGCCAAAA CGGAAGGTGG CCATGTTAGT CATGAACAGC
30551 TCAGTTTCTG TTACAGAGAC CCAAAATTAC AGAGGTATAA CATGCTAGAA
30601 ACTTAACTTT CTTTCGCATC ACAGTCCTGA CCTAAGCAGG CAGAGCATGT
30651 ATGGTGGCCC CATGCTATCT TGGCCCAGGC TGCTTCTGTC ACGTGGCTCC
30701 TCCATCCCCA ATTGTATGTT TCAAGATGGC TGCCACTTCC TGCTCATCAC
30751 AGCCCAGAGG AGGGAGAAAA GAGAAGCAGA ACCCTTAACC CCTCCACTAA
30801 GGCATAATCT GGAAGTTCAC ACATCACCTC TGTTCATATC ATATAGGCAA
30851 GAACTTAGTC ACCTGACCAC ACCCAGCTGC CAAGAAGGCC ACATCTAGCT
30901 GCAAAGCAGG CCAAAATTTG AGAAATTCAC TTGATGAAGT GATAGACAAG
30951 AGTCAAGATA GTGATTAGTT CTACTAAAAG CACCTAAAGT TTGTGTGTTA
31001 TTTTTTCTAA TGGTGTTTAC CCTGGTCCAG TGCATCATGG TGCAAGCCAA
31051 GGTCCAGAAC GATGGGTTTT ATGCTTTTCC CTTTTGGACA GGTCTTGCCC
31101 GGGCCAAGTC CATTCCCAGC CAGACATACT CTTCAGAAGT CGTGACCCTC
31151 TGGTACCGGC CCCCTGATGC TTTGCTGGGA GCCACTGAAT ATTCCTCTGA
31201 GCTGGACATA TGGTAAGAGT GGTGCCGAGA AAATGTGAGT CATCCTACTC
31251 ACGAGGGTTG CTTTATCATC TACATTATAT TTTAATAATA ATTCTAAAAA
31301 TGGCAATCAC GTATATATTT TTATATATAT TTATATTTAT ATATTTTATA
31351 TATATTTATA TAGTTATATA TTTATATTTT ATATATTTAT ATATTTATAT
31401 ATATTTGTAT ATATTTATAT ATTTATATAT TTTTATATAT TTATTATATT
31451 TATATTTTTA TATTTTTATA TATTTATATA TATTTTATAT ATATTTATAT
31501 ATATATTATA TATATTTATA TTTATATATA TTTATATATT TATATATATT
31551 TATATATTTA TATATATTAT ATATTTTATA TATTTATATA TTATATATAT
31601 TTTATATATT TATATATTTA TATATTATAT ATATTTTTTT ATATATATAT
31651 ATATGTATTT TTTTTTTTTG AGATGGAGTC TCACTCTATT GCCCAGGCTG
31701 GAGTGCAGTG GCACGATCTC AGCTCACTGC AACCTCCACC TCCCAGATTC
31751 AAGCAATTCT CCTGCCTCAG CCTTCTGAGT AGCTCTACTA AAAAAATACT
31801 AATATTTGTA GAAGATTCTT GCAATTATTC TATAACCTTT TACTGTTGAA
31851 CTGAGACCCA CAGAGTTCCT GCCCAAGGCA TCTTCTGAAT CTGACACTCT
31901 TTTTATGTTA TTTTATTTTT TGAGATTGGG GTCTTGCTAT ATTGTCCAGG
31951 CTGGTCTTGA GCTCCCAGGC TGAAGCAGTT CTCCCACTTC AGCCTCTTGA
32001 GTAGCTGGGA CTATAGGGCT GCACCACTGC ACCCTGGCAA TCTCATGCTC
32051 TTTCTTTCAC GCCTTTCCTC CTAGCTCCTC TCTTTAATCC TTTGCCTTGT
32101 CTTCTCCTTG ACACCTTATC CACAGAGAAA CAAACATATA TCCCCAAACC
32151 ACAGACACAC AGATGTGTGT GCACGTGCAT GTGCATGCAC ACACATCTGC
32201 ATGAACATAC TCACACATGT CCAAACGTAG TTCAGAGCCT GGTTTAGGAA
32251 AAAAAAAAAA AAGCATAAAG ACCAAGCTTC AAGACACCTG ATTTTCATGC
32301 CAGTTCGATT TCTAATCAAT TAACTCTGGA TTCTGTTATC TTGAAAAAGT
32351 CATGTATCCT CTCTGTGTCT ATGTTTCTCC ATTTTTAAAA ATGAAGGTAA
32401 TAAACTCTCT CCATCTGAGT TAAATGGAAT TGTAGTACAA ATATAAGAAC
32451 CAAATAGGTG GCTGGGCTTG CCGTCTCATG CCTGTAATCA CAGCGCTTTG
32501 GGAGACCAAG GCTGGAGGAT CGATTGCTTC AGCCCAGTTG TTTAAGATCA
32551 GCCTGGGTAG CACAGTGAGA TGCTGTCTCT ACATTTTTTA AAAAAATTAG
32601 TCAGGCGTGA TGGCTAATTA AACACTTCAG GAGGCTGAAG TAGGAGGATC
32651 TCCTGAGCCT GAGAAATTGA GGCTGCAGTG AGTTTTGATG GTACCCCTGC
32701 AATCCAGCCT GGGTTACAGA GCGAGACCCC GTCTGAAAGA AAGAAAGAAA
32751 CAGAGAGAGA GAGAGAGAGA GAGAGAGAAA GAAAGGAAAA GAGAAGGAGA
32801 GGGGAGAGGG GGAGAAAGGG AGAGGGGGAG AGAGGGGGAG AAGGGGAGAG
32851 GGGGGAGAGG TGGGGAGGGA GGGAGGGAGG GAGGAAGGGA AGGAAGGAAG
32901 GAAAGGAAGG AAGGAAGGAA GGAAGGAAGG AAGGAAGGAA GGAAGGAAGG
32951 AAGGAAGGAA GGAAGGAAAG AAGGAAAGAA TCCAGATAGG TGCTATCAAG
```

FIGURE 3L

```
33001 TAAAGCCACA GAGTTGGGGA GGCTCTAAGG TTAATGGGTT ACAATAGTGA
33051 GCATGGGCTG TCAGACATGC ATCATCCTAG AACGGCAGTG TTATTTTCTC
33101 TGGATCATGT TCCTGGAGAC TTCCCAGTCA TTTGGGGGCC ACTGTTAGAT
33151 ATGTGATGAC TTTACAGACG TAGACAACTC CCCAAAGGTA AGGAAATATA
33201 TGAATCTCTT TCAGTACCTT GGAAGAAAGG GTTTATATAA AAACACAAAG
33251 CCCCATTTTC AAAAATCCAT AATTGATTTT AAAAAATTAA ATGGTGTCCT
33301 AAAAGGCTAA ACTAAGCTTT TAGATCTCCC AAAGAATTAA GAAAGGTTGC
33351 AGACATTTTT CTCCAGTGTA GAGTCATTGA TTTCTGATAC CCAGTACAAT
33401 TTATAGAAAT ATCATCTGCT AGTCAAAACC CTCCTGAAAC TGTCAGCTCA
33451 CACCGCTCAG CACTGTCACT TCAAAGGACT CCGGCAGGCT CTGGCTTACT
33501 CAGCTCTTAA TGATGTCTTC CTGATTATGT TTCACAGAGT GAAACTTCTA
33551 CCCGTCAATT TTAAACTAAT TTTATTATGG AATAGTTAAA ACATTCAAGA
33601 GTATATATAA CATATATGTA GATCAGTGAT TCTCAACCAG GGAGCAATTT
33651 TGCTCTGCAG GGGACATTTG GCAATGTCTG GAAACATTTT TTGTTTTCAC
33701 AGCTGGGGGT GGGGTGGTGG GGGGTATCAC TGGCATCTAG TGGGTAGAGA
33751 CCAGGGATAC TGCTAAACAT CCTACAGTGC AGAGGACAGC CCCTGCAACA
33801 AAGATTTTTC CAACCCAAAA CATCTGTAGT ATCAAGATTA AGAAAGCCGA
33851 TGTAGGTTAA GAAGCTTAAT TTACTTTTAG AGACAGGGTC TCCCTTGGTT
33901 GCCCAGGCTG GAGTACAGAG GTGAGATTGT CTCACTGCAG CCTCCAACTC
33951 CTGGGTTTAA GTGATCCTCC TGCCTCAGCC TCCTGAGTAG CTGGGAATAC
34001 AGGTGTGTGC CACCACACCT GGCTAATTAA AAAAAAAAAA GTGTAGAGAC
34051 AGAGTCTCAC TTTGTTGCCC ATGCTGGTCT CAAACTCCTG GCTTCAAGAG
34101 ATCCTCCTGC CTTGGCCTTC CCAACTGCTG GGATTACAGG TATAAGCCAC
34151 CGTGCCCAAC CAATTAAGAA GCTTAATAAC GTGAACTTCA TAACCTGCTA
34201 CCCAGTGTAA CAACTAGAAC ATAATCCGTA CTGTCCTATC AACTGTGTCC
34251 CTTTCCCATC AACCTGCCCC TCCACTAGAA GGCCTTCTAC CAAAATTTTT
34301 TTTCCTTTTT TCATCAGTAT TCTCATATCT TTTTAAAAAT AATCCTTTTA
34351 CATTTTAGAG GTATTCTTAA AAATATTTTT TTGTTTTACT TGATTTTAAG
34401 GGTTGTTTTT TTTTGAGACG GAGTCTCGCT CGTCGCCCAG GCTGGAGTGC
34451 AGTGGTGCGA TCTCAGCTCA CTGCAAGCTC CGCCTCCCAG GTTCACGCCA
34501 TTCTCCTGCC TCAGCCATGA TGTTATATTG CTTCTAGTCT TCTGTGACTT
34551 GGCTTTGTTT CATTCAATAT GTTACATGTT TCTAAGATTC ATCCATGTTG
34601 ATCTGTTTAG CTATACTTTA TTTTCTGTTA GTGAATATTT CATTTTTTTT
34651 AATGTCTATA GCTTTGCAAT AATACTTGAT ACCTTGTAGG CCAAGTCTCC
34701 CAGCCTATTC ATCTTCTTCA TGAGGATACA TCAGATAAAC CTAGTTTAAG
34751 GGACATTCTA CAGAGTAACT GACCTGTACT TATTGGAAGT GTCAAGATTT
34801 TAAAAGATAA AGACTGAGGA ACTGTTCCAG ATTAAAGGAG ACTCCAGAAA
34851 CCTGCCAACT AAATGTAACG CATGGTCCTA GATTGGATCT TGGGGGAGAT
34901 GGTGCTCTAA AGAATACTGT AGGGACTATA GGTGAAATTT CAGTAGGGAC
34951 TGTGGATTAG ATAGGGGTAT TGGATGAATG TTAAATTTCC TGATTTTGAT
35001 AATTGCACTG TTGTTATGTA AGAGGATACT TTGGTTCTCA GAAAATACCA
35051 ACATAATTAT TTAGGGATGA AGAGTCATGA TATCTACAAT TTACTCCCTA
35101 ATGTTTCAGA AAAGATATAG ACAGACAGAC AGACAGACAG ACAGACAGAT
35151 AGATAGATAA AATAACGAAA CAAAAGTGAC AAAATATTGG CGATGGATGA
35201 ACCTGTTTGG AGGATATAAG AGAGTTCTTT ATACTGCTGC AACTTTTCTA
35251 TAAGTTTGAA ATTATTTCAA GATTAAAAGT TGCCTCCAAA TTGCGAAATC
35301 CTTGCTGTTT CATCAAAGTT AGTGTAAGAC AGCACTAGCC TAATATGTGA
35351 TCAGTGTTTG TAATTTCTTC ATGTGTGTTT GAGAAGAATG TGTGTGTCCA
35401 CCCAAATGTT GAGTGCTGCT GGGGTTTTTT TTTTGTTTTT GTTTTTGTTT
35451 TTGTTTTTTT TGAGACAGAG TCTCACTCTG TCTCCATGCC TGGAATGCAG
35501 TGACTCAACC TCGGCTCACT GCAACCTCCA CCTCCTGGGT TCAAGCGATT
35551 CTCCTGCCTT AACCTCCCAA GTAGCTGGGA TTACAGGAGC ACACCATCAC
35601 ACCCGGCTAA TTTTTGTAGT TTTAGTAGAG ACGGAGTTTC GCCATGTTGG
35651 CCAGGCTGGT TTCGAACTTT AGATGTCAGG TGATCAGCCT CCCAAAGTGT
35701 TGGGATTACA GGCATGAGCC ACCGCGCCTG GCCAAGTACC CATTTTTACA
```

FIGURE 3M

35751 TATGTTCAAA AATTCAAGGT TGCTAATTAT ATTATCCAAA TCTTCTTTAT
35801 ATTATTTTTG TCTTTTTAAC CTACCAATGA AAGGTGTGTT GAACTCATTC
35851 ACTATATTGT TGATTTGTCA GAATTCTATC CACTTTTGCT TTATATGCTT
35901 TGAAGCTATT TTCACTAAGG GCAAATAAAT TTAAGACTGC TCATTATTCC
35951 TTTGTACACT TTAGTTACCA CTTTCAGAAT AATTTTCATT TCTCCTGAAA
36001 TACATCTTTT AGAGTGTTTT GTTTTGTTTG TGTGTGTGTA GGCCTGCTGG
36051 TGGCAAATTC TTCGTTTTTG TTTTCAGAAG ATAAACCCTA ATTATTGAAA
36101 GGTGGTTTTG TTGGGGATGT GATTCTAGAC TGACAGTTAT TTTCTCTCAG
36151 AACTTTGAAG ATGTCATTCC CCTTCTTTGT CTTCCATTGT TGCTGTCGAG
36201 GAGTTTGCTT TTAGCCTTAT TATCTTCCTT TTGCAGGTGA TCTCATTTTC
36251 TCTGGATGTT TTAAAGACTT TTTTCTTTGC CTTTATGATT ATGCAGTTTT
36301 CTCTAGGAGT TGTCCAGTGT GGATTTCTTT TTACTTACCC TGTTTGGTAT
36351 ATCTTGTGTT TCTTCCATTT GTGAATTCAT GTCTTTCATC AGCCATTTTC
36401 TTTTTGAATA TTGACTCTAT TCTATTCTCT CTCTGTAGAG CTCCAATGAA
36451 AGACTATTAG ACCACATTCT TCTGTTATCC ATTTCTCTTC TCTCCTTCAT
36501 ATTTTCCATT TCCTTAACTT TCTGTGATGC ATTCTGGGTA ATTTCTTCAG
36551 CTCATCTACC AGTTCTTTAA GTCTCTCTTA AACTATGTAT TAGGTTGGTG
36601 CAAAAGTAAT TGCAGTTTTT GCCATTAAAA GTAATGGCAA AACCATAGTT
36651 GCTTTTGCAT CAACCTATAT CTCTTACCTT TTTACCACAT ATACAAAAAT
36701 GTATGTTATT CTATGAATAA GTGTTTCATG AATTTAACCA TGAGCAACAA
36751 TGACACAATA TAAAAATGCA GTTATAAGTC AAAATTATTG TTATTACTCT
36801 TATTCATTCC ATTTGATTGT TGTTTTCCTG GTAAAACTAA AAATGTAATG
36851 TAGAAATAGA ACAATATGCA TCTTCCATTG AGCTCACTAT ATTTGTTTAC
36901 CCTCAAAGTA ATTGCTAGAC CTTGGGTATT TACACTGAGA TCCCTCTCCT
36951 CCCATTTTTT TCTTTTTCTT TTCAGAGTGA TAAGAGGGGA AGTGAGAAGG
37001 GAGAAGATTT CCAGTTGACA AAGAATGAAA AAGAAAGAAT AATCCTATTC
37051 TGCTAGGCCA TGCAACCCCA TAGGGTCCAA AGTGAATGCC CTTGTAGGAG
37101 GTAGATGACA CTGGGTGAGC ATTAGTGCAT TTGTCTTAAA GAAACCAATT
37151 ATAACCCGTA GTGCAGAGCC TCTCCTTCAC AATGAGGCCT GGTGGCAGCA
37201 GTGTCAGTAG GGGGCCAGAG CAAATAAACA GGGGCTCTAG TTAATTATGG
37251 AAAACTTGCA ACTAGGACAT ATTGGTTATT CCCAAAGCTC CCAACCAACA
37301 TTCTCTCATC TTCTGACGTC TTTTCTTCTC TCTCTTTCTG CTACCTTTTC
37351 AGACCTTAAA AGATTCCATT AGTGACTTTA GTGAGAAAAA TGCAATATTT
37401 TAGGATTATT AAATGGTGTG GTTTTTAGTT TTTTGTATTG TGTTAAAATA
37451 TACATAAAAT TTACCATTCA TCACGATTTT CAGGTGTACA ATTCAGTGGC
37501 ATTCAGTACA TTCACATTGT TGTGTAACCG TCACCACTGT CCATCTCCAG
37551 AACTTTTCAT CATCCCAAAC TCAAACTCTG CACGTATTAA ATGATAATTT
37601 CCCATTACCC CCTCTCCTCA GTCCCTGGTA ACCACGATTC TGCTTTTTAT
37651 CTTGATGAAT TTGACTATTC TTGGTACCTC ATATAAAAGT GGAATCCTAC
37701 AATACCTCTT CTGTGTCTAG CTTGTTTTGC TTGGCATAAC ATTTTCAAGG
37751 TTCATCCATG TCGTAGTACA CTGAGTTTTC CAGAAGCATT TATTTCAGTA
37801 CACAAGGTCA TCTATTCAGT ATCAGTTTCA GGCAGCTGCT GGTGTTAGGA
37851 CTAGAGAAAG TTGTCTCTGC CTAACAGATC ATTTACTGTC ACATTTCTCG
37901 CTGCAAACTT CCAAATATAA AAAGGGTGGT CTAGAGAAAA GCAAGTGAGA
37951 ATGTCATGTC ACTGCCATAT ATTACGTTAT TCTGAATTAA CTTCAACAGT
38001 AAGAAATGAA ATACTGATTC ATTTCTCCCA ACAACATTTT GATATTCTCC
38051 TTGCACCTCC AAAAAGCCTA AAACTCCCGA GATGGATTTT TTTTCTCCAG
38101 GGACTGCCTA AGGAATCTGA GGAATCTTTC CCCCTCTTAT GGAAGAATTT
38151 GTTCATGCTC AGAATAGAGA AAAAGTAGGA GGAGAACCAG AAAGAGGAGA
38201 AAACATCTAA GCAGTTTCCT CTAACTTGAC TGAAGAACCA CATTTGGAAC
38251 AATAAAATGA CCCAGCACAT CTCTCCCTTC TGGAAGGGTT TAATGTTTGA
38301 TGTCACAGGG TCTTTTCTCC CCTGCATATG AATTTCCCCT TCGTCTACAC
38351 GGGCTGCCCC ACGGGTATCT CCACACAGCA GAAATCCTCA GAGAAGCTTA
38401 AAGATATGTA GGGTAAGAGG AGCCCCAGGA ATGAAGATTT AAGGACAAAA
38451 CAGAAAAATA AAAGGAAATA GAAGCTGGTT CCCTATCTGG ACTTGAATGT

FIGURE 3N

```
38501 TCAGAATATT TAAAATGTTT GCTTTAAGAA TAGTCTGTGG TGGGCAAAAT
38551 AGATGATAGC CACATGACTT GTATTCCTAA GGGTAAGAAG CAAATTAAAA
38601 AAAAGAAACA GTTCTGAACA GAAATGAAAA AATAAGATAA ATTGCATAGT
38651 TCTTTTTTTT TATTAGATGG AGTCTGGCTC TGTCGCCCAG GCTGGAGTGC
38701 AGTGGTGCGA TGTCGGCTCA CTGCAACCTC CAACTCCCCG GTTCAAGTGA
38751 TTCTCCTGCC TCAACCTCCT GAGTAGCTGG GATTACAGGA ACACACCACC
38801 ATACCCGGCT AATTTTTGGA TTTTTGGTAG AGACGGGGTT TCACCATGTT
38851 GGCCAGGCTG GTCTCGAACT GACCTCATGA TCTGCCCGCC TCGGCCTCCC
38901 AAAGTGCTAG GATTACAATG CTTACACCTA GAACAGATCT GTCACCTTTC
38951 AAACTTACAG TGTGGGCTTG TTTTGTTATC AATGCATTGA TATTTACAGT
39001 ACCTATGGAT AGTCCATGTA CTGAAATAAA ATTGATTTAG GAATTTTGTC
39051 TTATAAGTGT TCTAAAGACT TGCACAAGTG CACACATACA CACACTATAT
39101 ACATAGTGTG TGTGCATGTG CGTGTATATA AATGAGTAAC CTTAGACTTA
39151 GATTTGTTAG ATGAGGAAGG TTTCAACCTT CCCCAAAATG CAAATGGAGA
39201 ATTTCAACCA TATAAACCAA ATATTGGCAT TTTATCTCTG GAACACAAAC
39251 ATCTTGTGTT ACTTTATGGT ACTTACGTAA TGGCCTGAAT GCTCTAGTTT
39301 TTGCCAATAT ATTTTACATA ATTTTGTATA CAAGTTTAGT GGTATAGAAG
39351 ATAAAGGACA CTAAGCAGGA TTAACAGCTT GGTTCCCTAC AGCTGTTAAG
39401 TATGAAAACA CACCATGAAA AGGCAACAAG CTTCTTCCAG GCAATGGAAG
39451 GCTTTTTGGG GGAGAAAAGA AAGTGAATTA CAGGTTTAAA CCTAGGAATG
39501 TCATTTTTTG AAACTTGTTT AAAATATTTT CAATCCTTCT AGTGGTTTGT
39551 GAGCTCCTGG GGTTTCTGGA AGGTGTTTGG GAACTGGATA GAGGGTTAGT
39601 TCATGCCTTT AAAAGCCAAT ACATTTCCAT TTCTCTTTTA TAACCAAGTA
39651 ATAACCCAAT TATGCATGTA TTTTATATAC ACAGACACGT ATTTATTTTT
39701 ACTCCAAAAC AAAATGGTCT GAGGCCTTTC AAGAAAGTGC ATGTGGCGAA
39751 GTCATGGGGG GCAGGGTGGA GACCATTTGG TGGTGCCCAC TAACTAGGTT
39801 TCTCAGTTGG CTTATCTCTT AGTGGACCAT TGCTAGCAAC CAGGGTGTTT
39851 TTAAGCATTT GACAGTTTTC CATCACTTTT ATTTGCCTTC ATATATTGTT
39901 TCATTTACAC CCTTAGTATC TCTTGTTTTA AAGACAGGAG ACAAAAAGAA
39951 CATGGATATT TAAATACAAG TTAATGAGGA ACTTTAAAAT AATAATAATT
40001 CTACAAATTT ACCTCAAGAT ACTTTACCAA ATTCATAAGT TACATTTATC
40051 TGATCAAAAT TCTTGTGTCA CATATCAAGA TGTTTCTTAT ACAGCAGAAA
40101 TCAGTAGAAA AGAAAAAATA GGCCAAGCGT GTGGTGGCTC ACACCTGTAA
40151 TCCCAGTACT TTGGGAGGCC AAGGCAGGAG GATTGCTTGA GGTTTGGAGT
40201 TCAAGACCAG CCTGGGCAAC ACAGTGAGAT CCCATCTCTA TTAAAAAAAT
40251 TAGAAAAGAA AAAGAATAAA ATGGGGCTGT TATATCCAAA TTGGCTTTTT
40301 AAAAATCAGC AATAAGGCCG GGTGTGGTGG CTCACACCTG TAATTCCAGC
40351 ACTTTGGAAG GCTGAGGCAG GCGGATCAAT TGAGGCCAAG AGTTTGAGAC
40401 CAGCCTGGCG AACATGGTGA AACCCTGTCT GTACTAAAAA TACAAAAATT
40451 AGCCAGGCAT GCTGGTGCAT GCCTGTAATC CCAGTTACTC AGGAGGCTGA
40501 GGCAGGAGAA TCACTTGAAC CTGGGAGGTG GAGGTTGCAG TGAGCTGAGA
40551 TTGCACCACT GCACTCCAGC CTGAGTGACA GAGTGAGACC CTGTCTCAAA
40601 AAAAAAGAAA AAAAAAATTG GCAATAAAAA CAACCTGTTG CTTGCTGGAG
40651 GAAAAACCTG CTTGCAAAGC TCAGTCTGAT ATCATTTTTT AAACAAAACT
40701 CTAAGAACAA GCCAGTCAGT TAAGCTAAAA CCAAATATTT GATTATGAAA
40751 AGGGTTTTTG TATATTTTTA CAGGATAAGA TACAAATAAA TTTCAGTCTT
40801 TCTTTTAATA TGTATTTCTG TTCCCAAACC AGACACAAAG CAATTTTTAA
40851 ACTTGATCGT CAAGAAATCT GTTTTCTCCT ACACAATCAA TGAAAAGTAA
40901 TCTAAACAGT GTTTGTCAGG CCAGGCACAG TGGCTCACAT CTGTAGTCCT
40951 AGCATTTTGG GAGGCCTAGG CAGGTAGATT GCTTGAGCCC AGAATTTCAA
41001 GACCAGCCTG GACAACATGG CGAAACCCCA TCTGTATTAA AAAAAAAAAA
41051 AAAAAAAGAC CATATGTCTG CAGTCAGATG GAAAAAGTAA AAATATGTAA
41101 TAAACACATA TGAATAATAT TAAGGACCAT ATTTTAAAAT AAACTTGATA
41151 ATAAATTTTT AATAATATTA TCTACGATAA AATGTTTTAC TTAAATTTCG
41201 TTCTTTATCA TGCCACACAA AAATGGCAAA ATGATTAAGA GAGTTTGCAA
```

FIGURE 3O

```
41251 AATTATGTGG TATAGTGAAA GAGGTTTGCG GTTAAAAAAA AAAAAGAGAG
41301 AGAGAGAGAG AAGTATGGGG CCATGGGGAT AGTCTCTGTA ATCAGTCACC
41351 TGAACCACTT TTAATACTCA AAAGACTTAT GAGAATAAAA ATCTGATTTT
41401 TGCTAAGATT TATTAGCAAA ATAAATCTTA CTCCTTCCTG TCCCTCTCTA
41451 ATTATCCTTC AGCTTGACCA TGTATGAAAG AAAATTTACA TTTCACTGTT
41501 TAATCTATTT AAAGATGAAC ATTTCCCATT AAATCAGGAT GCACCTTATA
41551 ATCAGTAGCA TCTAACAATA TAAGTCAGCC AGGCTGCAGT TGTGACTGTA
41601 GTTAGAATTG CACATGTGTG AACATCAAAT GAGCCAGCAT CAAAACGTGC
41651 AGAATGGCCA GGCACAGTGG CTCACACCTG TGATCCCAGC ACTTTGGGAA
41701 GCTGAGGTGG GTGGATCACT TGAGGTCAGG AATTCAAGAC CAGCCTGGCC
41751 AAGATGGTGA AATCACGTTT CTACTAAAAA TACAAAAATT AGCCAGGCAT
41801 GGTGGCAGGT GCCTGTAATC CCAGCTACTT GGTAGGCTAA GTCAGGAGAA
41851 TCGCTTGAAC CTGGGAGGCG GAGGTTGCAG TGAGCTGAGA TCGCACCACT
41901 GCACTCCAGC CTGGGCGACA GACCAAGATT CCACCAAAAA AAAAAAAAAA
41951 ATTGCAGAAT TGGTGTCAGC GACTTGGAAG AAAATTCTGC AAAGAAAAGT
42001 CCTTTTTTTT TCTTTTTTTT TTTAAACTCC TAGGAACCAA ATGGTTGTGG
42051 AGAAGGAGTA AATCAGACAT GTTTAGCAAC ATTCTTTAAG CAGGAGTCAA
42101 AAGTAAGCTA ACACTACATA ACTGCAAGGC CAGCTTAGGA GCCCAGGACC
42151 AATGACTCTC TGTTGTTTTA TGGATTATTT TAAGAAATGC TGCATCATCA
42201 AATTCTTAAT ATAGAGGATG ATACATGGGT AAGTGTAGAC ATCAAAGAGT
42251 CTGAGTCAAA TGCTGAATGT GAAAAAGTTT TAGGAATACC GAAACCAATT
42301 TATTTTGCTT AATGTTTCTC TTTTTCGTGT ACAAGTATGC TATATGAGAA
42351 AATAATCTCT ATTTAATTAA ATTTATAACA GCCCTTTCAA TAAGTATAAA
42401 ATGAACATTC TGATCATGTC ATAGTTTAAC TTGCATTTTT TTGTCTTAAT
42451 GGCAAAAAAC CAATGACGCT TCTTACAATG ATAGCATCTT AGACTCAATG
42501 AAAAGTGGGG ATGAAATGAA ATTTGGGGAT ACAGTACTTT CCCCTCTTCT
42551 CCTAAAACAG ATAATGAGCT TGAATGATCT ACAATGTTTG CTAACTCTAC
42601 TGCTTTCCTA ACTGCTGCTC GTGGTGTTCC ATTTTAATAA AAAGCTGTGG
42651 GCTGTTCTTA TTTTGTTTGA CATAGGGACT TTTTTTTTGG CCCAAGACTT
42701 TTAATATCAT GTGGTCCGTA TTTAACTCTC CCTAAAATAT TTCTTGGGAA
42751 GAGAAATTCT AGTAGTTCAG TTTCGCTTGT ATGATTTCTT TCAAAGTGTC
42801 AATTTACTCT TATTTCCTTT GCTAGGGGTG CAGGCTGCAT CTTTATTGAA
42851 ATGTTCCAGG GTCAACCTTT GTTTCCTGGG GTTTCCAACA TCCTTGAACA
42901 GCTGGAGAAA ATCTGGGAGG TAGGAGAATA ATTCTTCTAA AGAAAATGAA
42951 ATATCTGCAT TTTAAGTTTT GAACCAAATT TGCCTTACAG ACAAATGAAG
43001 CAGTCCATCT GCTCTGAGAT ATTAAGCCCT ATATTAAGAT TGTAGAAACT
43051 GTAGCATTTG CCACAGCTAT AAGCACCCTG GGAATGTGTG GTCAGGAAAC
43101 TCCCTGTTGC CCCATAGCAG CCCATGAATC CAGCTCACTG AATGATGTTC
43151 AGGTCTCCTG CTCCCTGTCA TTAGTATTGT CTTAACCTCC CAGGGCAATT
43201 TCTGCCATTA CTACTCAGAC ATGTCCCTAC CTTGCTACCT CCAGTTCTAA
43251 TGCTACCATA TATTTGGCCC TGGATCTTTG TCAACTGAAA ATAAGACATA
43301 GAATTTTTAG CTGGGTGCAG TGGCTCATGC CTGTAATCCC AGCACTTTGG
43351 GATTGCTTTG AGCCCAGGAG TTCGAGACCA GCCTGGGCAA CATGGCGAAA
43401 CCCCATCCCT ACAAAAACAA AAATGAGTGG GCTGTGTGGC GCACACCTTA
43451 GTCCCAGCTA TTCAGGAGGC TGAGATGGGA GGATCACTTG AGCCCAGGGA
43501 AGTCGAGGCT GCTGTTAGCT GTGACCACGC CACTGCACTC CAGGCTGGGG
43551 AACAAAAAAA AGACACAAAA TTTTCATAGA ACCCTGATAG AACAGAGGCT
43601 TTCCCTCTTA GTGTGAAAGA AGTGTACCAT TTATCATGCT TATCCACAGC
43651 CAAATTCCTA AAGTGTCAAG GTGCCTTTGT GTGTGTATGC AGCTCCATTT
43701 CTTAATTCAT TATTTATCCC TACCGCAGTT GCCTATGATA TGCTTTGTTT
43751 TTATGGCCCT TATATAGTAT TACAGTCATA CTATAGTCAT CTGTATATTT
43801 CCTTTTTTGG TCATATTTTT ATTGTGGTAA AATATACAAA ACAAAATTTA
43851 CCGTCTTAAC CCTCCTTAAG TGTACAGCTT GTCAGCATTA AATACATTCA
43901 TATAGTTGCA CCACCATCAC CGCCATCCAT TTCCAGAACT TCTCTATCAT
43951 CCCTAAGGGA AGCTCTGGAC CCACTGAACA ATAACTGCCC ATCTTCCCTC
```

FIGURE 3P

```
44001 CCCACACTCC CCTAGCCCCT AGTAACCTCT AATCTACTTT CTGTCTCCAT
44051 GAATTGGCCT ATTCTAGGTA CCTCATATAA GTGGAATCAT ACAAATTTGT
44101 CTTTCCGTAT CTGGCTTATG TCACTTAGCA TATTTTCAAG GTTCATCCAT
44151 GTTGTAGAAT GTGTCAAGGG GCTTTAAATC GGCGGGGTGC AGGGGGGTAC
44201 TTTATTACTT GCTATCCTGG ATCCTGCTGC TTGTCTTCTG GCTAAAATAA
44251 AATGTACTTT GTGAAATTAA GACATTTTAT AGAGATTAAT TACTGACATT
44301 AAATTTTCTT CTAGAAACAT GGGGGCTATT ATGAAGGAAC ATGGGAAAAA
44351 CTGGGAAGCA TTCACAACTG AAAAAAAAAA ATCCAAGCCA AAAGACTTTT
44401 TCTAAAAACT TTCTTGCAAG ACAGAGCAAT GCTATCTTCA CATTATGTTA
44451 TTGGGTGCTA TAACATCATC TAAGCTGGAG ACAGCCTACT GTCATAGCTT
44501 TGGAGTCCAA AGACCTGGGT TTGAATTCTA ACCATTTTCT AGCTAAATGA
44551 ACATGGGCAA GTTATGTAGT CCCTCTGAAC TTTCGTTTCC TTGTCTGTAA
44601 AATGGCAACA ATGATAATAA GGACTTTCTA ATTCTTTATT GAGAATTCCA
44651 TAAAAACAAA TGCATAACAA GCTCCATGCA CCATAAATGC TCAATAGATG
44701 CTTGCTTTCT TCCTGTCCCA TACAAATTGT TGTACAGATG TTTCAATAAC
44751 CTAACTGCTA GCAAGTATTA CCTGAAATTT AACCCGATTG TTCTCTTCTT
44801 TCACTTAGCA GTATTATTTC TTGTCCACAA TAGAGGAAGC ACAATTGCAG
44851 TTCTGATGCT GCAATGACCT TTTATACATT TGAAGAGTTT TTCCTGGTCA
44901 TTTAATCAGG AAACAACACT TACTCACCAT ATATGAGGCG AGTAACTCTA
44951 CAAGACTCTA CAAGGTCTTG TAAGAAGCTA TAAGCCAAGG GGGAAAAAAA
45001 AAAGAAGAAT AAGAAAAACA CATGATCTGT ATTTTCAAGT GTTGTTCAGT
45051 CTAGGTAGGG CGATGGGTGA AGTATACGTA AATATATGTG AAACAAACAT
45101 AAACTATGTA TATATGTAAA AGGATGTATG TATAGATAGT TAATATAAAT
45151 TGTAATACTG AAATAAGATG TGCTATTAGG ATACTTGAAG AGTAGTTTAT
45201 TTGAAAAGAA TATAAGTATA TCCTTGTGTG CCATTAGTAT TTGAAGAGTT
45251 GTATATAAAC TGATTTTTTT TCTTTTTCCT TTTTTTTGAG AAGGAGTCTT
45301 GCTCTGTCAC CCAGGCTGGA GTGCAGTGGT GCCATCTCGG CTCACTGCAA
45351 GCTCCACCTC CCCAGTTCAA GCGATTCTCC TGCCTCAGCC TCCTGACTAG
45401 CTGGAATTAC AGGTGCCCGC CACCACACCT GGCTAACTTT TGTATTTTTA
45451 GTAGAGACGG GGTTTCACCA TGTTGGTCAG GCTGGTCTCA AACTCCTGAC
45501 CTCGTGATCC ACCCGCTTTG GCCTCCCAAA GTGGTGGGAT TACAGGCGTG
45551 AGCCACCGCG CCCAGCCTCA TAAACTGATT TTTAAAATAC AATATACAGT
45601 TAGGCATAGT TGTGTGTGCC TATAGTCCCT ACTGCTTGGG AGGCTGAGGC
45651 AGGAGGATCC TTTGATCCCA GGAGTTTGGG CAACATAGTG AGACCCCCAT
45701 CTCTAATAAT AATAAATATA AATTTCAAAT AACATTTTAA AATATGACAT
45751 ACTATCTTTG AATGACCACA CAATTTAAAA AGCAATCATT TTACGGTTCT
45801 TTAGTGTTCA GTTAGCACAG CACTTAGAAA TCATAGAATA AAGTGAGCAA
45851 GATGCTTCTC AAAGCCTGAT CACTCTTTAG GACTCACAAT GGGCTAGGTA
45901 CTATGCTGGA AAGAGAAAAA ATAATAATTT TCTAACCTGC TTGAGACATA
45951 GTGGTATAAA TGATAACACA GCTGCTGAAC GTGATGACTT TCTCACTTTG
46001 TCCGCAGAGC AAGAAACTAT AGATGCAGTA ACAAAACTGC ATTCAATGAA
46051 CATGGGACTG TAGATAACAA ACTAACTTCA TTTCTTTGGG TACATGCCCT
46101 GTATTGGGAT TGCTGGATCA TATGGTAGTT CCATTTTTAA TATTTTGAGG
46151 AACCTCCATA CCATCTTCCA TAATGGCTGT GCTATTTGCA TGCCCACCAT
46201 CAGTGTGCAA ATGCTCCCTT TCCTCCACAT TCTTGCCAAC ACCTCTTTCA
46251 TCTTTTTGAT AATAGTTATG AGGCAATATC TCACCATGGT CCTAGACTTC
46301 ATTTGTCTGA TGACTAATGA TATTGAGCAT TTTTTCATAT ATCTCTTGGC
46351 CATTTGTAGG TCATCTTTTG AGAAATGTGT ATTGAGGTTC TTAGTCCATT
46401 CCTGCTACCA TAACAAAATC CCTTAGAGTG GGCATTTTAT AAAGAACAGA
46451 ATTGGCCCGG GGCGCAGTGG CTCATGCCTG TAATCCCAGC ACTTTGGGAG
46501 GCCAAGGTGG GTGGATCACC TGAGGTCAGG AGTTCAAGAC CAGCCTGGTC
46551 AATATGGTGA AACCCCATCT CTACTAAAAA TACAAAAACT AGCCGAACGT
46601 GGTGGTGTGC ACCTGTAGTC CCAGCTACTT GGGAGGCTGA GACAGGAGAA
46651 TTGCTTGAAC CCAGGAGGAG GAGGTTGCAG TGAGACGAGA TCGTGCCACT
46701 GCACTCCAGC CTGAGCAACA GAGTGAGACT TCATCTCAAA AAAAAAAAAA
```

FIGURE 3Q

```
46751 AAAAAAAAAA AAAGAACAGA AATTTATTTC TCACTGTTCT AGAGGCTGGA
46801 AAGTCCAAGA TCAAGGCACT GTAGGCTGTT GTCCAGTGAG TATATTTGGT
46851 CTCCAAGTTA GTGCCTTGTC GCTGCATCCT CCAGATAGGG CAAATGCTGT
46901 GTCCTTACAT GGTGGAAGGG TAGAAGAGCA AACGGGCCTG ACTGATTCCC
46951 TCTAGCTCCT TTATAAGGGC ATTCATCTCT GTCCTTGTGT CCTAATCACA
47001 CGCTAAAGGT GGCTAAAGGC CCCACCTCTT AATACTGTTG CATTGGGGAT
47051 AAAGTTTCAA CATGAATTAT GAAGAGAATA CAAACATTTA AACCACAACA
47101 AGTCCTTTGC CCACTTTTTT TTTGGAGACC GAGTCTCACT CTGTTGCCCA
47151 GGCTGGAATG CAGTGGCTTG ATCCTGGCTC ATTGCAACCT CCACCTCCTG
47201 GGTTCAAGCA ATTCTCCTGC CTCAGCTTCC CAAGTAGCTG GGATTACAGG
47251 TGTGCACTAC CACACCCAGC TAATTTTGTA TATTTAGTAG AGACAGGGTT
47301 TTACCATGTT AGCCAGGCTG ATCTCGAACT CTCGACTTCT GGTGATCCAC
47351 CTGCCTCAGC CTCCCAAAGT GCTGAGATTA CAGGCGTGAG CCACCGTGCC
47401 CGGCCCTTTG CCCACTGTTT AATGGGGTTG TCTTCTTGCT ATTGAGTTCC
47451 TTATATATTT TTTATATTAA CCCCTTATCA AATGTATGGC TTGCAAATAT
47501 TTTCTCCCAT CGTAGGTTGT CTCTTCACTC TAATGATTGT TTCCTTTGCT
47551 CTGAAGACAC TTTTTAGTTT TATTTATTCC CATTTGTCTA TTTTCACATT
47601 TGTTGCCTAT AAGCAGGTTA GAAAATTATA CAGATTATAA ATAGTTCCTG
47651 AATTTGTGTT TTACTAAACG TAGCCTACAC AGATGAAAAC AGGAAAGCTA
47701 CACTTCAGAA TCTGTGATAT TTGATGTCAG AAGTGCATCC CTGAAAGCAA
47751 TGGGTCCATT CTAAATCTCC TAACCTCTAA CCATAATTTG TTCTATATTT
47801 ATCCTGAGAT CTCACTCTTA GGAATAAAAA CACATTGAGA AGTCCTGAGT
47851 CTCTATTTTA CTATTTTTCT GAAGTGCCTG TAGTGTGTGT GTTTACATCT
47901 AAATAATAGC TGTCACCACT TTCTGATCAA TTTTAAAAAC TAATTTTAAA
47951 TAAGTGTTTT TCATAAATAA TCCTGGATTT AGTTCTAAAA TCAGAATAAA
48001 CTATGCAAAC TTTGAATCCA TTAATCAAAA TGCTTTTAGT TTCCATTCCA
48051 ACAAAGGCAG ATAAACAGCC CCTTCAGACC ACTGTGGTTT GAAACATAGC
48101 ACTCACTGGC TGCCTTTTAA GAGCCTTCAG GGAGGGAGCA AAACAACAAT
48151 TTTTGGTTTT CAGTTTCCCA GACAGTGAAG GAGAGATTTA GTAATTTTCT
48201 CAAGTGAAAA AGAATTCAAT AACTTGCAAA TAGAAACTGA GATCAAATTT
48251 CCAAATAAAG TATATTGAAT TTTTGTTTAA ACTTTTAAAA TCTCAAGCTT
48301 AAAGCTTTGA ACATAAGATT AAAAAAACTT TTTTTAGTAT CCATTTTGTT
48351 GGCTTTAGTT AAATATCATA CAAAGTAACC AACCATCTGG TAACTTTCAC
48401 CTTAGAGAAA ACATGATAGT GGTTGTCACC TATTTCTTCT ATTGTTTTCT
48451 CTTCATTATC TTTGCTTTCT TTTCACTGCA CTTTGCCAGC CAACAGAGGA
48501 TGTATGGGTA CATGTGACTC ACACCCACTT GTTTACACAT GCATCTGTGC
48551 AAATACATAA GATGGTAGGT TAAAAAAAGA AGAATTAGTT TCTTGTCCCC
48601 TGGCCTTCTC CCACAAAAGA AGAATTAGTC CAGTTGGTTT TTCAAAATGG
48651 ATTCCAGGAT TCTTAGTGTT CCCTCGGGCT CAGGGTGGTT GATAGGAAAA
48701 GCCTATAATC CTCTCAGTCA CTTTTCAGTT TGTTTAGGGA ATGGATCAAA
48751 GAAGGAAGAT TTTACTGGGT GGCATGATTT TTTTATTATA TGAGGGAAAA
48801 TAGCACTTCA CTGTCTTTTG TTTAAAGACA AGCTTAACAG ATGCTAAAAA
48851 GTACATCTCT CAGCCAGATT CCTAGTCAAC AAGCTGATAG ACACTAAGAT
48901 TCTGGATTCT TCATTGATTA TATTCAGTCA TTGTTGGGCA ATTGACTCCC
48951 TGCCATAATA ATTGGGCCAG TATCTATAAC CAGCATTTTA CAGATGGATT
49001 CGCTAGACTC TTTCTGTAAG AGATGTTTCT AAAAAGAGTT ATAGTGAGAT
49051 ATGCTTCTAA GAAAAGTTAT ACTGTAGTAG TGTAATGAAA GCTACTAGTG
49101 TTTTATTAGT ATTTCACAAG AACAATGTTA CTCTGTCTCC CATATATAAC
49151 TGTCTATGGG CTTTTATGAT TATTCTTTAA AAAAAAAAAA TACTAAGGTA
49201 ATGCCTACCG GGGAACTCAT GGTGCTGGCT TCATCCAAAG TCTGAGCTGT
49251 TTTGGCTTTA TACTCCGAAA GACTTTATTT TCATACATCT TAACTAAAAA
49301 CTGGGGCTTT AAATTGGTCA TTCAAGGCCA GGCGCGGTTG CTCATGCCTG
49351 AAATCCCAGC ACTTTGGGAG GCCGAGGTGG GCAGATCACG AGGTCAGGAG
49401 ATTGAGACCA TCCTGGCCAA CACGGTGAAA CCCCGTCTCT ACTAAAAATA
49451 CAACAACAAC AACAACAAAA ATAGCCAGGC GTGGTGGCTT GCATCTGTAA
```

FIGURE 3R

49501 TCCCAGCTAC TCAGGAGGCT GAGGCAGGAG AATGGTGTGA ACCTGGGAGG
49551 CAGAGCTTGC AGTGAGCCGA GATCGCATCA CTGCACTCCA GCCTGGGCGA
49601 CAGAGCGAGA CTCCGTCTCA AAAAAAAAAA ACATCGGTAA TTCAAAGCAT
49651 AGACCAGCCC TTTTTCAAGT GATGTTGTTC CCATGACAAT CCATCAGTGA
49701 AAAACCAAAT ACCATATTCC AAGCTGCTAG TCACAGAGAA AACAAGCAGA
49751 TGAGATGAAT GTAATAGAAA AGACTAGAGT TAGTTTTGGG GTCATCTTTA
49801 GCCAACATTC CATTGCCTGA AGCTCAGTAA TCTGAATCCT TTTTAATTTG
49851 AGCACATCAG GGAACAGCTG AATACCCATG CTGAGGCATA ATTTAAGCTG
49901 TCAAGTGTCT CCTGTCAATA TACATGTGGT CATCTGATGC AAGGCAAAGA
49951 GACAGTCACT CCTGCTTCTT TATATCCCTA GCTCCCAACA TGGTGTCCTA
50001 ATGCATGATA ATCATGCAGT AAATGTTCAG TGATGAGAAC ATGACTTTGA
50051 GCAAGGCTGT ATGATCTGCC TCAGAACAAG TGAGTCAGTA AGAATGCAGG
50101 CCCCGGACCA TAGGAATGTA TTACAGTTTT GCCCAAGAAA CCACAAACGT
50151 TGGAAACACT CAAGTTTCTT TCTCGTATAC ATCAGCTGGT GTCATGCAAT
50201 GGGACATACC ATCTGACGCT TCCCTGTTCT TCCCTGATTT GTCCTGCATG
50251 TCTCCAATAC CTCTTTCCAA CCACCTCATC TCCCCACCTC ACCTTTCTTT
50301 TTCTTTGTTT GGCTTTATAT AGGTGCTGGG AGTCCCTACA GAGGATACTT
50351 GGCCGGGAGT CTCCAAGCTA CCTAACTACA ATCCAGGTAA TATTGATCTG
50401 AGCTTCTGAA TACTCTGAGA ATTAGTAATG TAAGGAGAGC ATTGGCCACG
50451 CTAACAGGGC GTTCTTGTAT TGTGAACTCA GCGGCAAAGA TGGGTGTAGA
50501 GGAATTTCTA CATTCATATA TTCCCTGACT AATCTTTGTA TGAGGAAGAC
50551 ACTGAAAGAG TAGCTGAGGT TAGACCAGTT CCCCAGCTCT GTAAAACACA
50601 AGTAGCAAGC TGAATAGAAT TTGAAATGAC TATTACTGTG GATTCCACAT
50651 CCATTGTCAA ATACCCAATG GCTCAAAAGA ACAACTCAAA AGATGGGCTC
50701 ACTTTTGGGC CCCCTGACTG TCATAAGTGT ATTGATTAGT ATTGAATTGC
50751 ATATGTATAA AAAGAAAGCT AATGCAACAG AACAGAGGTA GAGGCTCGCT
50801 AGGCCTAGGA CATGCCAAGT AAGCTGTCTG TAGGTTATAC TTACTAAGAG
50851 TTCATTCATT GCCTGTAAAC CTGACACTTG GTCATTGTCT CTCACACATT
50901 TCATCTTTCA AGACTGGCTT CTGGGATCGA TTTAGAAGTG CTGGAAGTGT
50951 TATCCATGGG GGAATTCTTT GAGAAGCTGT CGCAGGGCCA CATCAGAGGG
51001 ATCAGATTAA GCAGTAGTCA CTTCAAGGAT GTTGAGACAG AGGGGAGGAG
51051 ACAGGCACTG AACTACAGGA TGAAGGATCA TATTAGAAGC TGAAGAAGCA
51101 AATAAAGCCC ATGCCAAAGC TGAGCTCTCA CTGGCAGGGT TGAAGGGGAG
51151 GTAGAAAGGT ACAGATAACG ACAAGATTAG GGTGGATATG CTCCAAGCCA
51201 GATTTTTCTA GTCTTTATGG TCTTACATTG TTCCATTACT AAAAATGAAA
51251 TCTTCCCAAA TTGTTGTCCT TACTTTTTTT TTTTTTTTTT TGAGATGGAG
51301 TTTTGCTCTT ATCGCCCAGG CTGGAGTGCA GTGGCACGAT CTCGGCTCAC
51351 TGCAACCTCC ACCTCCTGGG TTCAAGCAAT TCTCCTGCCT CAGCCTCCCC
51401 AAGTAGCTGG GACTACAGGC ACCCGCCACC ATGCCCAGCT AATTTTTTGT
51451 ATTTTTAGTA GAGATGAGGT TTCACCATGT TGGCCAGGCT GGTCTCGAAC
51501 TCCTGACCTC AGGTGATCCA CTTGCTTCAG CTTCCCAAAA TGCTGGGATT
51551 ACAGGCATGA GCCAGCGCGC CTGGCCTGTT GTCCTTACTA ACTTTGGTAT
51601 GAGATTATCC TGGAAGGGTT TCCTGAGAGC AAGAAATTGT AGGTAGAGTT
51651 AAAATGTGAT TAAAGAAGAG AATAAAATAC ATAGGGAGCT GGGGACTCTT
51701 TTTCTTATTT TCTTTAGCAT CCAATACTTT TGCTTACAGC TATCCATAGG
51751 GATCTGGCAT CTTGAACCAC CAGGATTATG GAAGCCCTAC AGCAAGCTAA
51801 AGACTAACTG TAAAGTCCTT TCAGCTGCTT TGTGAATGGT TATATCTATT
51851 GCTAAAAGGC CTTAATATCA TTTGCAAATA GTTTATGATT TCTAACTATT
51901 TTTCTAGAGT TTAACACGTG AGAAAAATGC TACTCTCTGG TCACAGGACT
51951 TAGAATAGTG CCTATTTCCA TTGGTCTGAG ATAGAGAAAA AAGAACAAGT
52001 TTCTTGTGGA GCCGTGGTCC AGTCTGCAAA TTGCTCCTAT CTCCAGTTGC
52051 CATGGTTTCC AGGAGAACGT GGCTCTCATC TTTTCCTGCC CTGCCTGTAC
52101 TTCTCCCTGT CCACTCTGTT CTCTATTTTC CCTCAGCTTC CTAACTGAGG
52151 ATGCCAGCAG AAGTTTAGAG TCACAGATGG ATTGTAGGAA ACAATTTGGA
52201 TGATGCCAAT ACAAAGCTAC TGTGGTGGGC ATATGCTGCT CCCCCAAACT

FIGURE 3S

```
52251 TCAGACATTT GGGTTTCAGG TTGGTCCAGG CAATCAACAG TGATCCTTAA
52301 TACAAAATGT CTTGGTGAGA GCAATAATCA AGAAACTTGG CCAAAGTGCT
52351 TCCCTGCCAG ATTGTGTGCT TAATAAGATA ACTGGGTTCC AATAAAACAG
52401 AGAAAATATG TTACATTTTA AAAAATTTTC TGTTGTTTCA AAACAATGTG
52451 CAGTTTTTCT ATATAAGAAG AAAAGTCTCC AGGCCCAACA TCCATAGGGC
52501 TCATCATCCA TTGTTTTTCT TTTAAGTTTT CAATTTAATC CAAATAAGTC
52551 AAAAATTTTC AGGTACCTAC TATCTGCCAG GTGCTGTGCC GTGCGCTGGG
52601 GCTACACAGA TGGAGAGGGT GCATTCTTGG ATCTCTAGTG TTTGGGTTTG
52651 GATTCATTCA CCCACACTCT TTCACCAGTT CTCTTTGTTA CTGGGGTGCT
52701 CATTTGTGAG CCCTGCTTCC ATGGCTTGGA GAGTTTGTGG CTGTGGGCCA
52751 GGCTGAGCTT ATGGAGCAAA GGGAGTTGGA ACCTTAGCCA TAGACATGAT
52801 GTCTAAACCT GGATTTGGAA ATCTTAAAAG TCCAGCCTAT CTTGGGCCAT
52851 GGGGTCAGTA TTATTGATAA CTCAATCCCA AGGACTGTGT TTTAAAAGGG
52901 TCTCCAACAT CTGCATTTCA GGAACATCCT CTTACGTGAG TCAATAAGTT
52951 CCTTTTGAGC CACCCCCTAC CCATCCCCAT CCCTGAGCTG CTGTGGCTTC
53001 TAAACACTTG AATGTCAGTG ATTAAGGGGA GCAGAAGACA AGCTGGGAGC
53051 CAGGAAAGTG TCACAGATGA GCACCGTGTC AGCAGCATTC TGGATGAGCT
53101 TCCCATTCCT TTCCTTTTCA TTCTAAGTAG TCCTAGGAGC CCCCAAACTT
53151 TGAATCAGCC AGTACAATTT TGAGGGAGTC CAGTTGTCCG GAACTTGGGA
53201 GAACCATCCA GTGTCCATCT ACACCCATGC CTCCATTTCT AGGCCTTATC
53251 TGGACACCTC TAGGAGGACA GCAAAGTTTC CATTTGTACA GCTTTTAAAA
53301 AGTCACCTGA TGCTGACCCA GTCGGATTTC TC (SEQ ID NO:3)
```

FEATURES:

```
Start:   2118
Exon:    2118-2240
Intron:  2241-2946
Exon:    2947-3096
Intron:  3097-3310
Exon:    3311-3405
Intron:  3406-7938
Exon:    7939-8018
Intron:  8019-18260
Exon:    18261-18355
Intron:  18356-19116
Exon:    19117-19179
Intron:  19180-29296
Exon:    29297-29420
Intron:  29421-31091
Exon:    31092-31212
Intron:  31213-42825
Exon:    42826-42919
Intron:  42920-50322
Exon:    50323-50406
Stop:    50407
```

CHROMOSOME MAP POSITION:
Chromosome 2

ALLELIC VARIANTS (SNPs):

FIGURE 3T

| DNA Position | Major | Minor | Domain |
|---|---|---|---|
| 864 | C | T | Beyond ORF(5') |
| 2111 | C | G | Beyond ORF(5') |
| 3259 | C | T | Intron |
| 3673 | A | G | Intron |
| 3747 | A | G | Intron |
| 3788 | T | G | Intron |
| 8034 | T | A | Intron |
| 27740 | G | C | Intron |
| 27752 | C | T | Intron |
| 29927 | T | C | Intron |
| 30772 | A | G | Intron |
| 36310 | T | G | Intron |
| 36327 | T | C | Intron |
| 40618 | T | C | Intron |
| 40928 | T | C | Intron |
| 41044 | A | - | Intron |
| 41311 | - | G A | Intron |
| 41313 | - | A G | Intron |
| 44701 | C | A | Intron |
| 46020 | T | C | Intron |
| 46036 | A | G | Intron |
| 46095 | T | A | Intron |
| 47608 | T | G | Intron |
| 51949 | - | C | Beyond ORF(3') |
| 52150 | G | A | Beyond ORF(3') |
| 52426 | - | T | Beyond ORF(3') |

Additional SNPs 3' of the ORF (DNA positions refer to the genomic sequence provided in U.S. Serial No. 60/265,151, Attorney Docket No.CL001098-PROV, filed January 31, 2001):

| | | |
|---|---|---|
| 56707 | - | T |
| 57444 | A | G |
| 58021 | A | G |
| 58064 | A | C |
| 59067 | T | C G |
| 60034 | A | G |
| 63709 | A | T |
| 63817 | G | A |
| 64845 | A | - |
| 64848 | G | - |
| 64914 | G | T |
| 67367 | G | A |
| 67497 | T | A |
| 68252 | G | - |
| 68580 | C | G |
| 69990 | G | A |
| 71472 | A | G |
| 71664 | T | A |
| 71677 | A | G |
| 72590 | T | C |
| 72757 | G | C |
| 72863 | A | C |
| 74565 | C | T |

FIGURE 3U

| | | |
|---|---|---|
| 74850 | A | G |
| 75462 | G | C |
| 76045 | A | G |
| 79973 | G | A |
| 83181 | - | T |
| 84935 | C | T |
| 87476 | C | G |

Context:

DNA
Position

864 ATATTCTGAGAAACTAGCTTCTCACTCTCTCAGTTGTCAGTCAAAACTTTAATGGTCTTT
GGCCGGGTGCGGTGGCTCACGCCTGTAATCCCAGCACTTTGGGAGGCCGAGGCGGGTGGA
TCACAAGGTTAGGAGATCGAGACCATCCTGGCTAACACGGTGAAACCCTCGTCTCTACTAA
AAATACAAAAAATTAGCCGGGTGCGGTGCCAGACGCCTGTAGTCCCAGCTGCTCAGGAGG
CTGAGGCAGGAGAATGGTGTGAACCCGGGAGGCGGAGCTTGCAGTGAGCCGAGATTGCGC
[C,T]
ACTGCACTCCAGCCTGGGCGACAGTGCGAGACTCTGTCTCAAAAAAAAAAAAAAAAAAAA
GTTGAATGGTCTTTGAGCCAAGTAGTCTTCCTTTTCTTCTTCTTCTTTTTTTTTTTTTTT
CAAAAAATATCTCTAGATTGAATCTTGGAATTGGCTTAAGTCTCTTCTCTTGTGGCAATT
TTGAAATGAAAAAATACATGCTCATAATTAAATTACCTGAACATTTTAAAAAACCATCAT
GAGGTTCAAATATCAAATATTCATAAATATTGTTGTGATAATAGACATAACTCTTATTTT

2111 TACCAATAGCACTAACTTGTGGCCAGAACAAGAACCTTAACTGTGCCAAATTTTATTCTA
TTCAATAACAGCTGCCTCGTTTTCAGTTGTGCACATCTGAATGCAAGCAATCCCTGTCTG
ATGTGGAGTTTCTTGCACTGATAAGGAAAAACTGCTGAAGTTGTGAGGCTGCTCCAGGCA
GAGCCATCATGTGAGTCATATGAAAGCTCCACGCTGCTGACCTCTGGCAAAAAGGGAGAG
AACAAGGATAGGAGAGGCAGTGGGGGAAAGGTTCAAGTGCGGGTTTTCTCCTTGAACCTA
[C,G]
AAGATTATGGGTCAAGAGCTGTGTGCAAAGACTGTACAGCCTGGATGCAGCTGCTACCAT
TGTTCAGAGGGAGGCGAGGCACACAGCTGTCGGAGGAGTCAGCCTGAGACCACGGAGGCT
GCGTTCAAGGTATTTGTATCCCAGGAGAGAGCATCTTTCTCTATTGATAAACCAAGGAGT
TCAGACACTCCCTTTTTGTAGCGGGATCTGATTCTTCTGCGGTAGGTCTAAACCAATAAA
ATGAAAATTCTATTAAAGTCACAGAAAATTTATGGCTGTAGTTATCAAATTTGGGGAATT

3259 AAAGAAGCATCATGTTCCATGACTTCATTTCACCCCAGGGGACTTCAAGCTGCCCGTGCC
CAGAAGTTCAAGAGTAAAAGGCCACGGAGTAACAGTGATTGTTTTCAGGAAGAGGATCTG
AGGCAGGGTTTTCAGTGGGTGAGTGAGCAGCTGATGTTGATCAAGAAGAATTTAATGTGA
GCTTGTCTACGGAGGCCGGCCCTTGCTTCCAGGGCAATTACTGAGCGAGCCTTCCCAAGT
CTGCTCTGGCAATGCTGTCTAATTTCCCTGGGGAAAAAAAGTCAACACTAAAAAAAAGTG
[C,T]
TCTTTCTCTCTTCCCTTTCACCCGCTCCTTTTCCCCATTCCCCTAGAGCAGAGGAAGAGC
CTCCCTTTTGGGGCAGCCTCATCTTACTTGAACTTGGAGAAGCTGGGTGAAGGCTCTTAT
GCGACAGTTTACAAGGGGATTAGCAGGTGAGTGACACATAGCTGGGAGAGACTTTAGAGA
TGAGAGTCCCGCCCCCCCAATTTCATATTATAAAGCCAGGTGAGACATCATAGAAGTTCA
TAGCACTCAGGACCTGTGCAAGACACCATGGCCGACAGGGAGAGAGACATGATAACTTAA

3673 CTCTTATGCGACAGTTTACAAGGGGATTAGCAGGTGAGTGACACATAGCTGGGAGAGACT
TTAGAGATGAGAGTCCCGCCCCCCCAATTTCATATTATAAAGCCAGGTGAGACATCATAG
AAGTTCATAGCACTCAGGACCTGTGCAAGACACCATGGCCGACAGGGAGAGAGACATGAT
AACTTAAACAGCCTTGAAAGAAAAACAAACCTGCCCTGCCCTAATTAAAATCAGCCCACT
TAAATGTTTATCAGCCTTTCCCTTCTTGCATTCAATTCAGAGAATTCAAAGAAAATAGAC
[A,G]
TTCTCTACTACTGACCCAAAGAACAATTATCACTCTTCAGGCCTGTGGGAGGCACAGTTG
GTAAAGCGTCTCTAACAGGTTTTTTATATCCCTCCCTAAATCACAATGACAGAGTTTTGT
AATGGCAACCTGGAATTTGCTGCTTCATTCCTCCACCTGGCCTTTATAGAAGAAACTGAA
GTTGGTTTCTGCAAATTATGGTACATGCAAAAGATGATAAATCCTAGATTTTTTATATTT
GCAAAATACACAAAATGTCTGGAGAATAAAAATACTGCTTATCCAAAAGCTAAGTACTAA

FIGURE 3V

3747
CCCGCCCCCCCAATTTCATATTATAAAGCCAGGTGAGACATCATAGAAGTTCATAGCACT
CAGGACCTGTGCAAGACACCATGGCCGACAGGGAGAGAGACATGATAACTTAAACAGCCT
TGAAAGAAAAACAAACCTGCCCTGCCCTAATTAAAATCAGCCCACTTAAATGTTTATCAG
CCTTTCCCTTCTTGCATTCAATTCAGAGAATTCAAAGAAAATAGACATTCTCTACTACTG
ACCCAAAGAACAATTATCACTCTTCAGGCCTGTGGGAGGCACAGTTGGTAAAGCGTCTCT
[A,G]
ACAGGTTTTTTATATCCCTCCCTAAATCACAATGACAGAGTTTTGTAATGGCAACCTGGA
ATTTGCTGCTTCATTCCTCCACCTGGCCTTTATAGAAGAAACTGAAGTTGGTTTCTGCAA
ATTATGGTACATGCAAAAGATGATAAATCCTAGATTTTTTATATTTGCAAAATACACAAA
ATGTCTGGAGAATAAAAATACTGCTTATCCAAAAGCTAAGTACTAATTTTGGTAAACAAC
CAACTTTGTTAAATATATGTAAAAGATCCATGAATTCCCCTTTTAGTCAAGGTGGGAAAG

3788
CATAGAAGTTCATAGCACTCAGGACCTGTGCAAGACACCATGGCCGACAGGGAGAGAGAC
ATGATAACTTAAACAGCCTTGAAAGAAAAACAAACCTGCCCTGCCCTAATTAAAATCAGC
CCACTTAAATGTTTATCAGCCTTTCCCTTCTTGCATTCAATTCAGAGAATTCAAAGAAAA
TAGACATTCTCTACTACTGACCCAAAGAACAATTATCACTCTTCAGGCCTGTGGGAGGCA
CAGTTGGTAAAGCGTCTCTAACAGGTTTTTTATATCCCTCCCTAAATCACAATGACAGAG
[T,G]
TTTGTAATGGCAACCTGGAATTTGCTGCTTCATTCCTCCACCTGGCCTTTATAGAAGAAA
CTGAAGTTGGTTTCTGCAAATTATGGTACATGCAAAAGATGATAAATCCTAGATTTTTTA
TATTTGCAAAATACACAAAATGTCTGGAGAATAAAAATACTGCTTATCCAAAAGCTAAGT
ACTAATTTTGGTAAACAACCAACTTTGTTAAATATATGTAAAAGATCCATGAATTCCCCT
TTTAGTCAAGGTGGGAAAGTTGGATGGTCGCTTTTTTTCTTTATGTTACTCCAATAGAGAG

8034
CACTTTAGTAAAGAGGGAAAATGCTTTGGAATATATATGTTATATATGTATTGATACATG
TTAAACTTTTTATTTTGAGAAAATTATAGATTTATATGCTAGAATATATTTTGAAGTGAA
AGTGCTTTTGTTAAGCCATCTTTGGTATAAATTGCTGCTTTGAACCACCTCAATAAGTGT
GTGCCCCTCAATCCCTCTCTTCTAGAATAAATGGACAACTAGTGGCTTTAAAAGTCATCA
GCATGAATGCAGAGGAAGGAGTCCCATTTACAGCTATCCGAGAAGGTAAGAACAGCAGAA
[T,A]
TGGACCCAATAGATCTGTTTTGAGTCCTTGATTTGGTAAAAAATGTATTGCATTGATCCA
TTCAGCATCTAGTTTTGATTCTTCTGGAATACTATAATTACATTTTTTATTTTTCATACAA
GTTTTTCAAGAAATTTACACTGCTATTTTATTACTTAATTTTGAGGAAATTGAGATTTAA
AACTATTATATCACTTGACCAAAACTATAAATTCACTGAGCAATTACTAATACTTTCCAT
GTGTTTGGCCTCATGCTAGGTGCTAAGGCTATACCTATATAACCTCAGAAAATTCCTATA

27740
CCTGTCTTCTATCCACCTGTCTTCCTCTTCCTCTTTCCCTAGTCCTGCATATTGAAAAAC
ATTTTTTTTTTTTTTTTGAGATGGAGTCTTGCTCTGCCACCCAGGCTGGAGTGCAGAGGCA
CGATCCTGGCTCACTGCAACCTCTGCCTTCCAGGTTCAAGCAATTCTCCTGCCTCAGCCT
CCCGAGTAGCTGGGATTATAAGCATATACCACCACATCTGGCTAATTTTTGTATTTTTAG
TAGAGATGGAGTTTCACCACATTGGCCAGGCTGGTCTCGAACTCCTGACCTCAGGTGATC
[G,C]
GCTCGCTTTGGCCTTCCAAAGTGCTGGGATTATAGGCGTGGGCCACTGCGCCAGTCTGAA
AAACGTATTTTTAAGCACATACTATCGTATCTTCTTGTCTTTTACCTGGAATTTAAGCTG
GTTGTTTGTATTACCTTTTCCATGGACATTTATATTTATAACCAATCAGAAGGTTTAAAT
GTCAGTGTAGGAATTTTTGTGCTATGGAAGCTTCGTGGCTTGGTGAATGGTAAAATGAATA
ATGTGTGTATATTTGAAGCATCAGAAAGAGAAAATGCTGGGAAGATTCATAGAACCAGTT

27752
CCACCTGTCTTCCTCTTCCTCTTTCCCTAGTCCTGCATATTGAAAAACATTTTTTTTTTT
TTTTGAGATGGAGTCTTGCTCTGCCACCCAGGCTGGAGTGCAGAGGCACGATCCTGGCTC
ACTGCAACCTCTGCCTTCCAGGTTCAAGCAATTCTCCTGCCTCAGCCTCCCGAGTAGCTG
GGATTATAAGCATATACCACCACATCTGGCTAATTTTTGTATTTTTAGTAGAGATGGAGT
TTCACCACATTGGCCAGGCTGGTCTCGAACTCCTGACCTCAGGTGATCGGCTCGCTTTGG
[C,T]
CTTCCAAAGTGCTGGGATTATAGGCGTGGGCCACTGCGCCAGTCTGAAAAACGTATTTTT
AAGCACATACTATCGTATCTTCTTGTCTTTTACCTGGAATTTAAGCTGGTTGTTTGTATT
ACCTTTTCCATGGACATTTATATTTATAACCAATCAGAAGGTTTAAATGTCAGTGTAGGA
ATTTTGTGCTATGGAAGCTTCGTGGCTTGGTGAATGGTAAAATGAATAATGTGTGTATAT
TTGAAGCATCAGAAAGAGAAAATGCTGGGAAGATTCATAGAACCAGTTAACATTTGAACT

29927
TAGTCAGATGGCCAAAAGCTGGGCACCCTTGCTGCCCCACTGCCAGTTTTGATATAGAGA

FIGURE 3W

CATTGGTAGAGTAAACTGTACTTAGTAAGTTTTCCTAAATCTAAGTGAATATACAAATTA
TATTGGAATAGATTGAGATTATCCCAAGATGATAAAGAGGTTAACCCCAGATTGTAGCAT
GGACTCCTGTCAGGATGGAGACTCCAGGACACTTGTTCCTGCTCTCCTACCTTCTTTATA
TAAGTGTGAGATGCAAAGTTTTATTCCCATTAAAGTGAAGCAGATTTCCTCTAAGTATCA
[T,C]
TGTATCCTTCCATTTTAGCACTTATCGCAGTTTATAATTATATTCACACACATAAATACA
TACATGCATACATACAAATATATATACATGTGTGAGCACACCCCCACACACAAATATATA
TAGATTTGCGTGATGATTTTGTCTCAACTGGACTGTAAGCATAATGAGGGCAGCCTGGGT
TTGTTTTTGCTTATCATTTTATCCTTAGTGCCTGGTACCATAGTAGGTGCTTAATAAGTA
CTTGTTGAAAAACTGGCTCTATGTGAGCTAAGGAACCACTCTTCTCTGTTTGGCAGATGC

30772
CAGTCCCTACCGTTTATCTACTAAACTGGGCTTTCCTGGAGTGCCAAAACGGAAGGTGGC
CATGTTAGTCATGAACAGCTCAGTTTCTGTTACAGAGACCCAAAATTACAGAGGTATAAC
ATGCTAGAAACTTAACTTTCTTTCGCATCACAGTCCTGACCTAAGCAGGCAGAGCATGTA
TGGTGGCCCCATGCTATCTTGGCCCAGGCTGCTTCTGTCACGTGGCTCCTCCATCCCCAA
TTGTATGTTTCAAGATGGCTGCCACTTCCTGCTCATCACAGCCCAGAGGAGGGAGAAAAG
[A,G]
GAAGCAGAACCCTTAACCCCTCCACTAAGGCATAATCTGGAAGTTCACACATCACCTCTG
TTCATATCATATAGGCAAGAACTTAGTCACCTGACCACACCCAGCTGCCAAGAAGGCCAC
ATCTAGCTGCAAAGCAGGCCAAAATTTGAGAAATTCACTTGATGAAGTGATAGACAAGAG
TCAAGATAGTGATTAGTTCTACTAAAAGCACCTAAAGTTTGTGTGTTATTTTTTCTAATG
GTGTTTACCCTGGTCCAGTGCATCATGGTGCAAGCCAAGGTCCAGAACGATGGGTTTTAT

36310
TAGAGTGTTTTGTTTTGTTTGTGTGTGTGTAGGCCTGCTGGTGGCAAATTCTTCGTTTTT
GTTTTCAGAAGATAAACCCTAATTATTGAAAGGTGGTTTTGTTGGGGATGTGATTCTAGA
CTGACAGTTATTTTCTCTCAGAACTTTGAAGATGTCATTCCCCTTCTTTGTCTTCCATTG
TTGCTGTCGAGGAGTTTGCTTTTAGCCTTATTATCTTCCTTTTGCAGGTGATCTCATTTT
CTCTGGATGTTTTAAAGACTTTTTTCTTTGCCTTTATGATTATGCAGTTTTCTCTAGGAG
[T,G]
TGTCCAGTGTGGATTTCTTTTTACTTACCCTGTTTGGTATATCTTGTGTTTCTTCCATTT
GTGAATTCATGTCTTTCATCAGCCATTTTCTTTTTGAATATTGACTCTATTCTATTCTCT
CTCTGTAGAGCTCCAATGAAAGACTATTAGACCACATTCTTCTGTTATCCATTTCTCTTC
TCTCCTTCATATTTTCCATTTCCTTAACTTTCTGTGATGCATTCTGGGTAATTTCTTCAG
CTCATCTACCAGTTCTTTAAGTCTCTCTTAAACTATGTATTAGGTTGGTGCAAAAGTAAT

36327
TTTGTGTGTGTGTAGGCCTGCTGGTGGCAAATTCTTCGTTTTTGTTTTCAGAAGATAAAC
CCTAATTATTGAAAGGTGGTTTTGTTGGGGATGTGATTCTAGACTGACAGTTATTTTCTC
TCAGAACTTTGAAGATGTCATTCCCCTTCTTTGTCTTCCATTGTTGCTGTCGAGGAGTTT
GCTTTTAGCCTTATTATCTTCCTTTTGCAGGTGATCTCATTTTCTCTGGATGTTTTAAAG
ACTTTTTTCTTTGCCTTTATGATTATGCAGTTTTCTCTAGGAGTTGTCCAGTGTGGATTT
[T,C]
TTTTTACTTACCCTGTTTGGTATATCTTGTGTTTCTTCCATTTGTGAATTCATGTCTTTC
ATCAGCCATTTTCTTTTTGAATATTGACTCTATTCTATTCTCTCTCTGTAGAGCTCCAAT
GAAAGACTATTAGACCACATTCTTCTGTTATCCATTTCTCTTCTCTCCTTCATATTTTCC
ATTTCCTTAACTTTCTGTGATGCATTCTGGGTAATTTCTTCAGCTCATCTACCAGTTCTT
TAAGTCTCTCTTAAACTATGTATTAGGTTGGTGCAAAAGTAATTGCAGTTTTTGCCATTA

40618
CCGGGTGTGGTGGCTCACACCTGTAATTCCAGCACTTTGGAAGGCTGAGGCAGGCGGATC
AATTGAGGCCAAGAGTTTGAGACCAGCCTGGCGAACATGGTGAAACCCTGTCTGTACTAA
AAATACAAAAATTAGCCAGGCATGCTGGTGCATGCCTGTAATCCCAGTTACTCAGGAGGC
TGAGGCAGGAGAATCACTTGAACCTGGGAGGTGGAGGTTGCAGTGAGCTGAGATTGCACC
ACTGCACTCCAGCCTGAGTGACAGAGTGAGACCCTGTCTCAAAAAAAAAGAAAAAAAAAA
[T,C]
TGGCAATAAAAACAACCTGTTGCTTGCTGGAGGAAAAACCTGCTTGCAAAGCTCAGTCTG
ATATCATTTTTTAAACAAAACTCTAAGAACAAGCCAGTCAGTTAAGCTAAAACCAAATAT
TTGATTATGAAAAGGGTTTTTGTATATTTTTACAGGATAAGATACAAATAAATTTCAGTC
TTTCTTTTAATATGTATTTCTGTTCCCAAACCAGACACAAAGCAATTTTTAAACTTGATC
GTCAAGAAATCTGTTTTCTCCTACACAATCAATGAAAAGTAATCTAAACAGTGTTTGTCA

40928
AAACAACCTGTTGCTTGCTGGAGGAAAAACCTGCTTGCAAAGCTCAGTCTGATATCATTT
TTTAAACAAAACTCTAAGAACAAGCCAGTCAGTTAAGCTAAAACCAAATATTTGATTATG

FIGURE 3X

AAAAGGGTTTTTGTATATTTTTACAGGATAAGATACAAATAAATTTCAGTCTTTCTTTTA
ATATGTATTTCTGTTCCCAAACCAGACACAAAGCAATTTTTAAACTTGATCGTCAAGAAA
TCTGTTTTCTCCTACACAATCAATGAAAAGTAATCTAAACAGTGTTTGTCAGGCCAGGCA
[T,C]
AGTGGCTCACATCTGTAGTCCTAGCATTTTGGGAGGCCTAGGCAGGTAGATTGCTTGAGC
CCAGAATTTCAAGACCAGCCTGGACAACATGGCGAAACCCCATCTGTATTAAAAAAAAAA
AAAAAAAAAAGACCATATGTCTGCAGTCAGATGGAAAAAGTAAAAATATGTAATAAACACA
TATGAATAATATTAAGGACCATATTTTAAAATAAACTTGATAATAAATTTTTAATAATAT
TATCTACGATAAAATGTTTTACTTAAATTTCGTTCTTTATCATGCCACACAAAAATGGCA

41044

TATGAAAAGGGTTTTTGTATATTTTTACAGGATAAGATACAAATAAATTTCAGTCTTTCT
TTTAATATGTATTTCTGTTCCCAAACCAGACACAAAGCAATTTTTAAACTTGATCGTCAA
GAAATCTGTTTTCTCCTACACAATCAATGAAAAGTAATCTAAACAGTGTTTGTCAGGCCA
GGCACAGTGGCTCACATCTGTAGTCCTAGCATTTTGGGAGGCCTAGGCAGGTAGATTGCT
TGAGCCCAGAATTTCAAGACCAGCCTGGACAACATGGCGAAACCCCATCTGTATTAAAAA
[A,-]
AAAAAAAAAAAAAGACCATATGTCTGCAGTCAGATGGAAAAAGTAAAAATATGTAATAAA
CACATATGAATAATATTAAGGACCATATTTTAAAATAAACTTGATAATAAATTTTTAATA
ATATTATCTACGATAAAATGTTTTACTTAAATTTCGTTCTTTATCATGCCACACAAAAAT
GGCAAAATGATTAAGAGAGTTTGCAAAATTATGTGGTATAGTGAAAGAGGTTTGCGGTTA
AAAAAAAAAAAGAGAGAGAGAGAGAGAGAAGTATGGGGCCATGGGGATAGTCTCTGTAATCA

41311

GACAACATGGCGAAACCCCATCTGTATTAAAAAAAAAAAAAAAAAAAAGACCATATGTCTG
CAGTCAGATGGAAAAAGTAAAAATATGTAATAAACACATATGAATAATATTAAGGACCAT
ATTTTAAAATAAACTTGATAATAAATTTTTAATAATATTATCTACGATAAAATGTTTTAC
TTAAATTTCGTTCTTTATCATGCCACACAAAAATGGCAAAATGATTAAGAGAGTTTGCAA
AATTATGTGGTATAGTGAAAGAGGTTTGCGGTTAAAAAAAAAAAAGAGAGAGAGAGAGAG
[-,G,A]
AGTATGGGGCCATGGGGATAGTCTCTGTAATCAGTCACCTGAACCACTTTTAATACTCAA
AAGACTTATGAGAATAAAAATCTGATTTTTGCTAAGATTTATTAGCAAAATAAATCTTAC
TCCTTCCTGTCCCTCTCTAATTATCCTTCAGCTTGACCATGTATGAAAGAAAATTTACAT
TTCACTGTTTAATCTATTTAAAGATGAACATTTCCCATTAAATCAGGATGCACCTTATAA
TCAGTAGCATCTAACAATATAAGTCAGCCAGGCTGCAGTTGTGACTGTAGTTAGAATTGC

41313

CAACATGGCGAAACCCCATCTGTATTAAAAAAAAAAAAAAAAAAAAGACCATATGTCTGCA
GTCAGATGGAAAAAGTAAAAATATGTAATAAACACATATGAATAATATTAAGGACCATAT
TTTAAAATAAACTTGATAATAAATTTTTAATAATATTATCTACGATAAAATGTTTTACTT
AAATTTCGTTCTTTATCATGCCACACAAAAATGGCAAAATGATTAAGAGAGTTTGCAAAA
TTATGTGGTATAGTGAAAGAGGTTTGCGGTTAAAAAAAAAAAAGAGAGAGAGAGAGAGAA
[-,A,G]
TATGGGGCCATGGGGATAGTCTCTGTAATCAGTCACCTGAACCACTTTTAATACTCAAAA
GACTTATGAGAATAAAAATCTGATTTTTGCTAAGATTTATTAGCAAAATAAATCTTACTC
CTTCCTGTCCCTCTCTAATTATCCTTCAGCTTGACCATGTATGAAAGAAAATTTACATTT
CACTGTTTAATCTATTTAAAGATGAACATTTCCCATTAAATCAGGATGCACCTTATAATC
AGTAGCATCTAACAATATAAGTCAGCCAGGCTGCAGTTGTGACTGTAGTTAGAATTGCAC

44701

TCTAAAAACTTTCTTGCAAGACAGAGCAATGCTATCTTCACATTATGTTATTGGGTGCTA
TAACATCATCTAAGCTGGAGACAGCCTACTGTCATAGCTTTGGAGTCCAAAGACCTGGGT
TTGAATTCTAACCATTTTCTAGCTAAATGAACATGGGCAAGTTATGTAGTCCCTCTGAAC
TTTCGTTTCCTTGTCTGTAAAATGGCAACAATGATAATAAGGACTTTCTAATTCTTTATT
GAGAATTCCATAAAAACAAATGCATAACAAGCTCCATGCACCATAAATGCTCAATAGATG
[C,A]
TTGCTTTCTTCCTGTCCCATACAAATTGTTGTACAGATGTTTCAATAACCTAACTGCTAG
CAAGTATTACCTGAAATTTAACCCGATTGTTCTCTTCTTTCACTTAGCAGTATTATTTCT
TGTCCACAATAGAGGAAGCACAATTGCAGTTCTGATGCTGCAATGACCTTTTATACATTT
GAAGAGTTTTTCCTGGTCATTTAATCAGGAAACAACACTTACTCACCATATATGAGGCGA
GTAACTCTACAAGACTCTACAAGGTCTTGTAAGAAGCTATAAGCCAAGGGGGAAAAAAAA

46020

AAATTTCAAATAACATTTTAAAATATGACATACTATCTTTGAATGACCACACAATTTAAA
AAGCAATCATTTTACGGTTCTTTAGTGTTCAGTTAGCACAGCACTTAGAAATCATAGAAT
AAAGTGAGCAAGATGCTTCTCAAAGCCTGATCACTCTTTAGGACTCACAATGGGCTAGGT

FIGURE 3Y

ACTATGCTGGAAAGAGAAAAAATAATAATTTTCTAACCTGCTTGAGACATAGTGGTATAA
ATGATAACACAGCTGCTGAACGTGATGACTTTCTCACTTTGTCCGCAGAGCAAGAAACTA
[T,C]
AGATGCAGTAACAAAACTGCATTCAATGAACATGGGACTGTAGATAACAAACTAACTTCA
TTTCTTTGGGTACATGCCCTGTATTGGGATTGCTGGATCATATGGTAGTTCCATTTTTAA
TATTTTGAGGAACCTCCATACCATCTTCCATAATGGCTGTGCTATTTGCATGCCCACCAT
CAGTGTGCAAATGCTCCCTTTCCTCCACATTCTTGCCAACACCTCTTTCATCTTTTTGAT
AATAGTTATGAGGCAATATCTCACCATGGTCCTAGACTTCATTTGTCTGATGACTAATGA

46036

TTTAAAATATGACATACTATCTTTGAATGACCACACAATTTAAAAAGCAATCATTTTACG
GTTCTTTAGTGTTCAGTTAGCACAGCACTTAGAAATCATAGAATAAAGTGAGCAAGATGC
TTCTCAAAGCCTGATCACTCTTTAGGACTCACAATGGGCTAGGTACTATGCTGGAAAGAG
AAAAAATAATAATTTTCTAACCTGCTTGAGACATAGTGGTATAAATGATAACACAGCTGC
TGAACGTGATGACTTTCTCACTTTGTCCGCAGAGCAAGAAACTATAGATGCAGTAACAAA
[A,G]
CTGCATTCAATGAACATGGGACTGTAGATAACAAACTAACTTCATTTCTTTGGGTACATG
CCCTGTATTGGGATTGCTGGATCATATGGTAGTTCCATTTTTAATATTTTGAGGAACCTC
CATACCATCTTCCATAATGGCTGTGCTATTTGCATGCCCACCATCAGTGTGCAAATGCTC
CCTTTCCTCCACATTCTTGCCAACACCTCTTTCATCTTTTTGATAATAGTTATGAGGCAA
TATCTCACCATGGTCCTAGACTTCATTTGTCTGATGACTAATGATATTGAGCATTTTTTC

46095

GGTTCTTTAGTGTTCAGTTAGCACAGCACTTAGAAATCATAGAATAAAGTGAGCAAGATG
CTTCTCAAAGCCTGATCACTCTTTAGGACTCACAATGGGCTAGGTACTATGCTGGAAAGA
GAAAAAATAATAATTTTCTAACCTGCTTGAGACATAGTGGTATAAATGATAACACAGCTG
CTGAACGTGATGACTTTCTCACTTTGTCCGCAGAGCAAGAAACTATAGATGCAGTAACAA
AACTGCATTCAATGAACATGGGACTGTAGATAACAAACTAACTTCATTTCTTTGGGTACA
[T,A]
GCCCTGTATTGGGATTGCTGGATCATATGGTAGTTCCATTTTTAATATTTTGAGGAACCT
CCATACCATCTTCCATAATGGCTGTGCTATTTGCATGCCCACCATCAGTGTGCAAATGCT
CCCTTTCCTCCACATTCTTGCCAACACCTCTTTCATCTTTTTGATAATAGTTATGAGGCA
ATATCTCACCATGGTCCTAGACTTCATTTGTCTGATGACTAATGATATTGAGCATTTTTT
CATATATCTCTTGGCCATTTGTAGGTCATCTTTTGAGAAATGTGTATTGAGGTTCTTAGT

47608

GTTAGCCAGGCTGATCTCGAACTCTCGACTTCTGGTGATCCACCTGCCTCAGCCTCCCAA
AGTGCTGAGATTACAGGCGTGAGCCACCGTGCCCGGCCCTTTGCCCACTGTTTAATGGGG
TTGTCTTCTTGCTATTGAGTTCCTTATATATTTTTTATATTAACCCCTTATCAAATGTAT
GGCTTGCAAATATTTTCTCCCATCGTAGGTTGTCTCTTCACTCTAATGATTGTTTCCTTT
GCTCTGAAGACACTTTTTAGTTTTATTTATTCCCATTTGTCTATTTTCACATTTGTTGCC
[T,G]
ATAAGCAGGTTAGAAAATTATACAGATTATAAATAGTTCCTGAATTTGTGTTTTACTAAA
CGTAGCCTACACAGATGAAAACAGGAAAGCTACACTTCAGAATCTGTGATATTTGATGTC
AGAAGTGCATCCCTGAAAGCAATGGGTCCATTCTAAATCTCCTAACCTCTAACCATAATT
TGTTCTATATTTATCCTGAGATCTCACTCTTAGGAATAAAAACACATTGAGAAGTCCTGA
GTCTCTATTTTACTATTTTTCTGAAGTGCCTGTAGTGTGTGTGTTTACATCTAAATAATA

51949

TTAAAATGTGATTAAAGAAGAGAATAAAATACATAGGGAGCTGGGGACTCTTTTTCTTAT
TTTCTTTAGCATCCAATACTTTTGCTTACAGCTATCCATAGGGATCTGGCATCTTGAACC
ACCAGGATTATGGAAGCCCTACAGCAAGCTAAAGACTAACTGTAAAGTCCTTTCAGCTGC
TTTGTGAATGGTTATATCTATTGCTAAAAGGCCTTAATATCATTTGCAAATAGTTTATGA
TTTCTAACTATTTTTCTAGAGTTTAACACGTGAGAAAAATGCTACTCTCTGGTCACAGGA
[-,C]
TTAGAATAGTGCCTATTTCCATTGGTCTGAGATAGAGAAAAAAGAACAAGTTTCTTGTGG
AGCCGTGGTCCAGTCTGCAAATTGCTCCTATCTCCAGTTGCCATGGTTTCCAGGAGAACG
TGGCTCTCATCTTTTCCTGCCCTGCCTGTACTTCTCCCTGTCCACTCTGTTCTCTATTTT
CCCTCAGCTTCCTAACTGAGGATGCCAGCAGAAGTTTAGAGTCACAGATGGATTGTAGGA
AACAATTTGGATGATGCCAATACAAAGCTACTGTGGTGGGCATATGCTGCTCCCCCAAAC

52150

TGCTAAAAGGCCTTAATATCATTTGCAAATAGTTTATGATTTCTAACTATTTTTCTAGAG
TTTAACACGTGAGAAAAATGCTACTCTCTGGTCACAGGACTTAGAATAGTGCCTATTTCC
ATTGGTCTGAGATAGAGAAAAAAGAACAAGTTTCTTGTGGAGCCGTGGTCCAGTCTGCAA
ATTGCTCCTATCTCCAGTTGCCATGGTTTCCAGGAGAACGTGGCTCTCATCTTTTCCTGC

FIGURE 3Z

CCTGCCTGTACTTCTCCCTGTCCACTCTGTTCTCTATTTTCCCTCAGCTTCCTAACTGAG
[G,A]
ATGCCAGCAGAAGTTTAGAGTCACAGATGGATTGTAGGAAACAATTTGGATGATGCCAAT
ACAAAGCTACTGTGGTGGGCATATGCTGCTCCCCCAAACTTCAGACATTTGGGTTTCAGG
TTGGTCCAGGCAATCAACAGTGATCCTTAATACAAAATGTCTTGGTGAGAGCAATAATCA
AGAAACTTGGCCAAAGTGCTTCCCTGCCAGATTGTGTGCTTAATAAGATAACTGGGTTCC
AATAAAACAGAGAAAATATGTTACATTTTAAAAAATTTTCTGTTGTTTCAAAACAATGTG

52426 TTTTCCCTCAGCTTCCTAACTGAGGATGCCAGCAGAAGTTTAGAGTCACAGATGGATTGT
AGGAAACAATTTGGATGATGCCAATACAAAGCTACTGTGGTGGGCATATGCTGCTCCCCC
AAACTTCAGACATTTGGGTTTCAGGTTGGTCCAGGCAATCAACAGTGATCCTTAATACAA
AATGTCTTGGTGAGAGCAATAATCAAGAAACTTGGCCAAAGTGCTTCCCTGCCAGATTGT
GTGCTTAATAAGATAACTGGGTTCCAATAAAACAGAGAAAATATGTTACATTTTAAAAAA
[-,T]
TTTCTGTTGTTTCAAAACAATGTGCAGTTTTTCTATATAAGAAGAAAAGTCTCCAGGCCC
AACATCCATAGGGCTCATCATCCATTGTTTTTCTTTTAAGTTTTCAATTTAATCCAAATA
AGTCAAAAATTTTCAGGTACCTACTATCTGCCAGGTGCTGTGCCGTGCGCTGGGGCTACA
CAGATGGAGAGGGTGCATTCTTGGATCTCTAGTGTTTGGGTTTGGATTCATTCACCCACA
CTCTTTCACCAGTTCTCTTTGTTACTGGGGTGCTCATTTGTGAGCCCTGCTTCCATGGCT

Additional SNPs 3' of the ORF (DNA positions refer to the genomic sequence provided in U.S. Serial No. 60/265,151, Attorney Docket No.CL001098-PROV, filed January 31, 2001):

56707 CTGCCAAGATCGATGCTGGGTGGAGTAGCCCGATTCTACAGATGAGGAAACAGAGGCTTT
CTCCTAGGCTCACAGAGAGGTGTATACTTATTGGAAATGGCTGAAATCTGCATCCAAACC
TTGTTCTCCTTTCATTAATCATGTTGTATCCCTCTGTCTCATTTTGCAGGATGAGTCTGA
AAAATAAATTATATTGAATTGCATCTGCTATAGTGCCTAACTTTTAGTAGGTACTCAATA
AAAGTTCCCATTCAGTTTTTTTTGTTGGTTTGTTTTTTTTTTTTTTCTTTTTTTTTTTTT
[-,T]
TTTAGATGAAGTCTCACTTGTCACCCAGGCTGGAGTGCAGTGGCATGATCTCGGCTCACC
GCAGCCTCCGCCTCCTGGGTATAAGCGGTTCTCCTGCTTCAGCCTCCCGAGTAGGTGGGA
ATACAGGCGCACGCCACTGAACCCAGCTAATTTTTGTATTTTTAGTAGAGACAGGGTTTC
ACCATGTTGGCTAGGCTGGTCTCGAACTCCTGACCTCAAGTGATCTACCTGCCTCAGCCT
CCCAAAGTGCTGGGATTACAGGTGTGAGCCACTGCCTCCATTTGGTTTTTTACACAGTGT

57444 CTTTTGTTTTTACTTGCATGGCCTAAACCTTGCCTGAATCCGCACATCCTAAGAGCTGAC
TCTGAGTTTTCAAATGCCTACCTAAGTCAGTTGTGTGCCCGTTAAGGCTGTTCTTATTTG
GTGATGGGTCCATTCTGCTCCCCACACCTAGACTGCAGTAATATGTCTGCCCACTCTGTA
CCCACAGGGCCTTTCCCTGGGAGAATCCTTGTCATCTACATGCTACATAATGGGTATCCA
GTAAGGGCTACTAAATCACAGACAACATTAGTGTTACCATTGTTAATTTCACCCAAACAT
[A,G]
GTATAGTGGAAAGAGTGCTGAAGTTTTCTACAGAGCACACCTGACCACTTCTAGTGCTTC
TAGTATTTTACACAAGCCCCCTACCTGGCACATAATAAGTAGTCAGTAGATATTTGTGAA
ATGAAATCAATGACTAAGAGTTAGAAAACCTGAGTTCTAGTTCCAATTGCACCCTCTTGG
ACTCTAAATAATTCTTATTGTCTGCTTTGCAAAGAAGAACATGTAAGTTATTATTCACCT
TAATAATGGTAATAATAATTGAGGACTAACTATGAGCTAGACACTTTACATATTTTACTT

58021 CTAGACACTTTACATATTTTACTTTACTTTGATTCACAACAGCCTTATCAGATAGAGACA
ATGTTGTAAACCCTACTTTACTGATGAGAGAGCTGAGGCTTTGAGAGAGGTATGTGACTT
GCTTAGGGTCACCTAACCAGGAAGGGGGTGACCTAGAATATCCACACCTGTTGGACTCCA
AGTGGGTCGTAGCCGTATTCCACTTTACCTTAATTATCAAAGGGCAGATATAATGATTTG
GTAATTAAAACAGTGCCCTAGACTGGGGACTGGCCATAAACTTTTGCAGGTTCATTTCCA
[A,G]
ATGATTATGTCTTTCCACCCAGACGTGATTTTAGAATCTGTGAGCCTGGCGACATATTTC
AGGAGTGTAATCTGAGTGGAGTTCCTACCCTGGGACTCCAGCAGCCTCCCTCGCTACAGC
TAATGAAGCCACTGGCGTTCACTGAATCTATGAACCTCGATTGGGCTCATTACTGTCTCA
CTTCTGGAGCGCTGCTGAAAGCTCCTGGGGAGTTACTATTAACATCTTTATTAACCCGTC
CCCCAAATCAGTCAGTGAAATTAATTTAGATACACAGCCACTTTGATCTTCATTAATGGT

58064 CTTATCAGATAGAGACAATGTTGTAAACCCTACTTTACTGATGAGAGAGCTGAGGCTTTG

FIGURE 3AA

AGAGAGGTATGTGACTTGCTTAGGGTCACCTAACCAGGAAGGGGGTGACCTAGAATATCC
ACACCTGTTGGACTCCAAGTGGGTCGTAGCCGTATTCCACTTTACCTTAATTATCAAAGG
GCAGATATAATGATTTGGTAATTAAAACAGTGCCCTAGACTGGGGACTGGCCATAAACTT
TTGCAGGTTCATTTCCAAATGATTATGTCTTTCCACCCAGACGTGATTTTAGAATCTGTG
[A,C]
GCCTGGCGACATATTTCAGGAGTGTAATCTGAGTGGAGTTCCTACCCTGGGACTCCAGCA
GCCTCCCTCGCTACAGCTAATGAAGCCACTGGCGTTCACTGAATCTATGAACCTCGATTG
GGCTCATTACTGTCTCACTTCTGGAGCGCTGCTGAAAGCTCCTGGGGAGTTACTATTAAC
ATCTTTATTAACCCGTCCCCCAAATCAGTCAGTGAAATTAATTTAGATACACAGCCACTT
TGATCTTCATTAATGGTTGCTTCTAGTTTCTACATTTATTTTTAGTTTTCTCATCTTTAA

59067

CTGTAATCCCACCACTTTGGGAGGCCGAGGCGGGTGGTTCACTTGAGATCAGGAGTTCGA
GATCAGCCTGGCCAACATGGTGAAACCCTGTCTCTACTAAAAATACAAAAATTAGCCAGG
TGTGGTGGCAGGCACCTGTAATCCCAGCTACTCAGGAGACTGAGGCAGGAGAATCACTTG
AACCCAGGAGGCAGAGGCTGCAGTGAGCCAAGATCATGCCGCTGCACTCTAGCCTGGGCA
ACAGAGTGAGATTCCATCTCAGAAAAACAACAACAACAACAAAAGAAACACACATAAACA
[T,C,G]
AGCAGGTATACAAGTGGGCTCACCTGAGTTACTTTAACGTTTTTAAAGTAAGGTTTAATA
TATTTATTTCATTTTTATTTTTCATCCAACCATCTACTTCTTATTTATTCAGCAAATATG
TATTGAATGCTAGGTACTAGGGACTGAGAGAGTAAAAAATAAATATGACACTGGTACCTG
CCTTCCAGGAATATAGTCTAGAGGGGAAAATAAATAAATAATACAATGTGGAAAGTATAC
TACAGCAGCATTGCCTGGGGATCTTTAAGAAACGAGGGAAATCTTGGACTTGGCTGTGAT

60034

AGCCACCGTGCCTGCCCTAGGGATGGTTTTTAAAGAAAGAGATGTGAGCTTGGCCTCCCA
AAGTGCCGGGATTACAGGCATGAGCCACTGTGCCCGGCCACCCCTGCTATTTTATTCAAA
GGAAACAGAAGGGGGAAGGAACAGATTTATAGAGAAGGTAATGAGTATAAGGTTTTAACA
TTTTGAGATTAAGGTATCTGTGGAACCACAAAATGGAGATATCTAAAAAGCAAGTAGAAA
TATAAACTGTGAGTACAAAAGTCCAGCCTAGAAATACAGAAGTCACATGCTTAAATCGGT
[A,G]
TTTAAAGCCTCAGGTGTGAATTTAGTTGCCCAAAGGAGAGAGTGTAGAGAAAGAAGAAAG
GACAATGAGGGAACCCTGTGGGGCCAGTACTGCAGGACTGGGTAGAGGGAAGGGAGTCTT
TAGAAGCTGAGAAGGAACAGCCAGAGGAGCTAAAGGAGACTAGTAGGTAATCCTAGCAAT
ACCATGGAAATCATATGGCCAGCACTCACTGGAAGAGGGCTGGGTTCCATGCCTGTGTAT
TCTCAATGCTGAGCTCATTGGCTGCATGTGGTGGCCCTTCAATATTTGTGGAGACTACAA

63709

TACTTTCACAACCCTATGCAGTAGAAACTATTACTATCCCTCTTCTGCAGGTGGGAAAAC
TGAGGCCCAGTGAGGTTAAGCAATATCTTCCGGTCACACAGCTGGTAAGAGGCATAGTGT
GGGTTCACCCGGGTCCTGGGTCCAAGTGCCTGGCCACGCATTGTTTATACTGCCCATAAC
TTTTCAAAGGAAGGGAAAGAGGAAGGAAAAGCAGATAGGATTTATTTTGTTTAATGGTCC
AGAGCAGGCATTTTGCACTCATTATTTCATTGGTTCGCTTCAGGTGAATACCACCTTCAA
[A,T]
TTGCATTGAGAAAACTGAGGGTTGCCCCTACAGAATGCGAGAAAATTTTTGCAATCTACT
CATCTGACAAAGGGCTAATATCCAGAATCTACAAAGAACTTAAATAAGTTTACAAAAAAA
AAAAACCATCAAAAAGTAGGCAAAGGATATGAACAGACACTTCTCAAAAGAAGACATTTA
TGCAGCCAACAGACACATGAAAAAATGTTCATCATCACTGGTCATCAGAGAAATGCAAAT
CAAAACCACAATGAGATACCATCTCCCACCAGTTAGAATGGCAATCATTAAAAAGTCAGG

63817

GAGGCATAGTGTGGGTTCACCCGGGTCCTGGGTCCAAGTGCCTGGCCACGCATTGTTTAT
ACTGCCCATAACTTTTCAAAGGAAGGGAAAGAGGAAGGAAAAGCAGATAGGATTTATTTT
GTTTAATGGTCCAGAGCAGGCATTTTGCACTCATTATTTCATTGGTTCGCTTCAGGTGAA
TACCACCTTCAAATTGCATTGAGAAAACTGAGGGTTGCCCCTACAGAATGCGAGAAAATT
TTTGCAATCTACTCATCTGACAAAGGGCTAATATCCAGAATCTACAAAGAACTTAAATAA
[G,A]
TTTACAAAAAAAAAAAACCATCAAAAAGTAGGCAAAGGATATGAACAGACACTTCTCAAA
AGAAGACATTTATGCAGCCAACAGACACATGAAAAAATGTTCATCATCACTGGTCATCAG
AGAAATGCAAATCAAAACCACAATGAGATACCATCTCCCACCAGTTAGAATGGCAATCAT
TAAAAAGTCAGGAAACAACAAATGCTGGAGAGGATGTGGAGAAATAGGAATGCTTATACA
CTGTTGGTGGGAGTGTAAACTAGTTCAACCATTGTGGAAGACAGTGTGGCGATTCCTCAA

64845

TAGGAGAAATAGCTAATGTAAATGATGAGTTAATGGGTGCAGCAAACCAACATGGCGCAT
GTATACCTGTGTAACAAACCTGCAGGTTGTGCACCTGTACCCTAGAACTTAAAGTACAAT

FIGURE 3BB

AATGAAAAAAATTAAATTAAAAAAATCAGAAAAAAAAAGAAAGAAAACTGAGGGTTGCCA
TGGATGGTCAAAGTATCTTACATGAGGTCTCAGCAAAACTGAAGCAGCAGAGTCTGTATT
GAAACCCTAAGTCAGCTAACCCCCAACCCACGTGCCACAAGAACCCCACTCAAGTTAGAA
[A,-]
GAGTATTAAAATATTGGAGGCCAAAAACACAGCACATAGACCTCTCAGAAGGGAAAAATA
GAAAATGGGAAAGGATGGAAATGGATTTCATTTTGTTGATTGAAATTGGGAGATGACTGA
ATGAGGAAATATTTTGATTTTGTTTGGCCAGGGAAGAGCTGTAAATAGGCAGCAGAAAGT
GGTTTGAAGAGAAACATACTAAACAAATGCCAGATATTCTTATCTTTACTGGTTATTTTG
AACTTAGGCAAAATCATACTGAACAGAGAGTAAATAACCTGTATAGACAATTGCTTCTCT

64848

GAGAAATAGCTAATGTAAATGATGAGTTAATGGGTGCAGCAAACCAACATGGCGCATGTA
TACCTGTGTAACAAACCTGCAGGTTGTGCACCTGTACCCTAGAACTTAAAGTACAATAAT
GAAAAAAATTAAATTAAAAAAATCAGAAAAAAAAAGAAAGAAAACTGAGGGTTGCCATGG
ATGGTCAAAGTATCTTACATGAGGTCTCAGCAAAACTGAAGCAGCAGAGTCTGTATTGAA
ACCCTAAGTCAGCTAACCCCCAACCCACGTGCCACAAGAACCCCACTCAAGTTAGAAAGA
[G,-]
TATTAAAATATTGGAGGCCAAAAACACAGCACATAGACCTCTCAGAAGGGAAAAATAGAA
AATGGGAAAGGATGGAAATGGATTTCATTTTGTTGATTGAAATTGGGAGATGACTGAATG
AGGAAATATTTTGATTTTGTTTGGCCAGGGAAGAGCTGTAAATAGGCAGCAGAAAGTGGT
TTGAAGAGAAACATACTAAACAAATGCCAGATATTCTTATCTTTACTGGTTATTTTGAAC
TTAGGCAAAATCATACTGAACAGAGAGTAAATAACCTGTATAGACAATTGCTTCTCTTAG

64914

TGTAACAAACCTGCAGGTTGTGCACCTGTACCCTAGAACTTAAAGTACAATAATGAAAAA
AATTAAATTAAAAAAATCAGAAAAAAAAAGAAAGAAAACTGAGGGTTGCCATGGATGGTC
AAAGTATCTTACATGAGGTCTCAGCAAAACTGAAGCAGCAGAGTCTGTATTGAAACCCTA
AGTCAGCTAACCCCCAACCCACGTGCCACAAGAACCCCACTCAAGTTAGAAAGAGTATTA
AAATATTGGAGGCCAAAAACACAGCACATAGACCTCTCAGAAGGGAAAAATAGAAAATGG
[G,T]
AAAGGATGGAAATGGATTTCATTTTGTTGATTGAAATTGGGAGATGACTGAATGAGGAAA
TATTTTGATTTTGTTTGGCCAGGGAAGAGCTGTAAATAGGCAGCAGAAAGTGGTTTGAAG
AGAAACATACTAAACAAATGCCAGATATTCTTATCTTTACTGGTTATTTTGAACTTAGGC
AAAATCATACTGAACAGAGAGTAAATAACCTGTATAGACAATTGCTTCTCTTAGTGCCCA
CCTGGGACTATAAAATGCCAGCAGAGAGGTCCACATTTGATTGCGCCTGACCTTGAAAAC

67367

AGGAGGATGTGAGTCAAATTGCATTAGGGCCCACCCTAATGCTTTCATCTTAACTAATTA
CATCTACAATGACCCTATTTCCATATAAGATCATATTCTAAAGTAATTGGGGTTAGGACT
TCAACATGTGAATTTTGGGAGCACATAATTCAACCCATAATAGTGACCTTTCACCAAATC
ATAAAAATTCATCAGGAGATGAGGCTTTAAAAATCACATTAGCCTACCTGATACTTGAAT
CATTTTTTTAAACCAAGCCAAGAAGAGCATTTAGAATTTTAACAGTATATTTGGCAACAG
[G,A]
GTTTTCGGGTGGATTTTATTTTTTAACGCCCTCTGTATGCTTCCCAGAATGGTTCCCACT
GCCTACGCCTCGAAGCCTTCATGTTGTCTGGAACAGGTGAGTACTACCTCAGGAAGGGAT
CTTTAAGGGTTCTTTAAGCAGGATTGGAGAGACATTTCCCTGGATCTCAGTCCACTGAAC
AGCAGCCCCCGAGCACTTCCATGTGGGGGCTCTAAGCTGTAGGAAGATGCCTCTGCAAGC
GCCAGACCCCTGAGAGTCTGTTAATTTTTTTCTATGAACCATTTTACTTTCAGTGAGTTT

67497

AATTTTGGGAGCACATAATTCAACCCATAATAGTGACCTTTCACCAAATCATAAAAATTC
ATCAGGAGATGAGGCTTTAAAAATCACATTAGCCTACCTGATACTTGAATCATTTTTTTA
AACCAAGCCAAGAAGAGCATTTAGAATTTTAACAGTATATTTGGCAACAGGGTTTTCGGG
TGGATTTTATTTTTTAACGCCCTCTGTATGCTTCCCAGAATGGTTCCCACTGCCTACGCC
TCGAAGCCTTCATGTTGTCTGGAACAGGTGAGTACTACCTCAGGAAGGGATCTTTAAGGG
[T,A]
TCTTTAAGCAGGATTGGAGAGACATTTCCCTGGATCTCAGTCCACTGAACAGCAGCCCCC
GAGCACTTCCATGTGGGGGCTCTAAGCTGTAGGAAGATGCCTCTGCAAGCGCCAGACCCC
TGAGAGTCTGTTAATTTTTTTCTATGAACCATTTTACTTTCAGTGAGTTTGGTCGTTAAA
ATTGTTTTGTGTCCCTCAGCCATGCCCCAGGCCCTGAGAACGAGGGAGTGTTGGTCTGCA
AGAAAACCTAGTGGGTTTATTATTCTCTGACACAGAGAAACCAAATAACATCATTGAGTG

68252

GGGAATAGTTAGCTAACTAAGCTGTGCCAGGCAACCTCCGGGCTAAGAAGAACTCAGTGT
TTTCGGACAATGACCAATTACAATAACCAGTATTATTTGATCTGAGAGTAATTAGCCGAG
GCTCTGTTCTTTTTGCTTCAGTGAGGAGGCAAAAAGGGCAATGAGGAAAACATCAGAGAC

FIGURE 3CC

AGGGGAAACGAGCTCAAATGTCAGAGAAAAACACAGTCTTGCAGGTGGGGAGAAGTGGAA
GAGTTTCACTGGCCAAGATCCTGACTGAACACTCGAACATTGTTTTTCCCTGAAAATATG
[G,-]
TAGAATTTAACTTAACCAAAAGTTGTTTGAATTCTTCACTCTTACTGTTCATTTCCTTTA
AAAAGCCTCCACGTAGAATAAAATATCAGGGTACAAAGAGTAAAATAGGTTAGGAACATA
GAACTATGGACTACCAGAGATCTTTCACTGGGAGGGACAGGTATCTCCAGGACATCTGCA
CCCTCCACTCTTATTTTCAACAGCACTGTATAACCTGAAACCTTTTGGAGACAGGTTCTA
GGGAACTACTGTTTATCACTTCATTCAAGACGTGCAGTATAGTCAGGCTCCTTCCCCTCT

68580

TGAATTCTTCACTCTTACTGTTCATTTCCTTTAAAAAGCCTCCACGTAGAATAAAATATC
AGGGTACAAAGAGTAAAATAGGTTAGGAACATAGAACTATGGACTACCAGAGATCTTTCA
CTGGGAGGGACAGGTATCTCCAGGACATCTGCACCCTCCACTCTTATTTTCAACAGCACT
GTATAACCTGAAACCTTTTGGAGACAGGTTCTAGGGAACTACTGTTTATCACTTCATTCA
AGACGTGCAGTATAGTCAGGCTCCTTCCCCTCTACCTAGAGATATGTGGATTTTAGCATG
[C,G]
CCCGTGGCTTTCTTTCATGTCACTATCAGCTTCCAAAGTAAATGGCAACTCTCAACCTGA
GAACCATCTTAATACTCCATGCTGCTGCTGCTGCAGCTGCCCCTGTCCCATGGCAGAAGA
TAGTTCACCAGCCTCCTGCTATCACCCCACCAGCCTTTCTTTCGAGGGCTGAGCAAGGCT
TGAATTCTCTGAATACCTCTCTGGCTTTTCTGACGATATAGCACCCATGGCCTCTGCGCC
TTCCCTTGTCCCCTAGCAATATGTATTCACCTTTTCTCAGACTTCTGGCTTCTCTGCTCA

69990

CTGTGGATTTGGCTGTTGAATCAGGTTGCAGATGTGGCGAGTAACAAGCAGCCGAAGTGT
CACTGGCTTTTCTACACAATCCCTTCAGAGGTGCAGTGGAACCATTCACAGGCCTGTAGA
TGAATCCCCGGGGCTTGCTTGAGGTTTGATGGTGATCTCCTTAATGTGGGCCTAGTAGGT
ACGCACTCACTTTTTAGATTGATTGGCAAATTGTAGGACAGCTTCTGCAATGTTTCTTCC
TAGTATTGGATGTATTTCTGACTGTGGGCATCTACTACATCCCAAACTGAGAACATTTAA
[G,A]
AAGTGCCTACTCTATCCCTGCCCTGTTCCTCTTCCTGTAGGTCTAGGGGGAAAACCAAAG
AACCCAGTTGAGCTCATACTGACCAGCCTGTCCTGCACCTCAGAGGTCAGTGGCAGTGCT
GTGGGTGGGAGACTTTTATACTCAGAGCCAGGCTGTGCTAGGAAATCAAAACTGCTGTCC
CAGACCCCTGAGAACAACCAGATTTTAGTAGTATGGAGTGATGGGTTAGTAGATGGTGTT
TTACGCAGTCACAAAACTCAATTTTCATTTTTTCTTATTGTTTGTGTTTCTATTCTGGAC

71472

TAGTTAACATCACAAACCTAAGAGTATGAATTCACATTTACCTTGGAAAGGTGCTGGTAG
GCAAATTAACATTTGTGATGTTCATTTTTTTATGCCAATGTTTATTTTTAAAGTAGGGGT
TGTAACCAGTGGATAATTGTTCCAGCGGGAGTTAGAGGTGGTGGCCACATGTACAACTAT
GACAGTAAAGGCAATTGGTAACAAGCAAGGCCATAGGTGACAGGAAAAAGCATAATGATA
CAAACACGGAAGATGTCAGTAAATCAACATTTGTGCCCAAAAAGTAACATTTGTTTTCCC
[A,G]
GGACTCTTTCCTCAGCCTTGCAAAAAGAGCTCAATGTGCGATAGCAAGGCGGCGATTACT
GGGGCACTTGCCAAAGGCCCAGATCCTAATGGTCTTGCTACCAGTGCTGCCAGTGAAGGT
TTGTGTTCATGTGGGGTGGAGTTGGCTTGTACAGGGGAGACCGACACACACTTGGCTCCT
AGGAGGAAGAGACTTCACTTGCCCACTTTGCCCTGGTGACCACCTCTACCGGCGAAGGAG
AAGGAGAAGCAAAGTGCAGCAGTCATAGTTCAGAGGCTGTGAGACTGGAACAAGTCCAGA

71664

AATTGGTAACAAGCAAGGCCATAGGTGACAGGAAAAAGCATAATGATACAAACACGGAAG
ATGTCAGTAAATCAACATTTGTGCCCAAAAAGTAACATTTGTTTTCCCAGGACTCTTTCC
TCAGCCTTGCAAAAAGAGCTCAATGTGCGATAGCAAGGCGGCGATTACTGGGGCACTTGC
CAAAGGCCCAGATCCTAATGGTCTTGCTACCAGTGCTGCCAGTGAAGGTTTGTGTTCATG
TGGGGTGGAGTTGGCTTGTACAGGGGAGACCGACACACACTTGGCTCCTAGGAGGAAGAG
[T,A]
CTTCACTTGCCCACTTTGCCCTGGTGACCACCTCTACCGGCGAAGGAGAAGGAGAAGCAA
AGTGCAGCAGTCATAGTTCAGAGGCTGTGAGACTGGAACAAGTCCAGAAACCACCAGAAG
CCCTGAAACAACCCTGTGGGGAGGGTGAGGGTAGGTTCTGTTGGTTGAAATGGAAAATCC
TAAAAAAGAGGTCCTTGCACTAATTAGTACCTACCCTTCTTTTATTCATTCACCTGGTTT
AAAAAAAACAAAAACAAAAACCTGTTCTTATTTTATTTTTTTGAGACAGGGTCTAGTTCT

71677

CAAGGCCATAGGTGACAGGAAAAAGCATAATGATACAAACACGGAAGATGTCAGTAAATC
AACATTTGTGCCCAAAAAGTAACATTTGTTTTCCCAGGACTCTTTCCTCAGCCTTGCAAA
AAGAGCTCAATGTGCGATAGCAAGGCGGCGATTACTGGGGCACTTGCCAAAGGCCCAGAT
CCTAATGGTCTTGCTACCAGTGCTGCCAGTGAAGGTTTGTGTTCATGTGGGGTGGAGTTG

FIGURE 3DD

GCTTGTACAGGGGAGACCGACACACACTTGGCTCCTAGGAGGAAGAGACTTCACTTGCCC
[A,G]
CTTTGCCCTGGTGACCACCTCTACCGGCGAAGGAGAAGGAGAAGCAAAGTGCAGCAGTCA
TAGTTCAGAGGCTGTGAGACTGGAACAAGTCCAGAAACCACCAGAAGCCCTGAAACAACC
CTGTGGGGAGGGTGAGGGTAGGTTCTGTTGGTTGAAATGGAAAATCCTAAAAAAGAGGTC
CTTGCACTAATTAGTACCTACCCTTCTTTTATTCATTCACCTGGTTTAAAAAAAACAAAA
ACAAAAACCTGTTCTTATTTTATTTTTTTGAGACAGGGTCTAGTTCTGTCACCCAGGCTA

72590
TCTTGGCTTCCCCAGACACTCTACACAAACACAGTCTAAATAAAAACAATATGCCTGCCA
TGCTAACACAAGTTTAAAACAGGTCTCCCAGCCTTCCCTGTCCAATCAGACTGCAGCCCC
TCAGCCCTCACTACAGGGCAGTTCAGGAGCCATCTGTTGTGGGTTAATGCTGGGGGAGTA
TTCGAGAGAACAAATCGCTGATTGGGGTGGGACTGTGGAGGTGGAAGTTGATAGATGCAT
TGCTCCCCACCACCTACCCGCCCTCCCCATGTCCAGAAGTTCATATTTAACCAGAAAGCA
[T,C]
GAAGCCTGCAGAAAGTGGATTCAGGGCCAAATTTTGGCACAAACTTCACCTCACTACCCA
ATAGTGTGGGTGGACCAGCTAAAATTTGTTCATGAGATTTCCCCTGAGTCTCCTTCCAGA
GAGATCCTAGGCTCTAGTGATTTGTACTAACATTCCTCTTCCAAACGTCCATTTCATGGG
CCCTAAAAAACCTCTGCCTGGACAGGATACCCTGGATGAGGAATATATCTGCCAGTCCTT
CTTCAGGCCACAGCAAATGAGTAGACTTCTACACAATTCCTTTTTCTCCTAACTGGCCTG

72757
TGCTGGGGGAGTATTCGAGAGAACAAATCGCTGATTGGGGTGGGACTGTGGAGGTGGAAG
TTGATAGATGCATTGCTCCCCACCACCTACCCGCCCTCCCCATGTCCAGAAGTTCATATT
TAACCAGAAAGCATGAAGCCTGCAGAAAGTGGATTCAGGGCCAAATTTTGGCACAAACTT
CACCTCACTACCCAATAGTGTGGGTGGACCAGCTAAAATTTGTTCATGAGATTTCCCCTG
AGTCTCCTTCCAGAGAGATCCTAGGCTCTAGTGATTTGTACTAACATTCCTCTTCCAAAC
[G,C]
TCCATTTCATGGGCCCTAAAAAACCTCTGCCTGGACAGGATACCCTGGATGAGGAATATA
TCTGCCAGTCCTTCTTCAGGCCACAGCAAATGAGTAGACTTCTACACAATTCCTTTTTCT
CCTAACTGGCCTGGAAATTTGCAAGGATTTGGAAATTTGCAAATTTCTTCTCTATCTTGC
CTATGAAGCAATTATTCCTGAGTTTGAAAGTAGTTATCTGTTTGCAGAAACAGTTTCATG
TCTTGGGAATCAAATAGCTCAAATTTTTTAATGCAAATCTTATGCAAAAATTAGGTAAAT

72863
CAGAAGTTCATATTTAACCAGAAAGCATGAAGCCTGCAGAAAGTGGATTCAGGGCCAAAT
TTTGGCACAAACTTCACCTCACTACCCAATAGTGTGGGTGGACCAGCTAAAATTTGTTCA
TGAGATTTCCCCTGAGTCTCCTTCCAGAGAGATCCTAGGCTCTAGTGATTTGTACTAACA
TTCCTCTTCCAAACGTCCATTTCATGGGCCCTAAAAAACCTCTGCCTGGACAGGATACCC
TGGATGAGGAATATATCTGCCAGTCCTTCTTCAGGCCACAGCAAATGAGTAGACTTCTAC
[A,C]
CAATTCCTTTTTCTCCTAACTGGCCTGGAAATTTGCAAGGATTTGGAAATTTGCAAATTT
CTTCTCTATCTTGCCTATGAAGCAATTATTCCTGAGTTTGAAAGTAGTTATCTGTTTGCA
GAAACAGTTTCATGTCTTGGGAATCAAATAGCTCAAATTTTTTAATGCAAATCTTATGCA
AAAATTAGGTAAATTAGAATTCTGGGCCAAGACTTCCAGCATCTCTGCATCATGGCACCT
GGAAGGGAAATAATATCTGATCTTTCTTGCTTTAAGTCAGTAGGTGTATTTGACATTAAG

74565
AAGATCAACTTGAGGATTTGTCCTTACTGTGATTTAAGTACTTAATTCTCTCTCTTCCTC
TGCTCCATCTCAAGGGAACCAAGAGAGCTTCCTAACTAATAAGACTGGGTGAGCTTCAGA
AATGCTGCAAACAAGTGTATTTTCTACCCAAGCTTCACCCTCCAGAATCACCTCTTTAGA
ATTCTGTGCTTTTCCCCCTCCAGATTTCTGTGCTTGCCACCCTTGGAGTCCAGAGCCTTG
AACATGTTTTTTGTTTGTTTGTTTGAGACAGAGTCTTGTTCTGTTGCCCAGGCTGGAGTG
[C,T]
TGTGGTGCAATATTAGCTCACTGCAGCCTCTACCTCCCAGGTGCAAGTGATTGTCATGCC
TCAGCCTCCTGAGTAGCTGGGATTACAGGTGCATGCCACCACGCCCAGCTAATTTTTATG
TTTTTAGTAGAGACAGGGTTTCGCCATGTTGGCCAGTCTGGTCCCAAACTCCTGGCCTCA
AGTGATCTGCCTACCTCAGCCTCTCAGAGTTCGATCGTATTTTGAATCAGGCCTTTCTAC
TTGGTTGGGGCTGCAGTGTTCCTCCAAAAAGAATCCTTGATTATATATTTCTGTTTATAA

74850
GCCCAGGCTGGAGTGCTGTGGTGCAATATTAGCTCACTGCAGCCTCTACCTCCCAGGTGC
AAGTGATTGTCATGCCTCAGCCTCCTGAGTAGCTGGGATTACAGGTGCATGCCACCACGC
CCAGCTAATTTTTATGTTTTTAGTAGAGACAGGGTTTCGCCATGTTGGCCAGTCTGGTCC
CAAACTCCTGGCCTCAAGTGATCTGCCTACCTCAGCCTCTCAGAGTTCGATCGTATTTTG
AATCAGGCCTTTCTACTTGGTTGGGGCTGCAGTGTTCCTCCAAAAAGAATCCTTGATTAT

FIGURE 3EE

[A,G]
TATTTCTGTTTATAATTATATTTCTGTGTCTTTTATGTGTACATGGTGCCCAGACACACG
GTGGAGGGCAAGGGAGCTGAGTGATAGAATGAGGAGATTTTTCCCCTTCAACTTAGTAAC
AGGACAGTCAGTAAGAGTTTAGTATGGGGTTACTTTTCCAGTTGCCATCAACTTTAGCA
ATTCCAGGAAAATTCTACTTAAAATCTAAGTCTAGCCATCTCCTTTTCTTTACTTTTTGT
TTTTATCCCTTTGTTTTTCAGAAGGGAGGCTGCTGGAGAAACTCTATTTTTCTCTCCCAC

75462 GGGCAGGGTTCCTGAAGCTGAAGACCTGGCCTCCCAGATGCTAAAAGGCTTTCCCAGAGA
CCGCGTCTCCGCCCAGGAAGCACTTGTTCATGATTATTTCAGCGCCCTGCCATCTCAGCT
GTACCAGCTTCCTGATGGTGAGCGAGGGAGTGTGTGCGTGTGCGTGAGTGCATGTGCGTG
AGTGCGTGTGTGTGTAAGTCTTGGTGTCTTAAGTAGTTTGCCTCAGCACCGGAGAATCAT
AGCATTTACCCCCAGGAGTGAAGTTAGAGATCAGTTTGCCTGGGAGAAGCAAGATAGGAC
[G,C]
TAATCTTGTCTGAGTTTTGCATGAGCTTCTCTCAAACTCTGAAGCACTGGTGGGGAGAGG
TTACAAGGACCTCTTTGTAATGGTCCAGACATTTCACAGGTACACATTTACACTCAGAAA
TTGGATGAGATGGACGTTGTCTCTGAGTTGTTTGCCTTAGCTACCATCTGCCAGGAAGCC
ACACCAGTGTTTCTAACAAGACTCTTCTCCCTTTCTGCGGAGAGTAAGATGATAGGTGAA
GCGGATATGTCCTGAGAGGGAGCTGGGCCTTTCTTGATTGGTAATAGCAAGCTGCAGAAG

76045 AATAGCAAGCTGCAGAAGGCAGTGCCGGGGTGGGGTGCTGGGGGAAGGGAGGTCTCCTCC
GAGGCTGCCCACCTCCTGTAAACACAAGTTACCTTGGAATCAGCCTTTGCTGCCTGGGCC
TGAAGTCATCTTCCAAACCTGAAATCTGCTGAGGGATCATGTGGTTGGAACTCCCGTCAT
GTTTCTTGGACTGTGGCCAGGAAGGGCTACAGGAGGATGTGGGCAGTGGTCATGGGGGAC
TATCCTTAGGTGAGGTTTCTTTGAAAAAAATCCACCATTCAACTAAAAATAGTTTTAGGA
[A,G]
CAAGGGACAAGTAGACAAGAAAAGCAAAGCTACCAGGAAGGAAAAACAGAAGAGAGAGAA
GCAGCCAGGGTTGGTTTTAGAAGTCCTAAGCCAGAGAAAAGAAAGCTTAGGAGGGAGGGC
CTAAGGGCTGGAACTGCGATGAGGACACTGGAAGGGGCGTGGGGGAGTGGCGATGGGGTG
CAGTGAGATAAGGATGGGGACAGGGTGAGGAGCTACTGCCCAAGAGGTGTGGAAACAGCC
TGGTCCGCCTTGCCAGAGTTTGCAGACGCAGCTCCTCTGTGTCTAGGACATCGTCCTGCA

79973 ACTTCAGGCCTTCTTTGAGTGTTATCTCCTTAATATATTGGAAGGTCCCTATGATATCAC
TTCCCAAAGGCCACTTTAGGCTGAATTCCTTTAACCTTTGTTTCCAAATACAAATTCTGT
TTCTCCCACTTTTTAGTCATTTTGTTTTATTGTTCTCTTCTGAATCTGTTCCAATTATTT
TGCTTATCTCTGAGAATATGGAGGCAGCATAGACTCAAATTTCTTGCATGGTGGGAGAAT
CATGTTCCATTCATTCATTGGAGGTTTACTGAGTGTCCATGAGGTGTGATATTAAAGGAT
[G,A]
CAAAAATGAATTAGTCATAGACCCTGTCCTCAAAGAGCTTACGGTCCTTTAGGAAATAAG
ACAAGTATATAAACAGCTGCAGATCAAGTATACAAATAAAGTGCTCTAAGTGTTTGAAGG
AGGTGAGATTAACTCCAGCTGTGGGGATCCAGGATGATTTTGTGAGTGGCCTTGAAAGA
TGATGGGTCTGGATGATTGGAGAGGAAGGGCATACGGGCAAAGGAATGTCGTGTTCCTCT
CAATACCATCTAAGATCATTCTGAAGTTGTCTTCTTTTTAATCATAGTGGCTCAGTCTTA

83181 ATGTATGTGTATTGTGCCCCTAGTCAGAGTTTTAAGTGCACTTCGTGTTAGTTAGCAACT
TCAATTTAAAGTGCTGTGTGATCCTCTGGGCTTTGAAGATATGAATTCTCTATACATACA
CATGAGCTAAAATTACCGCATAATCACGAGGATGTGTGCACTTTGAATAATTGAATGCAC
TAAACATCTCCAGCTGATGGATTGATGATGTGGGAGAGTAGTGCAAAACCCACGTGACAC
GGAAGATTACAAGACATTTTGAAATGATAGCTTAATTTTCAACCTTTTTTTTTTTTTTTT
[-,T]
GCTTGTGCTTTCTCTTTTAGCGATTATGGGCAAGTAAAAGAGATTTGATTATCTTGTTTC
CTGTGAAAGGTTATTTAGCCCCTCAATCCCATTAAGTCACTTTCTGCACTCCAGTGCACT
GAGCCTTCAGGTTATCAGCCCAGGAAGAGTAAATGGAGACACCAGGATCAGATTTCTAAA
GGAAGGAAAGTTAAAGCAAAGTTTGAAAGGGGTGACAGCCAACAGCCATGAGCTTAGGAA
CTCAATTAGACTAAAAAGACAACTATCTCATTATCTCGTTCCGAAATGATCTAAATACAT

84935 GAAGTTTTATTTTCCGTACTTTTCAGATAAGCCCCTTGCAATGTCAACTTTTGGAGGAAC
TGGCTTGTAGCTTTAGTGTAGTGAGCATTCAGGAGTAGCAAGCACTTAACAAACACAGGC
ACTTGGGAAAATGCGAACTGCCAGTATTCTGAGCTAACCAAATACCTGATTTGGACATCA
AAGGTAGTATATATATTTTCAAATAGTTTTTTTTTTCTCAATTTGCAAAAGTTGCACCTT
AGAGTCTATATAAATAGATTGCCAGCCAGGCCCCGAGGCTCATGCCTATGATCCCAGCAC
[C,T]

FIGURE 3FF

TTGGGAGGCTGAGGCAGGTGGATCACCTGAGGTCAGGAGTTCAAGACCAGCCTGGCCAAC
GTGGTGAAACCTTGTCTCCATTAAAAATACAAAAATTAGCCAGATGTGGTGATGCTTGCC
TGTAGTCCCAGCTACTGCGAGGCTGAGGCAGGAGAATCACTTGAACCCAGGAAGTGGAGG
CTGCAGTGAGCCGAGATCACCCCACTGCACTCCAGCCTGGGCCACAGAGTGAGACTCAGT
CTCAAAAAAAGAAAAAAAAAAAAAAAAAAAGATTGCCTAATGTATCTAACAAAATTGGAAA

87476 AGATATCGGCTTCCTGGCTCTTCTAAGATCATTGTCTTGTCTTCAAAGAGCAGGGAAGTT
TAAAATTATAGCTGATCCTCAGAGCATTTTATGAAATACCTAAGTTTGTATTTTGACAAT
ATACATTTAGAATTACAATTGGTGATATAATATGGTATTTCCCAAGCAAAATATTCTCTA
GAGCAGAGCTTTTACTGTATAATTATTTTAAACCTGCTAGTTATAAGGACAGAATGAACT
TTAGCTGCATTCTGTGAAGTGGAGGGCCTTACCCTTCATAAAATTATCAAAGATACTAAT
[C,G]
GAAATGGGCTCAGATGGTGGTGCTCCATTAACATTATTATTATTTCTATTGTTGTTATTT
TATTTTCTTAAGCAGCTGGAAGGTAGGGAGATAACCTTGCCTTTCTGATCTACAGTGACC
TTCCACAAAAAATTGCTACCTGTAGACATAAATTGGTCACAATAGAAAATCAATTAAATG
CAGCATGTCAAGCTTGTGGCCTGCGCCAGCAATTGAAGAAGGGAGAAGGCAGATTTTGCC
TCTGCTGGAGTAAGCTCATGATGTCCCTAGGCCTTGGTACGAATGTAAGGAGATAAAACT

FIGURE 3GG

SEQUENCE LISTING

<160> NUMBER OF SEQ ID NOS: 10

<210> SEQ ID NO 1
<211> LENGTH: 2203
<212> TYPE: DNA
<213> ORGANISM: Homo sapiens

<400> SEQUENCE: 1

```
gtgagtcata tgaaagctcc acgctgctga cctctggcaa aaagggagag aacaaggata     60
ggagaggcag tgggggaaag gttcaagtgc gggttttctc cttgaaccta gaagattatg    120
ggtcaagagc tgtgtgcaaa gactgtacag cctggatgca gctgctacca ttgttcagag    180
ggaggcgagg cacacagctg tcggaggagt cagcctgaga ccacggaggc tgcgttcaag    240
ctaacagacc taaaagaagc atcatgttcc atgacttcat ttcaccccag gggacttcaa    300
gctgcccgtg cccagaagtt caagagtaaa aggccacgga gtaacagtga ttgttttcag    360
gaagaggatc tgaggcaggg ttttcagtgg aggaagagcc tcccttttgg ggcagcctca    420
tcttacttga acttggagaa gctgggtgaa ggctcttatg cgacagttta caaggggatt    480
agcagaataa atggacaact agtggcttta aaagtcatca gcatgaatgc agaggaagga    540
gtcccattta cagctatccg agaagcttct ctcctgaagg gtttgaaaca tgccaatatt    600
gtgctcctgc atgacataat ccacaccaaa gagacactga cattcgtttt tgaatacatg    660
cacacagacc tggcccagta tatgtctcag catccaggag ggcttcatcc tcataatgtc    720
agacttttca tgtttcaact tttgcggggc ctggcgtaca tccaccacca acacgttctt    780
cacagggacc tgaaacctca gaacttactc atcagtcacc tgggagagct caaactggct    840
gattttggtc ttgcccgggc caagtccatt cccagccaga catactcttc agaagtcgtg    900
accctctggt accggccccc tgatgctttg ctgggagcca ctgaatattc ctctgagctg    960
gacatatggg gtgcaggctg catctttatt gaaatgttcc agggtcaacc tttgtttcct   1020
ggggtttcca acatccttga acagctggag aaaatctggg aggtgctggg agtccctaca   1080
gaggatactt ggccgggagt ctccaagcta cctaactaca atccaggtaa tattgatctg   1140
agcttttgaa tactctgaga attagtaatg taaggagagc attggccacg ctaacagggc   1200
gttcttgtat tgtgaactca gcggcaaaga tgggtgtaga ggaatttcta cattcatata   1260
ttccctgact aatctttgta tgaggaagac actgaaagag tagctgaggt tagaccagtt   1320
ccccagctct gtaaaacaca agtagcaagc tgaatagaat ttgaaatgac tattactgtg   1380
gattccacat ccattgtcaa atacccaatg gctcaaaaga acaactcaaa agatgggctc   1440
acttttgggc cccctgactg tcataagtgt attgattagt attgaattgc atatgtataa   1500
aaagaaagct aatgcaacag aacagaggta gaggctcgct aggcctagga catgccaagt   1560
aagctgtctg taggttatac ttactaagag ttcattcatt gcctgtaaac ctgacacttg   1620
gtcattgtct ctcacacatt tcatctttca agactggctt ctgggatcga tttagaagtg   1680
ctggaagtgt tatccatggg ggaattcttt gagaagctgt cgcagggcca catcagaggg   1740
atcagattaa gcagtagtca cttcaaggat gttgagacag aggggaggag acaggcactg   1800
aactacagga tgaaggatca tattagaagc tgaagaagca aataaagccc atgccaaagc   1860
tgagctctca ctggcagggt tgaaggggag gtagaaaggt acagataacg acaagattag   1920
ggtggatatg ctccaagcca gatttttcta gtctttatgg tcttacattg ttccattact   1980
aaaaatgaaa tcttcccaaa ttgttgtcct tacttttttt tttttttttt gagatggagt   2040
```

-continued

```
tttgctctta tcgcccaggc tggagtgcag tgagccgaga ttgcgccact gcatgtccgc   2100

agtccgacct gggcgacaga gcgagactcc gtctcaaaac taaaaaaaaa aaaaaaaaaa   2160

aaaaaaaaaa aaaaaaaaaa aaaaaaaaaa aaaaaaaaaa aaa                     2203


<210> SEQ ID NO 2
<211> LENGTH: 343
<212> TYPE: PRT
<213> ORGANISM: Homo sapiens

<400> SEQUENCE: 2

Met Gly Gln Glu Leu Cys Ala Lys Thr Val Gln Pro Gly Cys Ser Cys
 1               5                  10                  15

Tyr His Cys Ser Glu Gly Gly Glu Ala His Ser Cys Arg Arg Ser Gln
            20                  25                  30

Pro Glu Thr Thr Glu Ala Ala Phe Lys Leu Thr Asp Leu Lys Glu Ala
        35                  40                  45

Ser Cys Ser Met Thr Ser Phe His Pro Arg Gly Leu Gln Ala Ala Arg
    50                  55                  60

Ala Gln Lys Phe Lys Ser Lys Arg Pro Arg Ser Asn Ser Asp Cys Phe
65                  70                  75                  80

Gln Glu Glu Asp Leu Arg Gln Gly Phe Gln Trp Arg Lys Ser Leu Pro
                85                  90                  95

Phe Gly Ala Ala Ser Ser Tyr Leu Asn Leu Glu Lys Leu Gly Glu Gly
            100                 105                 110

Ser Tyr Ala Thr Val Tyr Lys Gly Ile Ser Arg Ile Asn Gly Gln Leu
        115                 120                 125

Val Ala Leu Lys Val Ile Ser Met Asn Ala Glu Glu Gly Val Pro Phe
    130                 135                 140

Thr Ala Ile Arg Glu Ala Ser Leu Leu Lys Gly Leu Lys His Ala Asn
145                 150                 155                 160

Ile Val Leu Leu His Asp Ile Ile His Thr Lys Glu Thr Leu Thr Phe
                165                 170                 175

Val Phe Glu Tyr Met His Thr Asp Leu Ala Gln Tyr Met Ser Gln His
            180                 185                 190

Pro Gly Gly Leu His Pro His Asn Val Arg Leu Phe Met Phe Gln Leu
        195                 200                 205

Leu Arg Gly Leu Ala Tyr Ile His His Gln His Val Leu His Arg Asp
    210                 215                 220

Leu Lys Pro Gln Asn Leu Leu Ile Ser His Leu Gly Glu Leu Lys Leu
225                 230                 235                 240

Ala Asp Phe Gly Leu Ala Arg Ala Lys Ser Ile Pro Ser Gln Thr Tyr
                245                 250                 255

Ser Ser Glu Val Val Thr Leu Trp Tyr Arg Pro Pro Asp Ala Leu Leu
            260                 265                 270

Gly Ala Thr Glu Tyr Ser Ser Glu Leu Asp Ile Trp Gly Ala Gly Cys
        275                 280                 285

Ile Phe Ile Glu Met Phe Gln Gly Gln Pro Leu Phe Pro Gly Val Ser
    290                 295                 300

Asn Ile Leu Glu Gln Leu Glu Lys Ile Trp Glu Val Leu Gly Val Pro
305                 310                 315                 320

Thr Glu Asp Thr Trp Pro Gly Val Ser Lys Leu Pro Asn Tyr Asn Pro
                325                 330                 335

Gly Asn Ile Asp Leu Ser Phe
```

340

<210> SEQ ID NO 3
<211> LENGTH: 53332
<212> TYPE: DNA
<213> ORGANISM: Homo sapiens

<400> SEQUENCE: 3
tataggccaa tgctgtggct cacgcgtgta ttcccagcac tttgggaggc aggaggatcg 60 ttgagctca ggaattggag acaagcctac gtaacatagt gaaacctctg tctgtacaaa 120 aataaaaga attttccagg catggtggcg tgcaccccca gtgccagcta tttgggaggc 180 gaggtagga ggaatgcttg aagccaggag ttgaagacaa gcctaggcaa catagtgaga 240 cctgtgtct ataaaaaata attagctggt tgtcttggca caggcctgca gctagctact 300 ggaagactg aggtgggagg atcactgagc ccaggaggct gaggctgcag tgaacagtga 360 cacccagct ggattccagc ctggaagaca gagggagacc ctgtttccaa aaaaaaaaaa 420 aaaaaaaat gcaagaaaag acatcataaa cttgacctgg gacataactt ttatgtgatg 480 aattcacaa tcttttagga agaaattagc atttctgata aaatgtatta taattatatt 540 ttataaatt caaatggaat taaatattct gagaaactag cttctcactc tctcagttgt 600 agtcaaaac tttaatggtc tttggccggg tgcggtggct cacgcctgta atcccagcac 660 ttgggaggc cgaggcgggt ggatcacaag gttaggagat cgagaccatc ctggctaaca 720 ggtgaaacc tcgtctctac taaaaataca aaaaattagc cgggtgcggt gccagacgcc 780 gtagtccca gctgctcagg aggctgaggc aggagaatgg tgtgaacccg ggaggcggag 840 ttgcagtga gccgagattg cgccactgca ctccagcctg ggcgacagtg cgagactctg 900 ctcaaaaaa aaaaaaaaaa aaaagttgaa tggtctttga gccaagtagt cttccttttc 960
ttcttcttct tttttttttt ttttcaaaaa atatctctag attgaatctt ggaattggct 1020
taagtctctt ctcttgtggc aattttgaaa tgaaaaaata catgctcata attaaattac 1080
ctgaacattt taaaaaacca tcatgaggtt caaatatcaa atattcataa atattgttgt 1140
gataatagac ataactctta ttttttccct taataatgat tgtttatata tcctccattc 1200
tgtctcactt tatgattagt atattatagt ggcaataatc ttaggaatct aacagagaaa 1260
agtgttgcat ttgaagacta cagactgcaa accaatttaa gccagattcc ttgacatgtt 1320
gtgctgttaa tatagtactt tacatatagt aaacattaat tacatatatg tggaaggaag 1380
caagcaagaa aggaagaaag tatttcattc aaactcctct ctctccatca ccattggcta 1440
atatcatcat ttgtacagtt aagaacaaca taggtgctca ccacatagtt tttgaataaa 1500
tgaatgaatg gcaacccttc taagactatt ggatacacta ttgtttgaag gcaaagagat 1560
gcagtagata ttttcaactt ttttcctgtt ttatgattct gtggtttctt tgactactaa 1620
aagttagcta ggtagcaaat ttgttttaaa gtctgaaaac caaaatgctt tcagataaaa 1680
ggtagggaga aaaatactcc tcaacatgtc cactttagca ccaggaaaac ctaatatcaa 1740
tatcaccatc aatgatatca tataaatatc attgcataga taagcaatgt caatccctaa 1800
aaactatgta taccaatagc actaacttgt ggccagaaca agaaccttaa ctgtgccaaa 1860
ttttattcta ttcaataaca gctgcctcgt tttcagttgt gcacatctga atgcaagcaa 1920
tccctgtctg atgtggagtt tcttgcactg ataaggaaaa actgctgaag ttgtgaggct 1980
gctccaggca gagccatcat gtgagtcata tgaaagctcc acgctgctga cctctggcaa 2040
aaagggagag aacaaggata ggagaggcag tgggggaaag gttcaagtgc gggttttctc 2100

-continued

```
cttgaaccta caagattatg ggtcaagagc tgtgtgcaaa gactgtacag cctggatgca   2160
gctgctacca ttgttcagag ggaggcgagg cacacagctg tcggaggagt cagcctgaga   2220
ccacggaggc tgcgttcaag gtatttgtat cccaggagag agcatctttc tctattgata   2280
aaccaaggag ttcagacact cccttttttgt agcgggatct gattcttctg cggtaggtct   2340
aaaccaataa aatgaaaatt ctattaaagt cacagaaaat ttatggctgt agttatcaaa   2400
tttggggaat ttcttgtaaa ccaaaaggga aaaataatcc ttggctttgg gctgcacgaa   2460
actcacttgg cttgaagtcg agaaagtagt tctctcaaaa tctctaaggt cctaaattac   2520
agagctgaaa cttaaaaggc aagctgcagt attagttggt atgctatgga tttgaaactt   2580
tagtaattag ttcatgatta ttagcaatgc catagattat tcccctacag caataaatta   2640
agtggacatg aaaaaaaaaa gccagactta aacagaaaaa agttgcaaaa catccatcaa   2700
agagatttag gttaacctga atgttaaaga cacattttta ggtgaagaaa gaatgtagta   2760
tttcaggagt tgataccatt atggtctttt tcagggatct ttcaagaaaa gtgccttttg   2820
ggggtacagg aagcttagaa aacatttgaa gagtgaaaat gaggcaaata aagaaaaaat   2880
ggttttacca ggcactgaat ctttactttg cataaatttt atttctgctc tttctttttt   2940
ctctagctaa cagacctaaa agaagcatca tgttccatga cttcatttca ccccagggga   3000
cttcaagctg cccgtgccca gaagttcaag agtaaaaggc cacggagtaa cagtgattgt   3060
tttcaggaag aggatctgag gcagggtttt cagtgggtga gtgagcagct gatgttgatc   3120
aagaagaatt taatgtgagc ttgtctacgg aggccggccc ttgcttccag ggcaattact   3180
gagcgagcct tcccaagtct gctctggcaa tgctgtctaa tttccctggg gaaaaaaagt   3240
caacactaaa aaaaagtgtt ctttctctct tccctttcac ccgctccttt tccccattcc   3300
cctagagcag aggaagagcc tcccttttgg ggcagcctca tcttacttga acttggagaa   3360
gctgggtgaa ggctcttatg cgacagttta caaggggatt agcaggtgag tgacacatag   3420
ctgggagaga ctttagagat gagagtcccg cccccccaat ttcatattat aaagccaggt   3480
gagacatcat agaagttcat agcactcagg acctgtgcaa gacaccatgg ccgacaggga   3540
gagagacatg ataacttaaa cagccttgaa agaaaaacaa acctgccctg ccctaattaa   3600
aatcagccca cttaaatgtt tatcagcctt tcccttcttg cattcaattc agagaattca   3660
aagaaaatag acattctcta ctactgaccc aaagaacaat tatcactctt caggcctgtg   3720
ggaggcacag ttggtaaagc gtctctaaca ggttttttat atccctccct aaatcacaat   3780
gacagagttt tgtaatggca acctggaatt tgctgcttca ttcctccacc tggcctttat   3840
agaagaaact gaagttggtt tctgcaaatt atggtacatg caaaagatga taaatcctag   3900
attttttata tttgcaaaat acacaaaatg tctggagaat aaaaatactg cttatccaaa   3960
agctaagtac taattttggt aaacaaccaa ctttgttaaa tatatgtaaa agatccatga   4020
attcccccttt tagtcaaggt gggaaagttg gatggtcgct tttttcttta tgttactcca   4080
atagagagaa aagtaatggc tcaatagtgg ttaaatatta attttaaaaa tatagctgat   4140
ccgagtgcag tggtgtttac aactacttga tcacaaccag ttacagattt ctttgttcct   4200
tctccactcc cactgcttca cttaactggc caaaaacgaa aaaagaaaaa ttttatataa   4260
ctactacaag actaaatatt tattatttat cttagtattt atgctgttat tattattttt   4320
acttgttaaa acaggattgt aggggacata cagttttatt ttattttatt atttatatat   4380
ttatttattt attttggaat ggaatctctg tcacccacgc tggagtgcag tggtgcgatc   4440
```

-continued

```
tcagatgact gcaacctctg cctcctgagt tcaagcaact ctcctgcccc tggccccttta   4500
tactttctta atctgtttta gtcatggtgt accttaactt ttttcaatgc tgagaacatc   4560
tgcaataaag gaccacattt tattttattc taagcttcct catatcaatt tggccatggt   4620
aactgttttc aaggtggctc ggaacggggg caccctggaa catacttgga tacatgggca   4680
ccatggacac ttctgatcct ctcttctgag ttctgacttt gattgttctg cacagacctt   4740
tccagcccga agtttacaca gaattcactt atcttttctt ctagttactt tatgttttct   4800
ttttcattta actctttcat ctactgggaa tttatattgt atattcacaa tcaccccagc   4860
tccatttatt agattttctt ttctctgatg gtttgaaatg ctgccatgat tatatattag   4920
atctcacgaa tacttgaaat tctttctgtt ctaatctttt aaaaatcatg tttccttaat   4980
ctatcttttc ttatatttgt gctgcatgat tttaattatt gttgctttag gctattttta   5040
gaatatatca aaactctacg ttagagaatt attgacatct ttgcattatt agattttcta   5100
atacaaatat cctgtaaata tctaatacaa cagtctctgg atggtcactg tacaagaccc   5160
tatagaatcc ctaccctcca ttccccggca cacactcagc tcctccctgt cctcatctcc   5220
ttcccctctc ctgcttcaat gacagactgc tcctgcctca gtcaaggact tttaacttgc   5280
tgttccctct gcctggagct gccttccact gttcatgcac acagctgact ccccctcgcc   5340
atcagattcc tggttcaagt gttaccttat ttataaaact gtagtcccag ctagtccagg   5400
gaggctggag gcaggagaat cacttgaact ttggaggcag aggttgcagt gagctgagat   5460
cggcaccacc gcactccagc ctgggtgaga gtgacactgt ctcaaaaaaa aaaaaaagca   5520
ttttctctta taaacatatt tgccaaaaaa ctttttgcag ggtttggggg agaatttcac   5580
agaaccatgt tctgaggaaa atacttacct cataaaactc taaaacaaaa tttcaaagac   5640
atgataaggc aaacaaaaga aactggggaa aagtatatgc aaaatagttc aataaaaagg   5700
tgggcaaatc ggcaaatcac aagaaaaaca gaaaagatcc ataaacttat gaaaagtcag   5760
tttcacatat ggttaaagaa atataaatta aaatgcgata aacctttttta cttttcaaat   5820
aggccaaaaa aaaaaagaag atgaaagcga aaagccaacc cacatgatag ggctatgaca   5880
gagggacaca ggagccaact gaaagagctt ccaaaggaca aagctgcaaa aatatgagca   5940
accaaaaaaa gtggtattaa attataaccc aaagtataaa ataaatatct atgagtccgt   6000
actgatataa ataaatgatt caatacatta acaaatggga gagaagaaac aaatctctca   6060
tgccaaataa atacaaataa tttatgtaga taatatacct tcaaagaggt acagcataac   6120
tctccactcc ttaagtgtgg gtcattcata gtggcatttc tctaaaagta cagtatgaaa   6180
aaggggggaga aagagtaact ttagagtaga gaaacctgac caacactatc tcagacaggt   6240
gactaaggtc aacatcaaaa gtcataaatc atgatgatgg tatgcactct tttttttttt   6300
tttttttttt ttctcagatg gagtctcact ctgtcgccca ggctggggtg cagtggcgca   6360
atctcagctc actgcaacct ccggctcccg ggttcaagcg attctcctct cagcctcctg   6420
agtagctggg atcacaggcg cgtgccacca tacccggcta attttttgta ttttagtaga   6480
gacggggttt caccatgttg cccaggctgg tctcaaactc ccgagctcag gcaatccacc   6540
cacctcaacc tcccaaagtg ctaggattac aggcatgagc cactgcgcct ggctgagggt   6600
atgcactttt tttttttttg agacggagtc ttgctctgtc gcccaggctg gagtgcagtg   6660
gcacgatctt ggctcactgc aagctccgcc tcccaggttc acgccattct cctgcctcag   6720
cctccccagt agctgggact acaaggtgcc ccaccaccca cacccggcta atttttttgta   6780
tttttagtag agacggggtt tcactgtgtt aggcaggatg gtctcgatct cctgacctcc   6840
```

-continued

```
tgatccaccg gccttcgcct cccaaagtgc tgggattaca ggcgtgagcc actgtgcccg   6900
gcctgatgaa atgttaaatc tttattaaat atcggattgt acaagaatga actataagag   6960
aaaagttaca tggaggaaaa aaggttacta acaatatgat tttaatccca ctgtattaaa   7020
aacaatggat ttatacctgc attaaaatct tctctattct cagcacttag ctgatatgaa   7080
taaaatgatg aatgagggga cagtaggagg aaatgaagag agagagaata atggtgtggc   7140
ctgggaagat caggtagcac ttagaagccc gctgcaagaa tttggctttt attctaagta   7200
atgcgtggag atatggtggc ttttgaacag aaaagtgact tgtcctgatt gtcatttgaa   7260
aagtatgcct ccaactacta ctgctgagag taaatagtag gagtgcaagt gtgctcagca   7320
gggaaactgt tagaagacca ctacaaggct gggcttggtg gctcgtgcct gtaatcccag   7380
cactttggga gcctgacgtg ggcagatcac ctgaggtcag gagttcgaga ccagcctggc   7440
caaaatggtg aaacccccat ctctgctaaa aatacaaaaa ttagccaggt gtggtggggg   7500
tcccctgtaa tcccagcttc ttgggaggct gaggcaggag aattgcttga acccaggagg   7560
tggaggttgc agtgagccaa gatcgtgcca ctgtactcca gcctgggcaa cagagcgaga   7620
ttctgtctca aaaaaaaaaa aaaaaaacaa aaaaacaaaa aaacactaca ataagtcaga   7680
tgaaaaataa taataagctc caaattttct ataatggaca tatatatata tatcacttta   7740
gtaaagaggg aaaatgcttt ggaatatata tgttatatat gtattgatac atgttaaact   7800
ttttattttg agaaaattat agatttatat gctagaatat attttgaagt gaaagtgctt   7860
ttgttaagcc atctttggta taaattgctg ctttgaacca cctcaataag tgtgtgcccc   7920
tcaatccctc tcttctagaa taaatggaca actagtggct ttaaaagtca tcagcatgaa   7980
tgcagaggaa ggagtcccat ttacagctat ccgagaaggt aagaacagca gaaatggacc   8040
caatagatct gttttgagtc cttgatttgg taaaaaatgt attgcattga tccattcagc   8100
atctagtttt gattcttctg gaatactata attacatttt tatttttcat acaagttttt   8160
caagaaattt acactgctat tttattactt aattttgagg aaattgagat ttaaaactat   8220
tatatcactt gaccaaaact ataaattcac tgagcaatta ctaatacttt ccatgtgttt   8280
ggcctcatgc taggtgctaa ggctatacct atataacctc agaaaattcc tataaaagag   8340
aaaatatata atcacacaaa ttcttactgg gaaatttgcc tgaacataac atgttgttag   8400
ctagcacttg gagattctcc agaaggcatg catgtttagt gttactgcct gtattttctc   8460
tgtgccctgg acagtacagc aaatgggtga ggaacctggt gtcaaatgga cttgggtttg   8520
cagcacaggt ccaccaatca ctagtggtat gatgttgggt aggttacttt agctatttat   8580
tactcagttt cttgcaggaa gaggataata gtggtaccta tttcatggag ttgttatgag   8640
tattcaacaa gaatatgtat ataaagcact tatcacagag tcagtttttc agagttcaac   8700
aaatgttgac catttttatt ccattcttct tttcctgggt aatgtcttat ttaccatcaa   8760
gataactaat actttataac ataaacatca agaagccaac atagtgaaat gaatcattaa   8820
aaatataatt tatcaacctt tattgcatga gccatttgaa ataagatgat gataggattg   8880
ctatgcattt cagcaaaatc ccagagaaat ggcacttccc tggccttatt ttctcccact   8940
tttaactact tatcttctgt tctttactga gcacatgcta tatgcagagt atgctgctgg   9000
atgctgtgaa ggatgagaag agaaacccat gtctttgttc tatcatttgc agtcttaaca   9060
gagcacatga ttcaagttac aagtgtataa aagacataaa ctaagatgag agcaagttag   9120
tctcagtgtg actgatggag tcactagatt ttgaactgag cttggaagga taggttatgc   9180
```

-continued

```
aaacaagcat ggaaaaagca attcagaaaa tgagtttata actgaatttg ataccctttt   9240
caaaagtctt tcagagcccc tgaggaatac atcattttga atttaattgg aagggccaaa   9300
tgggctattg gtttagccag agattcatcc tggtaggatc aggtgcattc tgggagaagg   9360
catggtttta agtgtttaat ataatggaaa ctgcattaac taatgtactt attaatggtc   9420
tccatgaaag gatgatcaga tttggaaaga gatgtatgga taggttaaag agtatttgtg   9480
aacgtaatag aaattcccag gtcacccgca taagaggaag gtttcctttg tgagcttgag   9540
tttgccaatt gcttaagatt ggctttgctt agatattgcc cacagccaag tttttcaggt   9600
tgacatttaa ctgtaacagt gaaacctttt gccaggtttg ctaacagatg gttctcagca   9660
tggttcagaa aacctggatc cgttttcttc tgtatgctaa atgtttcttt cattgcatat   9720
ttacggagga attgcctctc catcacaggt gtttacaatt acatttagta gtcaactgtg   9780
gactttcttg gtttgtttta tggacttacc ttaccgaatg ctttgctcgt gtaatattaa   9840
aaaccacaag aggatttctg acacattgga ggttgttagg aatccaattt ccaacaatga   9900
atgtttcttt ttacaccact ataaaagctt ggagcccttg ttaaaagagc cctctcccct   9960
caagaagata tgaggcttta ttcgaaaact ttggcactgt cccatttttc ctgtaagaac  10020
tttaaggatg tgagaccagg gagacaggag gttaaatgag aagggctgga aggcaaagta  10080
agaacagctg gagttcatta gctaaaatcc agggtcacta gctaaaaagg caaccgaaag  10140
gcacgtgcag gaaaactgaa caagtaatgc agccctcttt aaaaagcctt gaagcaggaa  10200
ttgcttttcc tgaacaattt ggctgccctg atggtatagc agccaaagat ttattaagta  10260
tgattttact acatatatgg tctctttcta tacaggtaga atacatgtgg caatttacta  10320
gtctggtcat ttggagtact attttcattt gaccttaaca tgtgatatta tgaaactagc  10380
aaaagtatga acagcactaa ggaacatttt tttttttttt ttttgagacg aagttttgct  10440
cttgttgccc aggctggagt gcaatggcac aatcttggct tactgcaacc tctgccttcg  10500
gggttcaagc aattctcctg cctcagcctc cggagtagct gggattacag gcatgtgcca  10560
ccacacccag ctaattttgt atttttagta gagacagggt ttccccatgt tggccaggct  10620
ggtcttgaac tcctgacctc aagtgatctg cgtgtctcag cctcccaagg gaaatatatc  10680
ttaatacatg tgtcagtgct tttcatactt ctttcaatcc tcttaacaat ctttagagat  10740
agatattatt aatattattc cactatatgg tggtgattca aaccaaatct ctctgattca  10800
aaaattcata ggctttctac gcacccactg tagaaatatt catttagcac ctactatgac  10860
caggtactct gccgaactgc tagatacaca gcaatacaca aaatagatgt gttccctacc  10920
accctcattc ctttgctaat taagaaaagc agaggccttc atagtgcctt ggaaatctct  10980
cataattgac tctagaattg tattttaagt gttgattttt acaactagga ggaaatactt  11040
tcatttgaat aggctaatgt gttatgtttt tacatagtac aacatttctt agttttatga  11100
aactttatag caatatctta atataatgtg cattgtttta aatatttttg ttcaagtggt  11160
caacttttgg tttaaactga ggactttcag cctgttaata gcatttttct taggaaggag  11220
tcatataact aatctttttt gaggacaagg catatgacat aatctccccc ttcccctaca  11280
taatgtatat ttttaaaacc tttataccaa ccctaggaag taaaatgtgc tatttttgtt  11340
gtagagataa agaaattcta gcctcagaga ggttagttaa cttgtctgag gtcacagaga  11400
tagtaatcag agttgttaga atccatttct attctattta aaatcccttc tactttatta  11460
tgatgaattt ggaaatgctt aactaaagta tttattgttt agcaacagta aaaataaaaa  11520
tagaaatctg tttttattat acattttata taaacgttaa ggaaaatgca gaagaagtat  11580
```

-continued

```
tttttaatc tttaatttta gattcaaggg gtacatgtcc aggtttgtta catgagtata  11640
ttgcatgatg ctgaggtatc ttgtcaccca aatagtgagt atagtacctg ataggtagtt  11700
tttcaacccg tgtccctctc ccttcctctc cccttttgga gtccctggtg tagtgtctat  11760
tattcccatc ttatgtctgt gtgttcccaa tacccccagt tattagcttt cacttgtaag  11820
tgagaacatg tggtatttgt tttctgttcc tgggttaatt cacttaggat aatggcctcc  11880
atctgcatcc atgttgctgc taaggaaatg gttttttttt tttttttttt ttgtggctgc  11940
atagtgtttt atggtgccag tgtacaaatt ttctttatcc aatccaccat tgctgggcac  12000
ctaggttgag tccatgtctt tgctattgtg aatagtgctg tgacgaacat aaaagtctag  12060
gtgtcttttt gacagaacga tttattttcc tttgggtata tacccaggaa tggaattgct  12120
gggtcaaatg gtaattctgt ttttggtttt tttgaggcag gagatgggac tcgactccag  12180
agatggggct tgaacactaa accaaattta ggactagcca aaacagggcc tgggggggagg  12240
cagctttcca gaagacacac ccaccagtgt gccatgtcag tttaccattg ccatggcaac  12300
acctgaaagt taccaccctt tcccgtagca acaacctgac aacctggaat taccactctt  12360
ttcctaaaac tttctgcata aactgcccct taatttgcat ataactaaaa gtgggtataa  12420
atataactgt agagctacct atgagctgct actctgggca cactgcctat gtggcagccc  12480
tgctctgcaa ggagaggtac acccgctgct gctgaacact gctgcttcaa taaaagctgc  12540
tgtctaacac cacaggctca cccttgaatt ctttcctggg tgaagccaag aaccctccca  12600
ggctaagccc cagttttggg acttgcctgc cctgcctcac tttgagaaat ttctaaactg  12660
ttttccacag tggctgaact aattaacatt cccacccaca gtgtataagc actccctttt  12720
cttctcaagc ttaccagcat ccattaactt tttacttcta aataatagcc tttttgactg  12780
gtgtgagatg gtatctcatt gaggttttga tttgcatttc tctgatgatt cgtgatgttg  12840
agcaattttt tcatatgttt gttggccact tgtgtgtcca aaagaaatat tttaaagaaa  12900
ataatacatc atgttgtata ttcatcaatt ctgattctat cattgattct acagtgccgg  12960
taattgcagt gtttaaatta gaaacagtct cagctaagaa tcttttaaga tcattctcta  13020
gtagaaaaac attacaaagt aatgattccc aatccatata tgagaaaact gagccaaaaa  13080
taggctaagg agcctcccta aggtcataca atgaggcagg ggaggaggct gattagaact  13140
tctgaattgc caatgaccac aaatagtcta gggtaggcct ggttgacaga aagtctgcca  13200
ttgaacacca tcatatcaca tgacaaatac agcaaattca ttgtgcatag ttacgtcttt  13260
ataaaacaaa ataatgccag gataatggta tgtgatcagc attacaattc caaagatacc  13320
aagacaacta cttatctgac acttgtctta gtatttctct aacatttatc taaaattatt  13380
tcaattattt cttttctcgg aatgcataac ttgactcatt gacttgattt atgattctca  13440
gatcaaagga aatgtaacaa cagggactag aaacactttt ttattcaatg tccaatgagg  13500
gttggggagg actccatcat tgactcatta tataattcct cataaactca ttacaattgg  13560
cctggctttc attaattcat gagcacttat tgagcaccac atgccaggcc tgtgctagtg  13620
ctggagatgc aaagacaagg gcaagttcaa tccatgccct caatgagttt acagcctaaa  13680
gacgactttg actaccaggc cttcattaca tagagcgaca tcctaggact tggagaatca  13740
gctttcctct ggagccttaa agacatccct atttactttt gtgtcttttc tttgaagaaa  13800
aacaaaaata agtatacata ggatacatta ataataaaaa aacagtattt tatgagactc  13860
agaatgctaa ttttaggatc tttgcccttc tcagttgact tttgtgtccc tcaactgttt  13920
```

-continued

```
agtctgcagg acagatatca catcctgctg tgcagtttat aaaatgtcct taaaattaga  13980

agaaagaaag gccttgtctt cctgggttta agacccacac atctgaggct gtaggcattt  14040

cagatccctc tggtggatgg accaaaatga taaacaatac tgtgagataa atgctttaaa  14100

catcatctgc tctttcatct gaattcccta ttcattattc ggcaacattc acagttttca  14160

tataacgatt tcagtagttc tagggcacca gaaaagcagt actaggaatg gccataaagc  14220

atagaatatt tataatctaa tgagggagac aactaaaaga aagaaggaat aaaagcatct  14280

tcaacagaaa caccctttac caaccaacta gaggtataga aatgatatta ggtaattagt  14340

gaccactaat ttaaagataa atatttattg agtgccagac attgttccag gcactgagta  14400

tatagcaata agcaaaaaaa acaaaacaaa acaaaacaaa agtgcccact ctcaatggag  14460

tttatattct caattgtgga gacagacaat aaacaaatat ttatatataa aatgtcagat  14520

ggtggtgaca ggcactatgg aaaagaataa agcagggccc agagagagag ggtaggatgg  14580

ggtagaggtg ggatggggtg gagggctgct gaggtgggat ggagtagagg gctgctatct  14640

cacctagaat ggtcaaggaa gtctgcacct atatgtatca cttgagcgga ggctctgaag  14700

aaagtgaggg aggatgaagg cagagaggtg agaagagagg attacaggaa aagacattgg  14760

caagtgtaaa atcctggggt ggaaatgtgt ttgcaagtgt gtctaaggaa cagctaggag  14820

gccagtgagg ctaaagccaa gtgagcaaag atgggagtgt gaggagatga caggtcacga  14880

tgggcacagc caacagtagg gtgggcagga aatcgcaagt cctttgaatt tactctgcag  14940

gagatgagag gccactggag ggtttggaac caggaggcac atgccctaac tcatttgaga  15000

aggatagcag tgtctggctg tcctgtgaag aagtggccat aggaggaaag cagggaagca  15060

ggcatttgca ataattcagc caacatatga tagtggcttg gtccagggtg ctggcagaag  15120

atatggcaag ggaggggttc tggacaattt ggaaggtaat gccaatagat ttgtatgtga  15180

taaaaagttg agaggacttg acgtgtacga gtggttaatc ttcataaaat ggatgaatgg  15240

ttaaaaagat ttccgcaaag aaactgtggg ttgaaggtaa aactagtaac tccaatgtaa  15300

gtgaacaaca gagaaataca aaacagacat ttttcctact cctacaaaaa ctgtaattat  15360

caagaagacg acatgaagtt tatacccagt attgttagca ggaagcctca ttccaagtag  15420

atatttttcc ttggccattt tagcaagtga gagcatgagg ccatcataat gaacaaatca  15480

tgccatcatg atttaaaaag aagcatctgg agttttagta atatagttag gtgagactaa  15540

aattatacta aacataaaat taaaatatct taacaatatt cttagcaatt tcagctttac  15600

catatccttt tgaaatctaa ttttgctata tgctttgtaa catagggtg ggggaaagag  15660

agaaatttat gagataattt ataaataaaa atacacctaa agtataagca ttctcaactg  15720

atggtcagaa aatatggaag gtattcaaaa ctctagcaga aacataccat aaacaagatt  15780

ttaagactga aagtagacgt ttagtggggt tcagggtgaa aggcaggggc aagaagctgg  15840

caagaagagg gaagggatac taattctaat ttgcctctgt aatgctttac atttaccaag  15900

gttccacaaa tggtatctga ttccatcctc atatcaaccc tatgaagtaa gtcagaaaag  15960

acgatgtctc ttttcctaag gaatgaattg agacttaggt tgagatactc tccagagctt  16020

actcagatag gaagtgacag ggccaggatt catattaggg cttctggctc cacagacagt  16080

tctccttaag actttcaata aatatgtttg acaaattaag tgcttactct cggctgagtg  16140

tggtactagg tggtgtggca gcatctcaaa aagggggaaa gtcactccct caattcccat  16200

gtggccttca gtctgagact agggagatta aacagatgcc tgagaagctg tttattacat  16260

ttacaaagca acacatttgt caaagtgaaa taataaattt agcccataag gactctgggg  16320
```

-continued

```
gcaaaaagta aaaattaagg cattagtcat tacagcaaat aaggttaaca ggtgtgatgg  16380
agctccttcg gcgtaagtca gcttaaattg acaagtaaag agagaaattc actggctcac  16440
agatctgata actacaggct ggtagggcat aagcaatatc atcaggaagc cgtgtctctc  16500
attacccaac actggtttgc tgtgcattca ttttattccc aggcatgttg tcaccaggtg  16560
ttggtaatct gaccccagca actcctggct aaatcccaca ggtttagctc tcacaataga  16620
aaagaaagca cttcttttct aatggcacca gcaaaacagg gtctgccaaa cttgggtttt  16680
gtgcctgtct ctgaaccaat cactagggta taggggagtg ccgtgctctg atggccagcc  16740
ctgggtcata tgcccattct tgggtagagg ccgggtcagt tccaccagat gagcatggtc  16800
tgaggaagaa gacggttgtt tttccagggg aaaatagaag tgccccccgct agaagggaga  16860
atggctgtca ggagggcaaa acgacagatt cactaaaata ggttgatgcc taaagaaaat  16920
aattttattc ctaaatttaa gggagtattt cagttgtttt taatcttatg gaattctaca  16980
ctgggaggga gttggtgcag gagattcatg atatgcaggc ataggctaca gaataatgct  17040
ttgagttttt atcctttact tttcctttcc tttaagcttt aaagacacga tttcttcatg  17100
cagggttgcc ctgaggtgag cctcatcatc tcttttttttt gagatggagt ctcgctctgt  17160
cacccaggcc agagtgcagt ggtgcaatct tggctcactg caacctccac ctcccaggtt  17220
caagtgattc tcttgcctca gcttcccgag tggctgggat tacaggtgtg caccaccagg  17280
ccccaccacg cccggctaat ttttgtattt ttagtagaga cggggtttca ccgcgttggc  17340
caggctggtc tcaaactcct gacctcaggt gatccaccca cctcggcctc cctgagtgct  17400
gggatcacaa gcatgcgcta ccacgcccgg cctcatggtc tctttattgt accttttcta  17460
gtctctgctt tcctgaagcc agaggtcttc ctatctccag aagctccaaa gacacacttt  17520
caaacccctc ccagtcactt ggccttttct gatgacttct ttccttcaag gctgccttta  17580
gtaaccgatt attgaagagg caagagaaag ccctcagcct tctccacttt cacctccctg  17640
ggctccccaa gtttggccga ctcctctttt caagttcaca ttttctcctt tccacagagg  17700
tttgcaacat tacctttaag aaatcatctc cagtctctat cacgtttcaa cagttcttta  17760
ccccatgctt ttatccctgt ctcccaccaa tcatatccac cggccctatt gaccgcttgt  17820
gggagttaga attttggaga ctggtcatat gtcacaaagt cctgctctag aaggcagaac  17880
actccatttc ctgctcctcc aaagcccttt atctctccag gcctctcctc ctgtagctct  17940
gaagctggat tgatgagatt cccagagggg agcatttagt gctctgagtg ctttgatgaa  18000
attgattagg taaatggaaa catatttttt gcaaccactc tagcctgtag aaacaataag  18060
ttgcaatgat ttgccatttt tgaaataatg aaggttcttt gtaattttaa atattctttt  18120
gccacaagag attgttttcc agcagtaaaa taaccagaat gtttgatttg aaatgttgaa  18180
aaaatatata ccgtctgata tctttagagc agcactttca ttatcaatga tggatttaac  18240
attttgttta atttttctag cttctctcct gaagggtttg aaacatgcca atattgtgct  18300
cctgcatgac ataatccaca ccaaagagac actgacattc gtttttgaat acatggtgag  18360
ttgttcgagc attttacaac acttgagaaa aataacctgg tacttgtata atgaatctgt  18420
taatatttta tggcatgata aaacttttat tataatgtga aaagtatcat ggaaattttc  18480
attattgtga ttagtagaac cttattgttc ccacatccat ctttggtcct gcttccttac  18540
ccatgacttt tgctgtccct tttcccctca tcagcaataa taaatgagga tcttgagttt  18600
accttctaaa taaaactttt gcacttattt ttaatctaat tttaatcact atctgagcag  18660
```

-continued

```
aatccaacat tttttcattg acaataaagg taaaaatcac aagatattta aaaattgtat  18720
gcaagcttgc taaagaataa ctcatgttgt atttttggaa gaaaaaatat ttaaataagc  18780
agaaagaact tataaggtat gtgtacttga cttgcctcca aggacacttg gagagtgaaa  18840
aattcctgcg tcgttgtgtt cagtgccagt catttaaaat gagcatctct gtgctgagaa  18900
acaggctttg ttctaagagc agccagttag aaagacacac tgtgtttgac cttaacagtg  18960
ggttctcaga aaacctggtt atattccttt tgcaccttat tcttaaaatt ctgtacttcg  19020
tgataccttc tgacagtcaa gtcaatgttc tgctttagga tgctatctaa gcaccactaa  19080
attcactcac ttctctttct ccgctgtttt atttagcaca cagacctggc ccagtatatg  19140
tctcagcatc caggagggct tcatcctcat aatgtcagag tgagtacgtt aagggtcagg  19200
accctctcct ggcttgccca cagaaggaga attctgaaac agactgtctc acaaagcaaa  19260
gtcctatgat actaaataag aggatggaca tcactgatat tccagaaaaa agttttgttt  19320
tgttttcgtt tttgtttttt tttaaaaagg aaagaaaaaa gaaaaagagt tgctgagttg  19380
cttcttaaga tatggagcaa tgttttctga gcaacctaat gctgtcagtc atggctacat  19440
gcaaatgtgc ctttagatga ataaacgagt gaaggagaat tatactaaaa ggaaaaaagt  19500
aaagctaggc catcaaaaaa taaatacctt cttcatatca gattactgtg gtctaaggtg  19560
aagtctgcaa tacttgtact agcagatcct attatatatg tggccctaac tcccattttt  19620
ccagtcatta gaatcaaaat aataaactct taattagcta taattctaca tctgttataa  19680
attttagaaa ccatttatat ttcatacttt tcattcccta aggttttatt ggcattaatt  19740
aattgattgg ctcttaaaat aaccgtatga aatttgtata tgatgtattt attcatttaa  19800
ctaatattta tttatgtatt catttattca ttcatttaag aaatatttat tgagtactta  19860
ttgcgtaata agttctgggg tttcaataat gaataagttc tgtttcttat tttcaatgag  19920
cttaaagtcc agtaagatat atgaacttaa ataggcagtg agggccagtc ttcaagcaac  19980
agcaatgcaa gatggcagcc accatgggct caggcaattt atgaaagcca aatatacagc  20040
cttaaaatag aatgtggacc taaataccca gaagaactcc cctttgtaag atttgtaaca  20100
aaaattaata tgagtagagt taatagttct aatggaatgg tgaacccaag agccatatca  20160
gcgctagcaa aatggcagaa ttcatatatc atcaaagtta tccttcaaga gcttcagcgc  20220
ctaatgatgt ctaaagaaaa tgtgaaacgc cctcagccat ctgaaggaca gtgttacagc  20280
aattgatcaa aaagaaaaac cacaggccct tccccttccc ccatacttga tgtaagcagt  20340
cttcattttc catagtagta aattttctag atacagcttg tagagctcaa agtactggaa  20400
agaaagctcc cattcaaagg aaatttatct taagatactg taaatgatac taatttttgt  20460
acatttggaa tatataagtt gttagcctgg cgcggtggct cacgcctgta atcccagccc  20520
tttgggaggc cagagtgggc agatcatgag gtcaggagtt tgagaccagc ctagccaaca  20580
tggtgaaacc ccgtctctac taaagataca aaaaattagc caggtgtggt ggcgcacacc  20640
tgtaacccca gctgctcgag agagtgaggc aggagaattg cttgaaccca ggaggcagag  20700
gtgcagcgag caaagatcac accaatgcac tgtagcctgg atgacagggc aagactccaa  20760
ctcaaaaaaa aaaaaaaaaa agaaatatgt aagttgtgct ataacaaata aataggcagt  20820
gagaagcaaa gtgctaaagc ctatgaccat ggtaactagg aatactgtgg gaacacataa  20880
taagggaacc taacccagtc ctggaagtaa ggttttggaa aggaatgttt gaggacaaag  20940
ggttaaagag agtgaaaaaa aaaattaaaa taccagttta gctgtgtgga gaatgggata  21000
gggagctaac tagagaaatc aaataggaat gtttcatggt atgttaagga ccctggtaag  21060
```

-continued

```
ggtgaagacc attacattat ctgcaccatc gcgggacttt tttttatgg taatgcttgg  21120
caatttaaat agaggagcag agaatgtaga cagttggatt gagtcagagt tgaagttctg  21180
ccagacatgt gaaaggaaga gacaggtagg caagagagtt gaagagatta tcaagacaga  21240
agttaatgtg ctggccagtg gcatctagtc tgagtctaat ctgagggaag gaagtgaaga  21300
taagcagctt gctgatagtt atgaagagag tggaaggctt caaggaccta caggtgttga  21360
ttaaatagaa gaatgattgg agaaagaata actgtgagag agtgagattt tcaggcttga  21420
gtgactctca cataccagac actgtgctaa atgcttcaaa gacatgatcc ctgccctcaa  21480
gggacttaca gccaaaaaca agagataaga aatacacacc aatactatta taggacactt  21540
gtgtagaata tcaagaaaga aatacgatct agtactgtag atgtgcaacg gcatcaaaga  21600
tatcttctag tttcaagaag tttcagatcg gccgggcgcg gtggctcacg cctgtaatcc  21660
cagcactttg ggaggccgag gcgggtggat cacaaggtca ggagatcaag accatcctgg  21720
ttaacacggt gaaaccccgt ctctacaaaa aatataaaaa attagccagg cgtggtggcg  21780
ggcgcctgta gtcccagcta ctcaggaggc tgaggcagga gaatggcgtg aacccgggag  21840
gtagagtttg cgtgagccga gatcgcgcca ctgcgctcca gcctgggcga cagagtgaga  21900
ctgcgtctca aaaaaaaaaa aaaaaaaaaa aaagtttcag atcttaaaca cactgcattt  21960
caacagtcta gaataggaga gcatgttaca gggagagaaa atgttttcag caaaggtaca  22020
gagtagggaa atagaggata tgttcaagga agaggacccc agagtcatgg tttgttaggg  22080
ttagaggaaa cacagtgttt tgcaatctcc aggttccatt agtgcgttat gaaatcaata  22140
tggtggttag caacctgcat tttaaaaaat gaaataaatg gatgagaaga gaatagaaaa  22200
tattagcatg cattacattt tgaaagagca agtattattt tctgcaactt ttgctccaat  22260
tgtaactgta cttatatttt tatgtatgga tgtgaatacc agatacatat atatttctta  22320
ctgtagactg cagtcaaaaa atctttaaag cactggcctg gtctaacttc cttattttgc  22380
agaggagaaa tccaagatct gagaggacaa acattttgcc tgaggttata gaaccagctt  22440
atgccattgc taaaagtgat tcttagttaa aattctttcc cactagtgcc atactgcact  22500
tctagttctg ttggcctgaa atacagaata tattagtgaa acagcataca caagtctggg  22560
gaaatatatt gggtaggtgg ctgagagcct cattttctaa gaaatgtgga ccttaggcag  22620
ggtatggtgg ctcacaccta taattccagc actttgggag gccaagtcaa gaagatcgct  22680
tgaacccaag agttcaagac tagcatgggc aacatagcaa gacctcatct ctacaaaaaa  22740
tttaaaaatc agctgagcat ggtggcatac gcctgtagtc ccacctacct gggaagctag  22800
gtgggtggat cgcttgacac aggagtttga ggctaaggtg agccatgatc acacaactgc  22860
actccagctt gagtgacaga ggaagaccct gtccctaaaa aagaaagaaa tgtggatttt  22920
attccttaga cagtacagtc attagtcatt aagtttgagt tgagagaaaa taatatgatc  22980
agaagaaatt tatatcactg tggtctgtag gatatatgaa aggaaataag agactagagt  23040
cagggattcc acttaagtgt ttgtttgttt gttttgagac agagtctctt tttgttaccc  23100
aggctagagt gcaatggtgc agtcatggct caccgcagcc tcaaactccc agcctcaaat  23160
tatcttccca gctcggcctc ccaaagtgct ggaattacag gtgtgagcca aagggtttat  23220
tgatgtggtc tggcctagtg cctctcaaac ttcagtgagc agacaagtga ccgggaacct  23280
gactcaacaa gtctgggttt aagcctgagc ctctgcattc taacatgagt caagctgatg  23340
cagatggtgc tggtcaagag ccaagcactg agcagcaagg atctagttag caattagtaa  23400
```

-continued

```
tcaaggttga tattatggta gtgacaataa gaatggagag gaatgtgaaa atcagtaaca  23460
aagaagagtt cacctcttgg taatgtgagc atgaggaggg aaaggatggg gccaaacata  23520
actggttttg tgtttgactg acgaggagaa ttgtagctct attaacagaa ataggagaag  23580
aagttggttt ggagagaaag aggagtcctg tttcagacgt gttgaggtcc caggtgagac  23640
aggatctcca aagggaaatg agcagtaggc aacctaaaag gaaatctgtg ctcagaaggg  23700
agctgtgagc tcgacgtgta gatctgaggg tcatcagcac atagagttta gaagacaagg  23760
agtaggcaac caaaagagca aatacacaaa gagaggagga ctgatgatga gacttttgcc  23820
ttttaggatg agaagaggaa caggaaatga aggaatgaag ggaagcagct tgtaggaatg  23880
tagagcatct gaaaaaaaaa tacacactgt catggaagtc aagggaagaa gaatttcaag  23940
aaggagggta tggtggacag tattacaagc atcaggaata cagctaaaag tcatactctt  24000
gactgcattg accttgtgga tttgtgaggg acacactaat aaataaagga atttattgtg  24060
ggtatatgga ggcacaaagg aagaggttat ccaaatcaaa gcaggtggga gtagggatga  24120
gttctccaag gtggaggcat cagtgaatgt gggaaggggc acagagcatc catgcccatc  24180
ccaggcaagc caccctccag aagcctccat gagagttcag ctatccagaa ggtctctgta  24240
ccctaatctt tctgggtttt gcataggctt cattgtgtag gcatgattta ttaaactatt  24300
ggccactggt gatcaactta accttcaacc cctctcccct ccctaatcat gccttggtct  24360
ttccagtgac cagtccctat cctaagctac ccaatggtct gccagctatc agtcaactct  24420
acaaaaagac atcactttgg agattctaag gattttagga gttggctgtc aggaatttag  24480
ttgaagatca aatatatatt tcacaatatc acagtcgtgc tattttatat caggcgccat  24540
taaatggttt taaacaaaga ggtgataaat tcagattttc tttttataaa gcttacactg  24600
atgacagtgt ggtgaataga ttgggatgag ggcaatactt tttttttgaa atgttatatt  24660
cccctgaccc tactttctcc ttgttttctt ctacctctct ccccctactc acacagaaaa  24720
cttctctccc tctactcatt ccctgaatgc tggtgtctgt taaggttcca gccttgacag  24780
tgaggctaat cagaaccaca gtggtacaga tgtgagatga tggtgggaga aagtggacag  24840
atatgagacc aattacttag ccggaactga cgggaaaaac aagagtcagc gatatttttt  24900
tctggatctg agtattaaaa tggatgatgg tgccattcac tgtgatagag aatcagaaag  24960
aaaaatttat tttggagaga taccatgaat tgtgttttag acatgctaag tttgaggtga  25020
ttatgggatg tacaggcgag ctccagactg tgtgggccta aagtagaaag gcaatctgag  25080
ttggagataa agattttgaa atcatcagaa tacggttgtt cattagagca ctgtcagtgg  25140
gtaagatagc taagggagca tgtgtagagt gataacagaa gatcaaagac ggaaccctaa  25200
gaataacaat atgttattat ttattatttt attatgtttt attttttaat tttattttta  25260
tttatttatt tatttttaga cgggagtctc gctctgctgc ccaggctgga gtgcagtggc  25320
gcaaactcag ctcactgcaa cctccgcttc ctgggttcaa gggagcctcc tgcctcagcc  25380
tctcaagtag ctgggactac aggcacccac cacctcacct gactaatttt tgtattttta  25440
gtagagacgg ggtttcacca tgttggccag gctggtcttg aacttctgac cttgagtgat  25500
tcacctgcct tggccttcca aagtgctggg attacaggta tgagccactg tgcctggcct  25560
atttttgttt tttatagaga tggggtcttg ctatgttgcc caggctggtc tcgaactcct  25620
ggactcaagc aatcctcctg ccttggcctc tcaaagttct gggattacac atgtgagtcc  25680
ctgcgcctgg ccagaatatc aatatattag attttagtag aagtagaacc tatgaaaaga  25740
acagccagag gggcagaaga aaaattagga gattgtggaa ccaaaagaag agagtgcctc  25800
```

-continued

```
aggaaggaag gcatggtcta tgatgccaaa tgctgcaaag ataaggaata agaagtatcc  25860
attgggtttc ataggaaaag tcatgggaaa ccatggtaaa aaaacattgt gaatgacaca  25920
atcgttgcaa aagcattttt ataggggat gaattttgta tttcagagga caaacagttc  25980
catacaatgg caagatctag tgtgtgacca cgggagttag tgtctgaagt ggattggaga  26040
agcagatcat tggagctgag gttggctaga gctgttctca tggacactaa tgtcatggag  26100
tcaacagctg tgatccaagt gcccacatct tcagtgaatg acagagaggg attgagagtt  26160
cagtgaatga ccgctaaaag aagagtaatg gaagatgtgg ctggatggca ttaaaatcca  26220
agggacaggg gtttttactt aaaagtagag aagtaatggt tttgaagtgg tagtggggaa  26280
aagggaggca gcttatgaca cttgtcagtg gtcaaaggta tgaggaagtt atagaaaaac  26340
taacatccac ttgagaatat tatagggaag cagtgagctc aaggtctcat ttaaggaaag  26400
gagccaaaag gaaattcacc agaggttagc ttttaggtag tttttaaagc aggattgaag  26460
aatggagact aaacagtgaa aatgtttggg agagagagga gcaatagata tgaggctaaa  26520
cagaggaagc acagaacaga atggagatga gtatgttggg aggaaaagga atagtcagag  26580
gcttatattt tgagttgtga ccaaggaaga cagggtggga atcctcgtga ggttatcttg  26640
tttcagattt ctagtagaat gagtcccagg gattccaggg gggatggaag gactcaggct  26700
tccctataag gagttggcta acggatctca ttggtttttg agtaactcct ggcccagatg  26760
gcactagttc aatggaatta ttttgttccc ccaaaactta ttgagttgga aacaggtcta  26820
actcctggga tctgggaagc ctttctggaa agagtcaccc acgatctggc tgatgttgaa  26880
ctgtgcagac accatcatat ttggttatgt taggatgcaa taattggtga agcttctgta  26940
gtgttgaatg aagaatccag gttggaaggg atgaaagggt gagtgggtga tgaggtttgt  27000
cagcacagac tgcaattttg agaaatgtgg ttataaaata ccatacctta ataccgcagt  27060
gctttaccac tcacaaatgc ctgtagacgt atctggcaga gaggaaaggg gttgaatggc  27120
aagaatgtgg gaagggactg tggctagtta gtgaaaatag tctacacttg ggacataaaa  27180
ggcatttcaa gctgacctac taagaagctc tgtctctgac tcagccagct ggctctctcc  27240
ttccctgtca tgttttcatt ttctgtcttt tctctagttt ctcaggatgg tatagtggag  27300
tcagacaagt ctgaatttga gtcttggctc tgactattcc tagacatgtt ttaaaagtta  27360
cattgagccc tggttttctc tgtaaactga ggataagcat gctatcccaa aggttgtatc  27420
cctcactggt caccagcttc ctgtcttcta tccacctgtc ttcctcttcc tctttcccta  27480
gtcctgcata ttgaaaaaca tttttttttt tttttgagat ggagtcttgc tctgccaccc  27540
aggctggagt gcagaggcac gatcctggct cactgcaacc tctgccttcc aggttcaagc  27600
aattctcctg cctcagcctc ccgagtagct gggattataa gcatatacca ccacatctgg  27660
ctaatttttg tatttttagt agagatggag tttcaccaca ttggccaggc tggtctcgaa  27720
ctcctgacct caggtgatcg gctcgctttg gccttccaaa gtgctgggat tataggcgtg  27780
ggccactgcg ccagtctgaa aaacgtattt ttaagcacat actatcgtat cttcttgtct  27840
tttacctgga atttaagctg gttgtttgta ttaccttttc catggacatt tatatttata  27900
accaatcaga aggtttaaat gtcagtgtag gaattttgtg ctatggaagc ttcgtggctt  27960
ggtgaatggt aaaatgaata atgtgtgtat atttgaagca tcagaaagag aaaatgctgg  28020
gaagattcat agaaccagtt aacatttgaa ctaggagtca taagaaattt ttaaaattct  28080
taaatggttt atgaacctga tgtggtagct acatgaaacc tgcatagctg caggtatgct  28140
```

-continued atggtaggta aactctccat gctcctgctt ccattggacc atttggctcc aatgtctcca 28200
ggtctttgtt agatcaatac tggtcctagc atctctgaaa gtcctagctt tctaagatgc 28260
tgttgaaaaa gaggattaat ccacataact ctgcatctgc cattttgccc atgtcccagg 28320
aatgctgggc ctagcccttc ctttctgaac tgccagaaca cgttctcagt tgacatacgt 28380
ctttgtaaat actgatgttg gtgtttgaat tctcaattgc caatggcact ggaaaatagc 28440
aaaagatact tggaatacta agcattcttt ttttcccgta agtttctgta gtgatgggaa 28500
cctagtaatg gctttggttt ctgtgcctca taaccacatg aaacattttt aatttggggc 28560
tcagaatgtg tttttccctt ttatttctcc accactacca tttacccttt ctcccttctt 28620
cctcctacaa tttgttcctt attctttttt gatttttttt gagggggggg ggtctaactt 28680
attttggtct ctcttccctt ttcatctgta ctgtgtattt cccttgtttt caactttgaa 28740
tttaagactt taaaaatagc tttaaaaaga taaagatttc tttattttct aataccatct 28800
aaagatatat tttttagtgt ggtctccttg tgttgtgttt ttaaaagggt ttcatattgg 28860
agagcctgga aaacttaagc agttgtaaac tttagaatat catttccagg tcaactttga 28920
tcttatatgc caagttcatc ggtggggaaa aaaattaaat ctttcacatc taaatcaata 28980
actagtgttc caaaggaaac ttcaaagttt cactttagat ttttaaagaa gggtaattcc 29040
ttcagtatca aagaaatgag atgtcaggaa aagccagaat ccctttgttt aggacacagt 29100
ctagttactt gacttttctt gtccttttc ttccccctct gaatgtaaaa atcttcttct 29160
tcttcttttt tttttttttt ttggtctctc aagagacact tttactatat tctttgagat 29220
gactgttttt gatttagagg cgaaatcagc acgtggtggc tcaaatctcc ttatggatag 29280
tgtttcttcc ttccagcttt tcatgtttca acttttgcgg ggcctggcgt acatccacca 29340
ccaacacgtt cttcacaggg acctgaaacc tcagaactta ctcatcagtc acctgggaga 29400
gctcaaactg gctgattttg gtaagtcgcc cctcgggtct cattctgggc tgtgaacaat 29460
gatgcttttg tgtgcacttg tttaagcgtt gactgggcct ggcctttgaa aactggaggc 29520
ccaagaacat gatgctttgt gaggatatca aactaccaca aaggaagtgt gaggcacgaa 29580
acagggaggg attggtagct ttctaggatt ccaccaagtc ccagtttagt cagatggcca 29640
aaagctgggc acccttgctg ccccactgcc agttttgata tagagacatt ggtagagtaa 29700
actgtactta gtaagttttc ctaaatctaa gtgaatatac aaattatatt ggaatagatt 29760
gagattatcc caagatgata aagaggttaa ccccagattg tagcatggac tcctgtcagg 29820
atggagactc caggacactt gttcctgctc tcctaccttc tttatataag tgtgagatgc 29880
aaagttttat tcccattaaa gtgaagcaga tttcctctaa gtatcactgt atccttccat 29940
tttagcactt atcgcagttt ataattatat tcacacacat aaatacatac atgcatacat 30000
acaaatatat atacatgtgt gagcacaccc ccacacacaa atatatatag atttgcgtga 30060
tgattttgtc tcaactggac tgtaagcata atgagggcag cctgggtttg tttttgctta 30120
tcattttatc cttagtgcct ggtaccatag taggtgctta ataagtactt gttgaaaaac 30180
tggctctatg tgagctaagg aaccactctt ctctgtttgg cagatgccaa atggtgatac 30240
tatcactgca gtatttattc tgagatggca gcttttatcc tgacatgtaa gcatttaaca 30300
gatatttgtt tatcaattct ccacaatagc aaactcatct attgaagttt ttcccaacaa 30360
tagatcatgc aattctgtga gataaacagc tgactgacag aaagactcat tttgcagaac 30420
agtacttaga aattcatcta aggtcctacc aaactaatta atttggatga gcagtcccta 30480
ccgtttatct actaaactgg gctttcctgg agtgccaaaa cggaaggtgg ccatgttagt 30540

-continued

```
catgaacagc tcagtttctg ttacagagac ccaaaattac agaggtataa catgctagaa  30600
acttaacttt ctttcgcatc acagtcctga cctaagcagg cagagcatgt atggtggccc  30660
catgctatct tggcccaggc tgcttctgtc acgtggctcc tccatcccca attgtatgtt  30720
tcaagatggc tgccacttcc tgctcatcac agcccagagg agggagaaaa gagaagcaga  30780
acccttaacc cctccactaa ggcataatct ggaagttcac acatcacctc tgttcatatc  30840
atataggcaa gaacttagtc acctgaccac acccagctgc caagaaggcc acatctagct  30900
gcaaagcagg ccaaaatttg agaaattcac ttgatgaagt gatagacaag agtcaagata  30960
gtgattagtt ctactaaaag cacctaaagt ttgtgtgtta ttttttctaa tggtgtttac  31020
cctggtccag tgcatcatgg tgcaagccaa ggtccagaac gatgggtttt atgcttttcc  31080
cttttggaca ggtcttgccc gggccaagtc cattcccagc cagacatact cttcagaagt  31140
cgtgaccctc tggtaccggc cccctgatgc tttgctggga gccactgaat attcctctga  31200
gctggacata tggtaagagt ggtgccgaga aaatgtgagt catcctactc acgagggttg  31260
ctttatcatc tacattatat tttaataata attctaaaaa tggcaatcac gtatatattt  31320
ttatatatat ttatatttat atattttata tatatttata tagttatata tttatatttt  31380
atatatttat atatttatat atatttgtat atatttatat atttatatat ttttatatat  31440
ttattatatt tatattttta tatttttata tatttatata tattttatat atatttatat  31500
atatattata tatatttata tttatatata tttatatatt tatatatatt tatatattta  31560
tatatattat atattttata tatttatata ttatatatat tttatatatt tatatattta  31620
tatattatat atattttttt atatatatat atatgtattt tttttttttg agatggagtc  31680
tcactctatt gcccaggctg gagtgcagtg gcacgatctc agctcactgc aacctccacc  31740
tcccagattc aagcaattct cctgcctcag ccttctgagt agctctacta aaaaaatact  31800
aatatttgta gaagattctt gcaattattc tataaccttt tactgttgaa ctgagaccca  31860
cagagttcct gcccaaggca tcttctgaat ctgacactct ttttatgtta ttttattttt  31920
tgagattggg gtcttgctat attgtccagg ctggtcttga gctcccaggc tgaagcagtt  31980
ctcccacttc agcctcttga gtagctggga ctatagggct gcaccactgc accctggcaa  32040
tctcatgctc tttctttcac gcctttcctc ctagctcctc tctttaatcc tttgccttgt  32100
cttctccttg acaccttatc cacagagaaa caaacatata tccccaaacc acagacacac  32160
agatgtgtgt gcacgtgcat gtgcatgcac acacatctgc atgaacatac tcacacatgt  32220
ccaaacgtag ttcagagcct ggtttaggaa aaaaaaaaaa aagcataaag accaagcttc  32280
aagacacctg attttcatgc cagttcgatt tctaatcaat taactctgga ttctgttatc  32340
ttgaaaaagt catgtatcct ctctgtgtct atgtttctcc atttttaaaa atgaaggtaa  32400
taaactctct ccatctgagt taaatggaat tgtagtacaa atataagaac caaataggtg  32460
gctgggcttg ccgtctcatg cctgtaatca cagcgctttg ggagaccaag gctggaggat  32520
cgattgcttc agcccagttg tttaagatca gcctgggtag cacagtgaga tgctgtctct  32580
acatttttta aaaaaattag tcaggcgtga tggctaatta aacacttcag gaggctgaag  32640
taggaggatc tcctgagcct gagaaattga ggctgcagtg agttttgatg gtacccctgc  32700
aatccagcct gggttacaga gcgagacccc gtctgaaaga aagaaagaaa cagagagaga  32760
gagagagaga gagagagaaa gaaaggaaaa gagaaggaga ggggagaggg ggagaaaggg  32820
agagggggag agagggggag aaggggagag gggggagagg tggggaggga gggagggagg  32880
```

-continued

```
gaggaaggga aggaaggaag gaaaggaagg aaggaaggaa ggaaggaagg aaggaaggaa  32940
ggaaggaagg aaggaaggaa ggaaggaaag aaggaaagaa tccagatagg tgctatcaag  33000
taaagccaca gagttgggga ggctctaagg ttaatgggtt acaatagtga gcatgggctg  33060
tcagacatgc atcatcctag aacggcagtg ttattttctc tggatcatgt tcctggagac  33120
ttcccagtca tttgggggcc actgttagat atgtgatgac tttacagacg tagacaactc  33180
cccaaaggta aggaaatata tgaatctctt tcagtacctt ggaagaaagg gtttatataa  33240
aaacacaaag ccccattttc aaaaatccat aattgatttt aaaaaattaa atggtgtcct  33300
aaaaggctaa actaagcttt tagatctccc aaagaattaa gaaaggttgc agacattttt  33360
ctccagtgta gagtcattga tttctgatac ccagtacaat ttatagaaat atcatctgct  33420
agtcaaaacc ctcctgaaac tgtcagctca caccgctcag cactgtcact tcaaaggact  33480
ccggcaggct ctggcttact cagctcttaa tgatgtcttc ctgattatgt ttcacagagt  33540
gaaacttcta cccgtcaatt ttaaactaat tttattatgg aatagttaaa acattcaaga  33600
gtatatataa catatatgta gatcagtgat tctcaaccag ggagcaattt tgctctgcag  33660
gggacatttg gcaatgtctg gaaacatttt ttgttttcac agctggggt ggggtggtgg  33720
ggggtatcac tggcatctag tgggtagaga ccagggatac tgctaaacat cctacagtgc  33780
agaggacagc ccctgcaaca aagatttttc caacccaaaa catctgtagt atcaagatta  33840
agaaagccga tgtaggttaa gaagcttaat ttacttttag agacagggtc tcccttggtt  33900
gcccaggctg gagtacagag gtgagattgt ctcactgcag cctccaactc ctgggtttaa  33960
gtgatcctcc tgcctcagcc tcctgagtag ctgggaatac aggtgtgtgc caccacacct  34020
ggctaattaa aaaaaaaaaa gtgtagagac agagtctcac tttgttgccc atgctggtct  34080
caaactcctg gcttcaagag atcctcctgc cttggccttc ccaactgctg ggattacagg  34140
tataagccac cgtgcccaac caattaagaa gcttaataac gtgaacttca taacctgcta  34200
cccagtgtaa caactagaac ataatccgta ctgtcctatc aactgtgtcc ctttcccatc  34260
aacctgcccc tccactagaa ggccttctac caaaattttt tttccttttt tcatcagtat  34320
tctcatatct ttttaaaaat aatcctttta cattttagag gtattcttaa aaatattttt  34380
ttgttttact tgattttaag ggttgttttt ttttgagacg gagtctcgct cgtcgcccag  34440
gctggagtgc agtggtgcga tctcagctca ctgcaagctc cgcctcccag gttcacgcca  34500
ttctcctgcc tcagccatga tgttatattg cttctagtct tctgtgactt ggctttgttt  34560
cattcaatat gttacatgtt tctaagattc atccatgttg atctgtttag ctatacttta  34620
ttttctgtta gtgaatattt catttttttt aatgtctata gctttgcaat aatacttgat  34680
accttgtagg ccaagtctcc cagcctattc atcttcttca tgaggataca tcagataaac  34740
ctagtttaag ggacattcta cagagtaact gacctgtact tattggaagt gtcaagattt  34800
taaaagataa agactgagga actgttccag attaaaggag actccagaaa cctgccaact  34860
aaatgtaacg catggtccta gattggatct tgggggagat ggtgctctaa agaatactgt  34920
agggactata ggtgaaattt cagtagggac tgtggattag ataggggtat tggatgaatg  34980
ttaaatttcc tgattttgat aattgcactg ttgttatgta agaggatact ttggttctca  35040
gaaaatacca acataattat ttagggatga agagtcatga tatctacaat ttactcccta  35100
atgtttcaga aaagatatag acagacagac agacagacag acagacagat agatagataa  35160
aataacgaaa caaaagtgac aaaatattgg cgatggatga acctgtttgg aggatataag  35220
agagttcttt atactgctgc aactttteta taagtttgaa attatttcaa gattaaaagt  35280
```

-continued

```
tgcctccaaa ttgcgaaatc cttgctgttt catcaaagtt agtgtaagac agcactagcc  35340
taatatgtga tcagtgtttg taatttcttc atgtgtgttt gagaagaatg tgtgtgtcca  35400
cccaaatgtt gagtgctgct ggggtttttt ttttgttttt gtttttgttt ttgttttttt  35460
tgagacagag tctcactctg tctccatgcc tggaatgcag tgactcaacc tcggctcact  35520
gcaacctcca cctcctgggt tcaagcgatt ctcctgcctt aacctcccaa gtagctggga  35580
ttacaggagc acaccatcac acccggctaa tttttgtagt tttagtagag acggagtttc  35640
gccatgttgg ccaggctggt ttcgaacttt agatgtcagg tgatcagcct cccaaagtgt  35700
tgggattaca ggcatgagcc accgcgcctg gccaagtacc catttttaca tatgttcaaa  35760
aattcaaggt tgctaattat attatccaaa tcttctttat attatttttg tctttttaac  35820
ctaccaatga aaggtgtgtt gaactcattc actatattgt tgatttgtca gaattctatc  35880
cacttttgct ttatatgctt tgaagctatt ttcactaagg gcaaataaat ttaagactgc  35940
tcattattcc tttgtacact ttagttacca ctttcagaat aattttcatt tctcctgaaa  36000
tacatctttt agagtgtttt gttttgtttg tgtgtgtgta ggcctgctgg tggcaaattc  36060
ttcgtttttg ttttcagaag ataaacccta attattgaaa ggtggttttg ttggggatgt  36120
gattctagac tgacagttat tttctctcag aactttgaag atgtcattcc ccttctttgt  36180
cttccattgt tgctgtcgag gagtttgctt ttagccttat tatcttcctt ttgcaggtga  36240
tctcattttc tctggatgtt ttaaagactt ttttctttgc ctttatgatt atgcagtttt  36300
ctctaggagt tgtccagtgt ggatttcttt ttacttaccc tgtttggtat atcttgtgtt  36360
tcttccattt gtgaattcat gtctttcatc agccattttc tttttgaata ttgactctat  36420
tctattctct ctctgtagag ctccaatgaa agactattag accacattct tctgttatcc  36480
atttctcttc tctccttcat attttccatt tccttaactt tctgtgatgc attctgggta  36540
atttcttcag ctcatctacc agttctttaa gtctctctta aactatgtat taggttggtg  36600
caaaagtaat tgcagttttt gccattaaaa gtaatggcaa aaccatagtt gcttttgcat  36660
caacctatat ctcttacctt tttaccacat atacaaaaat gtatgttatt ctatgaataa  36720
gtgtttcatg aatttaacca tgagcaacaa tgacacaata taaaaatgca gttataagtc  36780
aaaattattg ttattactct tattcattcc atttgattgt tgttttcctg gtaaaactaa  36840
aaatgtaatg tagaaataga acaatatgca tcttccattg agctcactat atttgtttac  36900
cctcaaagta attgctagac cttgggtatt tacactgaga tccctctcct cccatttttt  36960
tctttttctt ttcagagtga taagagggga agtgagaagg gagaagattt ccagttgaca  37020
aagaatgaaa aagaaagaat aatcctattc tgctaggcca tgcaacccca tagggtccaa  37080
agtgaatgcc cttgtaggag gtagatgaca ctgggtgagc attagtgcat ttgtcttaaa  37140
gaaaccaatt ataacccgta gtgcagagcc tctccttcac aatgaggcct ggtggcagca  37200
gtgtcagtag ggggccagag caaataaaca ggggctctag ttaattatgg aaaacttgca  37260
actaggacat attggttatt cccaaagctc ccaaccaaca ttctctcatc ttctgacgtc  37320
ttttcttctc tctctttctg ctacctttc agaccttaaa agattccatt agtgacttta  37380
gtgagaaaaa tgcaatattt taggattatt aaatggtgtg gtttttagtt ttttgtattg  37440
tgttaaaata tacataaaat ttaccattca tcacgatttt caggtgtaca attcagtggc  37500
attcagtaca ttcacattgt tgtgtaaccg tcaccactgt ccatctccag aacttttcat  37560
catcccaaac tcaaactctg cacgtattaa atgataattt cccattaccc cctctcctca  37620
```

-continued

```
gtccctggta accacgattc tgctttttat cttgatgaat ttgactattc ttggtacctc  37680
atataaaagt ggaatcctac aatacctctt ctgtgtctag cttgttttgc ttggcataac  37740
attttcaagg ttcatccatg tcgtagtaca ctgagttttc cagaagcatt tatttcagta  37800
cacaaggtca tctattcagt atcagtttca ggcagctgct ggtgttagga ctagagaaag  37860
ttgtctctgc ctaacagatc atttactgtc acatttctcg ctgcaaactt ccaaatataa  37920
aaagggtggt ctagagaaaa gcaagtgaga atgtcatgtc actgccatat attacgttat  37980
tctgaattaa cttcaacagt aagaaatgaa atactgattc atttctccca acaacatttt  38040
gatattctcc ttgcacctcc aaaaagccta aaactcccga gatggatttt ttttctccag  38100
ggactgccta aggaatctga ggaatctttc cccctcttat ggaagaattt gttcatgctc  38160
agaatagaga aaaagtagga ggagaaccag aaagaggaga aaacatctaa gcagtttcct  38220
ctaacttgac tgaagaacca catttggaac aataaaatga cccagcacat ctctcccttc  38280
tggaagggtt taatgtttga tgtcacaggg tcttttctcc cctgcatatg aatttcccct  38340
tcgtctacac gggctgcccc acgggtatct ccacacagca gaaatcctca gagaagctta  38400
aagatatgta gggtaagagg agccccagga atgaagattt aaggacaaaa cagaaaaata  38460
aaaggaaata gaagctggtt ccctatctgg acttgaatgt tcagaatatt taaaatgttt  38520
gctttaagaa tagtctgtgg tgggcaaaat agatgatagc cacatgactt gtattcctaa  38580
gggtaagaag caaattaaaa aaaagaaaca gttctgaaca gaaatgaaaa aataagataa  38640
attgcatagt tctttttttt tattagatgg agtctggctc tgtcgcccag gctggagtgc  38700
agtggtgcga tgtcggctca ctgcaacctc caactccccg gttcaagtga ttctcctgcc  38760
tcaacctcct gagtagctgg gattacagga acacaccacc atacccggct aatttttgga  38820
tttttggtag agacggggtt tcaccatgtt ggccaggctg gtctcgaact gacctcatga  38880
tctgcccgcc tcggcctccc aaagtgctag gattacaatg cttacaccta gaacagatct  38940
gtcacctttc aaacttacag tgtgggcttg ttttgttatc aatgcattga tatttacagt  39000
acctatggat agtccatgta ctgaaataaa attgatttag gaattttgtc ttataagtgt  39060
tctaaagact tgcacaagtg cacacataca cacactatat acatagtgtg tgtgcatgtg  39120
cgtgtatata aatgagtaac cttagactta gatttgttag atgaggaagg tttcaacctt  39180
ccccaaaatg caaatggaga atttcaacca tataaaccaa atattggcat tttatctctg  39240
gaacacaaac atcttgtgtt actttatggt acttacgtaa tggcctgaat gctctagttt  39300
ttgccaatat attttacata attttgtata caagtttagt ggtatagaag ataaaggaca  39360
ctaagcagga ttaacagctt ggttccctac agctgttaag tatgaaaaca caccatgaaa  39420
aggcaacaag cttcttccag gcaatggaag gctttttggg ggagaaaaga aagtgaatta  39480
caggtttaaa cctaggaatg tcattttttg aaacttgttt aaaatatttt caatccttct  39540
agtggtttgt gagctcctgg ggtttctgga aggtgtttgg gaactggata gagggttagt  39600
tcatgccttt aaaagccaat acatttccat ttctctttta taaccaagta ataacccaat  39660
tatgcatgta ttttatatac acagacacgt atttattttt actccaaaac aaaatggtct  39720
gaggcctttc aagaaagtgc atgtggcgaa gtcatggggg gcagggtgga gaccatttgg  39780
tggtgcccac taactaggtt tctcagttgg cttatctctt agtggaccat tgctagcaac  39840
cagggtgttt ttaagcattt gacagttttc catcactttt atttgccttc atatattgtt  39900
tcatttacac ccttagtatc tcttgtttta aagacaggag acaaaaagaa catggatatt  39960
taaatacaag ttaatgagga actttaaaat aataataatt ctacaaattt acctcaagat  40020
```

-continued

```
actttaccaa attcataagt tacatttatc tgatcaaaat tcttgtgtca catatcaaga  40080
tgtttcttat acagcagaaa tcagtagaaa agaaaaaata ggccaagcgt gtggtggctc  40140
acacctgtaa tcccagtact ttgggaggcc aaggcaggag gattgcttga ggtttggagt  40200
tcaagaccag cctgggcaac acagtgagat cccatctcta ttaaaaaaat tagaaaagaa  40260
aaagaataaa atggggctgt tatatccaaa ttggcttttt aaaaatcagc aataaggccg  40320
ggtgtggtgg ctcacacctg taattccagc actttggaag gctgaggcag gcggatcaat  40380
tgaggccaag agtttgagac cagcctggcg aacatggtga aaccctgtct gtactaaaaa  40440
tacaaaaatt agccaggcat gctggtgcat gcctgtaatc ccagttactc aggaggctga  40500
ggcaggagaa tcacttgaac ctgggaggtg gaggttgcag tgagctgaga ttgcaccact  40560
gcactccagc ctgagtgaca gagtgagacc ctgtctcaaa aaaaaagaaa aaaaaaattg  40620
gcaataaaaa caacctgttg cttgctggag gaaaaacctg cttgcaaagc tcagtctgat  40680
atcatttttt aaacaaaact ctaagaacaa gccagtcagt taagctaaaa ccaaatattt  40740
gattatgaaa agggtttttg tatattttta caggataaga tacaaataaa tttcagtctt  40800
tcttttaata tgtatttctg ttcccaaacc agacacaaag caatttttaa acttgatcgt  40860
caagaaatct gttttctcct acacaatcaa tgaaaagtaa tctaaacagt gtttgtcagg  40920
ccaggcacag tggctcacat ctgtagtcct agcattttgg gaggcctagg caggtagatt  40980
gcttgagccc agaatttcaa gaccagcctg gacaacatgg cgaaacccca tctgtattaa  41040
aaaaaaaaaa aaaaaaagac catatgtctg cagtcagatg gaaaaagtaa aaatatgtaa  41100
taaacacata tgaataatat taaggaccat attttaaaat aaacttgata ataaattttt  41160
aataatatta tctacgataa aatgttttac ttaaatttcg ttctttatca tgccacacaa  41220
aaatggcaaa atgattaaga gagtttgcaa aattatgtgg tatagtgaaa gaggtttgcg  41280
gttaaaaaaa aaaaagagag agagagagag aagtatgggg ccatggggat agtctctgta  41340
atcagtcacc tgaaccactt ttaatactca aaagacttat gagaataaaa atctgatttt  41400
tgctaagatt tattagcaaa ataaatctta ctccttcctg tccctctcta attatccttc  41460
agcttgacca tgtatgaaag aaaatttaca tttcactgtt taatctattt aaagatgaac  41520
atttcccatt aaatcaggat gcaccttata atcagtagca tctaacaata taagtcagcc  41580
aggctgcagt tgtgactgta gttagaattg cacatgtgtg aacatcaaat gagccagcat  41640
caaaacgtgc agaatggcca ggcacagtgg ctcacacctg tgatcccagc actttgggaa  41700
gctgaggtgg gtggatcact tgaggtcagg aattcaagac cagcctggcc aagatggtga  41760
aatcacgttt ctactaaaaa tacaaaaatt agccaggcat ggtggcaggt gcctgtaatc  41820
ccagctactt ggtaggctaa gtcaggagaa tcgcttgaac ctgggaggcg gaggttgcag  41880
tgagctgaga tcgcaccact gcactccagc ctgggcgaca gaccaagatt ccaccaaaaa  41940
aaaaaaaaaa attgcagaat tggtgtcagc gacttggaag aaaattctgc aaagaaaagt  42000
cctttttttt tctttttttt tttaaactcc taggaaccaa atggttgtgg agaaggagta  42060
aatcagacat gtttagcaac attctttaag caggagtcaa aagtaagcta acactacata  42120
actgcaaggc cagcttagga gcccaggacc aatgactctc tgttgtttta tggattattt  42180
taagaaatgc tgcatcatca aattcttaat atagaggatg atacatgggt aagtgtagac  42240
atcaaagagt ctgagtcaaa tgctgaatgt gaaaaagttt taggaatacc gaaaccaatt  42300
tattttgctt aatgtttctc tttttcgtgt acaagtatgc tatatgagaa aataatctct  42360
```

-continued

```
atttaattaa atttataaca gccctttcaa taagtataaa atgaacattc tgatcatgtc  42420
atagtttaac ttgcattttt ttgtcttaat ggcaaaaaac caatgacgct tcttacaatg  42480
atagcatctt agactcaatg aaaagtgggg atgaaatgaa atttggggat acagtacttt  42540
cccctcttct cctaaaacag ataatgagct tgaatgatct acaatgtttg ctaactctac  42600
tgctttccta actgctgctc gtggtgttcc attttaataa aaagctgtgg gctgttctta  42660
ttttgtttga catagggact ttttttttgg cccaagactt ttaatatcat gtggtccgta  42720
tttaactctc cctaaaatat ttcttgggaa gagaaattct agtagttcag tttcgcttgt  42780
atgatttctt tcaaagtgtc aatttactct tatttccttt gctaggggtg caggctgcat  42840
ctttattgaa atgttccagg gtcaaccttt gtttcctggg gtttccaaca tccttgaaca  42900
gctggagaaa atctgggagg taggagaata attcttctaa agaaaatgaa atatctgcat  42960
tttaagtttt gaaccaaatt tgccttacag acaaatgaag cagtccatct gctctgagat  43020
attaagccct atattaagat tgtagaaact gtagcatttg ccacagctat aagcaccctg  43080
ggaatgtgtg gtcaggaaac tccctgttgc cccatagcag cccatgaatc cagctcactg  43140
aatgatgttc aggtctcctg ctccctgtca ttagtattgt cttaacctcc cagggcaatt  43200
tctgccatta ctactcagac atgtccctac cttgctacct ccagttctaa tgctaccata  43260
tatttggccc tggatctttg tcaactgaaa ataagacata gaatttttag ctgggtgcag  43320
tggctcatgc ctgtaatccc agcactttgg gattgctttg agcccaggag ttcgagacca  43380
gcctgggcaa catggcgaaa ccccatccct acaaaaacaa aaatgagtgg gctgtgtggc  43440
gcacacctta gtcccagcta ttcaggaggc tgagatggga ggatcacttg agcccaggga  43500
agtcgaggct gctgttagct gtgaccacgc cactgcactc caggctgggg aacaaaaaaa  43560
agacacaaaa ttttcataga accctgatag aacagaggct ttccctctta gtgtgaaaga  43620
agtgtaccat ttatcatgct tatccacagc caaattccta aagtgtcaag gtgcctttgt  43680
gtgtgtatgc agctccattt cttaattcat tatttatccc taccgcagtt gcctatgata  43740
tgctttgttt ttatggccct tatatagtat tacagtcata ctatagtcat ctgtatattt  43800
ccttttttgg tcatattttt attgtggtaa aatatacaaa acaaaattta ccgtcttaac  43860
cctccttaag tgtacagctt gtcagcatta aatacattca tatagttgca ccaccatcac  43920
cgccatccat ttccagaact tctctatcat ccctaaggga agctctggac ccactgaaca  43980
ataactgccc atcttccctc cccacactcc cctagcccct agtaacctct aatctacttt  44040
ctgtctccat gaattggcct attctaggta cctcatataa gtggaatcat acaaatttgt  44100
ctttccgtat ctggcttatg tcacttagca tattttcaag gttcatccat gttgtagaat  44160
gtgtcaaggg gctttaaatc ggcggggtgc agggggggtac tttattactt gctatcctgg  44220
atcctgctgc ttgtcttctg gctaaaataa aatgtacttt gtgaaattaa gacattttat  44280
agagattaat tactgacatt aaattttctt ctagaaacat gggggctatt atgaaggaac  44340
atgggaaaaa ctgggaagca ttcacaactg aaaaaaaaaa atccaagcca aaagactttt  44400
tctaaaaact ttcttgcaag acagagcaat gctatcttca cattatgtta ttgggtgcta  44460
taacatcatc taagctggag acagcctact gtcatagctt tggagtccaa agacctgggt  44520
ttgaattcta accattttct agctaaatga acatgggcaa gttatgtagt ccctctgaac  44580
tttcgtttcc ttgtctgtaa aatggcaaca atgataataa ggactttcta attctttatt  44640
gagaattcca taaaaacaaa tgcataacaa gctccatgca ccataaatgc tcaatagatg  44700
cttgctttct tcctgtccca tacaaattgt tgtacagatg tttcaataac ctaactgcta  44760
```

-continued

```
gcaagtatta cctgaaattt aacccgattg ttctcttctt tcacttagca gtattatttc  44820
ttgtccacaa tagaggaagc acaattgcag ttctgatgct gcaatgacct tttatacatt  44880
tgaagagttt ttcctggtca tttaatcagg aaacaacact tactcaccat atatgaggcg  44940
agtaactcta caagactcta caaggtcttg taagaagcta taagccaagg gggaaaaaaa  45000
aaagaagaat aagaaaaaca catgatctgt attttcaagt gttgttcagt ctaggtaggg  45060
cgatgggtga agtatacgta aatatatgtg aaacaaacat aaactatgta tatatgtaaa  45120
aggatgtatg tatagatagt taatataaat tgtaatactg aaataagatg tgctattagg  45180
atacttgaag agtagtttat ttgaaaagaa tataagtata tccttgtgtg ccattagtat  45240
ttgaagagtt gtatataaac tgattttttt tctttttcct ttttttgag aaggagtctt  45300
gctctgtcac ccaggctgga gtgcagtggt gccatctcgg ctcactgcaa gctccacctc  45360
cccagttcaa gcgattctcc tgcctcagcc tcctgactag ctggaattac aggtgcccgc  45420
caccacacct ggctaacttt tgtattttta gtagagacgg ggtttcacca tgttggtcag  45480
gctggtctca aactcctgac ctcgtgatcc acccgctttg gcctcccaaa gtggtgggat  45540
tacaggcgtg agccaccgcg cccagcctca taaactgatt tttaaaatac aatatacagt  45600
taggcatagt tgtgtgtgcc tatagtccct actgcttggg aggctgaggc aggaggatcc  45660
tttgatccca ggagtttggg caacatagtg agacccccat ctctaataat aataaatata  45720
aatttcaaat aacattttaa aatatgacat actatctttg aatgaccaca caatttaaaa  45780
agcaatcatt ttacggttct ttagtgttca gttagcacag cacttagaaa tcatagaata  45840
aagtgagcaa gatgcttctc aaagcctgat cactctttag gactcacaat gggctaggta  45900
ctatgctgga aagagaaaaa ataataattt tctaacctgc ttgagacata gtggtataaa  45960
tgataacaca gctgctgaac gtgatgactt tctcactttg tccgcagagc aagaaactat  46020
agatgcagta acaaaactgc attcaatgaa catgggactg tagataacaa actaacttca  46080
tttctttggg tacatgccct gtattgggat tgctggatca tatggtagtt ccatttttaa  46140
tattttgagg aacctccata ccatcttcca taatggctgt gctatttgca tgcccaccat  46200
cagtgtgcaa atgctccctt tcctccacat tcttgccaac acctctttca tctttttgat  46260
aatagttatg aggcaatatc tcaccatggt cctagacttc atttgtctga tgactaatga  46320
tattgagcat tttttcatat atctcttggc catttgtagg tcatcttttg agaaatgtgt  46380
attgaggttc ttagtccatt cctgctacca taacaaaatc ccttagagtg ggcattttat  46440
aaagaacaga attggcccgg ggcgcagtgg ctcatgcctg taatcccagc actttgggag  46500
gccaaggtgg gtggatcacc tgaggtcagg agttcaagac cagcctggtc aatatggtga  46560
aaccccatct ctactaaaaa tacaaaaact agccgaacgt ggtggtgtgc acctgtagtc  46620
ccagctactt gggaggctga gacaggagaa ttgcttgaac ccaggaggag gaggttgcag  46680
tgagacgaga tcgtgccact gcactccagc ctgagcaaca gagtgagact tcatctcaaa  46740
aaaaaaaaaa aaaaaaaaaa aaagaacaga aatttatttc tcactgttct agaggctgga  46800
aagtccaaga tcaaggcact gtaggctgtt gtccagtgag tatatttggt ctccaagtta  46860
gtgccttgtc gctgcatcct ccagataggg caaatgctgt gtccttacat ggtggaaggg  46920
tagaagagca aacgggcctg actgattccc tctagctcct ttataagggc attcatctct  46980
gtccttgtgt cctaatcaca cgctaaaggt ggctaaaggc cccacctctt aatactgttg  47040
cattggggat aaagtttcaa catgaattat gaagagaata caaacattta aaccacaaca  47100
```

-continued

```
agtcctttgc ccactttttt tttggagacc gagtctcact ctgttgccca ggctggaatg  47160
cagtggcttg atcctggctc attgcaacct ccacctcctg ggttcaagca attctcctgc  47220
ctcagcttcc caagtagctg ggattacagg tgtgcactac cacacccagc taattttgta  47280
tatttagtag agacagggtt ttaccatgtt agccaggctg atctcgaact ctcgacttct  47340
ggtgatccac ctgcctcagc ctcccaaagt gctgagatta caggcgtgag ccaccgtgcc  47400
cggccctttg cccactgttt aatggggttg tcttcttgct attgagttcc ttatatattt  47460
tttatattaa ccccttatca aatgtatggc ttgcaaatat tttctcccat cgtaggttgt  47520
ctcttcactc taatgattgt ttcctttgct ctgaagacac tttttagttt tatttattcc  47580
catttgtcta ttttcacatt tgttgcctat aagcaggtta gaaaattata cagattataa  47640
atagttcctg aatttgtgtt ttactaaacg tagcctacac agatgaaaac aggaaagcta  47700
cacttcagaa tctgtgatat ttgatgtcag aagtgcatcc ctgaaagcaa tgggtccatt  47760
ctaaatctcc taacctctaa ccataatttg ttctatattt atcctgagat ctcactctta  47820
ggaataaaaa cacattgaga agtcctgagt ctctatttta ctatttttct gaagtgcctg  47880
tagtgtgtgt gtttacatct aaataatagc tgtcaccact ttctgatcaa ttttaaaaac  47940
taattttaaa taagtgtttt tcataaataa tcctggattt agttctaaaa tcagaataaa  48000
ctatgcaaac tttgaatcca ttaatcaaaa tgcttttagt ttccattcca acaaaggcag  48060
ataaacagcc ccttcagacc actgtggttt gaaacatagc actcactggc tgccttttaa  48120
gagccttcag ggagggagca aaacaacaat ttttggtttt cagtttccca gacagtgaag  48180
gagagattta gtaattttct caagtgaaaa agaattcaat aacttgcaaa tagaaactga  48240
gatcaaattt ccaaataaag tatattgaat ttttgtttaa acttttaaaa tctcaagctt  48300
aaagctttga acataagatt aaaaaaactt tttttagtat ccatttttgtt ggctttagtt  48360
aaatatcata caaagtaacc aaccatctgg taactttcac cttagagaaa acatgatagt  48420
ggttgtcacc tatttcttct attgttttct cttcattatc tttgctttct tttcactgca  48480
ctttgccagc caacagagga tgtatgggta catgtgactc acacccactt gtttacacat  48540
gcatctgtgc aaatacataa gatggtaggt taaaaaaaga agaattagtt tcttgtcccc  48600
tggccttctc ccacaaaaga agaattagtc cagttggttt ttcaaaatgg attccaggat  48660
tcttagtgtt ccctcgggct cagggtggtt gataggaaaa gcctataatc ctctcagtca  48720
cttttcagtt tgtttaggga atggatcaaa gaaggaagat tttactgggt ggcatgattt  48780
ttttattata tgagggaaaa tagcacttca ctgtcttttg tttaaagaca agcttaacag  48840
atgctaaaaa gtacatctct cagccagatt cctagtcaac aagctgatag acactaagat  48900
tctggattct tcattgatta tattcagtca ttgttgggca attgactccc tgccataata  48960
attgggccag tatctataac cagcatttta cagatggatt cgctagactc tttctgtaag  49020
agatgtttct aaaaagagtt atagtgagat atgcttctaa gaaaagttat actgtagtag  49080
tgtaatgaaa gctactagtg ttttattagt atttcacaag aacaatgtta ctctgtctcc  49140
catatataac tgtctatggg cttttatgat tattctttaa aaaaaaaaaa tactaaggta  49200
atgcctaccg gggaactcat ggtgctggct tcatccaaag tctgagctgt tttggcttta  49260
tactccgaaa gactttattt tcatacatct taactaaaaa ctggggcttt aaattggtca  49320
ttcaaggcca ggcgcggttg ctcatgcctg aaatcccagc actttgggag gccgaggtgg  49380
gcagatcacg aggtcaggag attgagacca tcctggccaa cacggtgaaa ccccgtctct  49440
actaaaaata caacaacaac aacaacaaaa atagccaggc gtggtggctt gcatctgtaa  49500
```

-continued

```
tcccagctac tcaggaggct gaggcaggag aatggtgtga acctgggagg cagagcttgc  49560
agtgagccga gatcgcatca ctgcactcca gcctgggcga cagagcgaga ctccgtctca  49620
aaaaaaaaaa acatcggtaa ttcaaagcat agaccagccc tttttcaagt gatgttgttc  49680
ccatgacaat ccatcagtga aaaaccaaat accatattcc aagctgctag tcacagagaa  49740
aacaagcaga tgagatgaat gtaatagaaa agactagagt tagttttggg gtcatcttta  49800
gccaacattc cattgcctga agctcagtaa tctgaatcct ttttaatttg agcacatcag  49860
ggaacagctg aatacccatg ctgaggcata atttaagctg tcaagtgtct cctgtcaata  49920
tacatgtggt catctgatgc aaggcaaaga gacagtcact cctgcttctt tatatcccta  49980
gctcccaaca tggtgtccta atgcatgata atcatgcagt aaatgttcag tgatgagaac  50040
atgactttga gcaaggctgt atgatctgcc tcagaacaag tgagtcagta agaatgcagg  50100
ccccggacca taggaatgta ttacagtttt gcccaagaaa ccacaaacgt tggaaacact  50160
caagtttctt tctcgtatac atcagctggt gtcatgcaat gggacatacc atctgacgct  50220
tccctgttct tccctgattt gtcctgcatg tctccaatac ctctttccaa ccacctcatc  50280
tccccacctc acctttcttt ttctttgttt ggctttatat aggtgctggg agtccctaca  50340
gaggatactt ggccgggagt ctccaagcta cctaactaca atccaggtaa tattgatctg  50400
agcttctgaa tactctgaga attagtaatg taaggagagc attggccacg ctaacagggc  50460
gttcttgtat tgtgaactca gcggcaaaga tgggtgtaga ggaatttcta cattcatata  50520
ttccctgact aatctttgta tgaggaagac actgaaagag tagctgaggt tagaccagtt  50580
ccccagctct gtaaaacaca agtagcaagc tgaatagaat ttgaaatgac tattactgtg  50640
gattccacat ccattgtcaa atacccaatg gctcaaaaga acaactcaaa agatgggctc  50700
acttttgggc cccctgactg tcataagtgt attgattagt attgaattgc atatgtataa  50760
aaagaaagct aatgcaacag aacagaggta gaggctcgct aggcctagga catgccaagt  50820
aagctgtctg taggttatac ttactaagag ttcattcatt gcctgtaaac ctgacacttg  50880
gtcattgtct ctcacacatt tcatctttca agactggctt ctgggatcga tttagaagtg  50940
ctggaagtgt tatccatggg ggaattcttt gagaagctgt cgcagggcca catcagaggg  51000
atcagattaa gcagtagtca cttcaaggat gttgagacag aggggaggag acaggcactg  51060
aactacagga tgaaggatca tattagaagc tgaagaagca aataaagccc atgccaaagc  51120
tgagctctca ctggcagggt tgaaggggag gtagaaaggt acagataacg acaagattag  51180
ggtggatatg ctccaagcca gatttttcta gtctttatgg tcttacattg ttccattact  51240
aaaaatgaaa tcttcccaaa ttgttgtcct tacttttttt tttttttttt tgagatggag  51300
ttttgctctt atcgcccagg ctggagtgca gtggcacgat ctcggctcac tgcaacctcc  51360
acctcctggg ttcaagcaat tctcctgcct cagcctcccc aagtagctgg gactacaggc  51420
acccgccacc atgcccagct aattttttgt atttttagta gagatgaggt ttcaccatgt  51480
tggccaggct ggtctcgaac tcctgacctc aggtgatcca cttgcttcag cttcccaaaa  51540
tgctgggatt acaggcatga gccagcgcgc ctggcctgtt gtccttacta actttggtat  51600
gagattatcc tggaagggtt tcctgagagc aagaaattgt aggtagagtt aaaatgtgat  51660
taaagaagag aataaaatac atagggagct ggggactctt tttcttattt tctttagcat  51720
ccaatacttt tgcttacagc tatccatagg gatctggcat cttgaaccac caggattatg  51780
gaagccctac agcaagctaa agactaactg taaagtcctt tcagctgctt tgtgaatggt  51840
```

-continued

```
tatatctatt gctaaaaggc cttaatatca tttgcaaata gtttatgatt tctaactatt  51900

tttctagagt ttaacacgtg agaaaaatgc tactctctgg tcacaggact tagaatagtg  51960

cctatttcca ttggtctgag atagagaaaa aagaacaagt ttcttgtgga gccgtggtcc  52020

agtctgcaaa ttgctcctat ctccagttgc catggtttcc aggagaacgt ggctctcatc  52080

ttttcctgcc ctgcctgtac ttctccctgt ccactctgtt ctctattttc cctcagcttc  52140

ctaactgagg atgccagcag aagtttagag tcacagatgg attgtaggaa acaatttgga  52200

tgatgccaat acaaagctac tgtggtgggc atatgctgct cccccaaact tcagacattt  52260

gggtttcagg ttggtccagg caatcaacag tgatccttaa tacaaaatgt cttggtgaga  52320

gcaataatca agaaacttgg ccaaagtgct tccctgccag attgtgtgct taataagata  52380

actgggttcc aataaaacag agaaaatatg ttacatttta aaaaattttc tgttgtttca  52440

aaacaatgtg cagtttttct atataagaag aaaagtctcc aggcccaaca tccatagggc  52500

tcatcatcca ttgtttttct tttaagtttt caatttaatc caaataagtc aaaaattttc  52560

aggtacctac tatctgccag gtgctgtgcc gtgcgctggg gctacacaga tggagagggt  52620

gcattcttgg atctctagtg tttgggtttg gattcattca cccacactct ttcaccagtt  52680

ctctttgtta ctggggtgct catttgtgag ccctgcttcc atggcttgga gagtttgtgg  52740

ctgtgggcca ggctgagctt atggagcaaa gggagttgga accttagcca tagacatgat  52800

gtctaaacct ggatttggaa atcttaaaag tccagcctat cttgggccat ggggtcagta  52860

ttattgataa ctcaatccca aggactgtgt tttaaaaggg tctccaacat ctgcatttca  52920

ggaacatcct cttacgtgag tcaataagtt ccttttgagc cacccctac ccatccccat  52980

ccctgagctg ctgtggcttc taaacacttg aatgtcagtg attaagggga gcagaagaca  53040

agctgggagc caggaaagtg tcacagatga gcaccgtgtc agcagcattc tggatgagct  53100

tcccattcct ttccttttca ttctaagtag tcctaggagc cccaaactt tgaatcagcc  53160

agtacaattt tgagggagtc cagttgtccg gaacttggga gaaccatcca gtgtccatct  53220

acacccatgc ctccatttct aggccttatc tggacacctc taggaggaca gcaaagtttc  53280

catttgtaca gcttttaaaa agtcacctga tgctgaccca gtcggatttc tc          53332
```

<210> SEQ ID NO 4
<211> LENGTH: 1308
<212> TYPE: DNA
<213> ORGANISM: Human

<400> SEQUENCE: 4

```
atgggtcaag agctgtgtgc aaagactgta cagcctggat gcagctgcta ccattgttca     60

gagggaggcg aggcacacag ctgtcggagg agtcagcctg agaccacgga ggctgcgttc    120

aagctaacag acctaaaaga agcatcatgt tccatgactt catttcaccc caggggactt    180

caagctgccc gtgcccagaa gttcaagagt aaaaggccac ggagtaacag tgattgtttt    240

caggaagagg atctgaggca gggttttcag tggaggaaga gcctcccttt tggggcagcc    300

tcatcttact tgaacttgga gaagctgggt gaaggctctt atgcgacagt ttacaagggg    360

attagcagaa taaatggaca actagtggct ttaaaagtca tcagcatgaa tgcagaggaa    420

ggagtcccat ttacagctat ccgagaagct tctctcctga agggtttgaa acatgccaat    480

attgtgctcc tgcatgacat aatccacacc aaagagacac tgacattcgt tttgaatac    540

atgcacacag acctggccca gtatatgtct cagcatccag gagggcttca tcctcataat    600

gtcagacttt tcatgtttca acttttgcgg ggcctggcgt acatccacca ccaacacgtt    660
```

```
cttcacaggg acctgaaacc tcagaactta ctcatcagtc acctgggaga gctcaaactg    720

gctgattttg gtcttgcccg ggccaagtcc attcccagcc agacatactc ttcagaagtc    780

gtgaccctct ggtaccggcc ccctgatgct ttgctgggag ccactgaata ttcctctgag    840

ctggacatat ggggtgcagg ctgcatcttt attgaaatgt tccagggtca acctttgttt    900

cctggggttt ccaacatcct tgaacagctg gagaaaatct gggaggtgct gggagtccct    960

acagaggata cttggccggg agtctccaag ctacctaact acaatccaga atggttccca   1020

ctgcctacgc ctcgaagcct tcatgttgtc tggaacaggc tgggcagggt tcctgaagct   1080

gaagacctgg cctcccagat gctaaaaggc tttcccagag accgcgtctc cgcccaggaa   1140

gcacttgttc atgattattt cagcgccctg ccatctcagc tgtaccagct tcctgatgag   1200

gagtctttgt ttacagtttc aggagtgagg ctaaagccag aaatgtgtga ccttttggcc   1260

tcctaccaga aaggtcacca cccagcccag tttagcaaat gctggtga                1308
```

<210> SEQ ID NO 5
<211> LENGTH: 435
<212> TYPE: PRT
<213> ORGANISM: Homo sapiens

<400> SEQUENCE: 5

```
Met Gly Gln Glu Leu Cys Ala Lys Thr Val Gln Pro Gly Cys Ser Cys
 1               5                  10                  15

Tyr His Cys Ser Glu Gly Gly Glu Ala His Ser Cys Arg Arg Ser Gln
            20                  25                  30

Pro Glu Thr Thr Glu Ala Ala Phe Lys Leu Thr Asp Leu Lys Glu Ala
        35                  40                  45

Ser Cys Ser Met Thr Ser Phe His Pro Arg Gly Leu Gln Ala Ala Arg
    50                  55                  60

Ala Gln Lys Phe Lys Ser Lys Arg Pro Arg Ser Asn Ser Asp Cys Phe
65                  70                  75                  80

Gln Glu Glu Asp Leu Arg Gln Gly Phe Gln Trp Arg Lys Ser Leu Pro
                85                  90                  95

Phe Gly Ala Ala Ser Ser Tyr Leu Asn Leu Glu Lys Leu Gly Glu Gly
            100                 105                 110

Ser Tyr Ala Thr Val Tyr Lys Gly Ile Ser Arg Ile Asn Gly Gln Leu
        115                 120                 125

Val Ala Leu Lys Val Ile Ser Met Asn Ala Glu Glu Gly Val Pro Phe
    130                 135                 140

Thr Ala Ile Arg Glu Ala Ser Leu Leu Lys Gly Leu Lys His Ala Asn
145                 150                 155                 160

Ile Val Leu Leu His Asp Ile Ile His Thr Lys Glu Thr Leu Thr Phe
                165                 170                 175

Val Phe Glu Tyr Met His Thr Asp Leu Ala Gln Tyr Met Ser Gln His
            180                 185                 190

Pro Gly Gly Leu His Pro His Asn Val Arg Leu Phe Met Phe Gln Leu
        195                 200                 205

Leu Arg Gly Leu Ala Tyr Ile His His Gln His Val Leu His Arg Asp
    210                 215                 220

Leu Lys Pro Gln Asn Leu Leu Ile Ser His Leu Gly Glu Leu Lys Leu
225                 230                 235                 240

Ala Asp Phe Gly Leu Ala Arg Ala Lys Ser Ile Pro Ser Gln Thr Tyr
                245                 250                 255
```

-continued

```
Ser Ser Glu Val Val Thr Leu Trp Tyr Arg Pro Pro Asp Ala Leu Leu
            260                 265                 270

Gly Ala Thr Glu Tyr Ser Ser Glu Leu Asp Ile Trp Gly Ala Gly Cys
        275                 280                 285

Ile Phe Ile Glu Met Phe Gln Gly Gln Pro Leu Phe Pro Gly Val Ser
    290                 295                 300

Asn Ile Leu Glu Gln Leu Glu Lys Ile Trp Glu Val Leu Gly Val Pro
305                 310                 315                 320

Thr Glu Asp Thr Trp Pro Gly Val Ser Lys Leu Pro Asn Tyr Asn Pro
                325                 330                 335

Glu Trp Phe Pro Leu Pro Thr Pro Arg Ser Leu His Val Val Trp Asn
            340                 345                 350

Arg Leu Gly Arg Val Pro Glu Ala Glu Asp Leu Ala Ser Gln Met Leu
        355                 360                 365

Lys Gly Phe Pro Arg Asp Arg Val Ser Ala Gln Glu Ala Leu Val His
    370                 375                 380

Asp Tyr Phe Ser Ala Leu Pro Ser Gln Leu Tyr Gln Leu Pro Asp Glu
385                 390                 395                 400

Glu Ser Leu Phe Thr Val Ser Gly Val Arg Leu Lys Pro Glu Met Cys
                405                 410                 415

Asp Leu Leu Ala Ser Tyr Gln Lys Gly His His Pro Ala Gln Phe Ser
            420                 425                 430

Lys Cys Trp
        435


<210> SEQ ID NO 6
<211> LENGTH: 240
<212> TYPE: PRT
<213> ORGANISM: Mus musculus

<400> SEQUENCE: 6

Phe Gly Lys Ala Asp Ser Tyr Glu Lys Leu Glu Lys Leu Gly Glu Gly
 1               5                  10                  15

Ser Tyr Ala Thr Val Tyr Lys Gly Lys Ser Lys Val Asn Gly Lys Leu
            20                  25                  30

Val Ala Leu Lys Val Ile Arg Leu Gln Glu Glu Glu Gly Thr Pro Phe
        35                  40                  45

Thr Ala Ile Arg Glu Ala Ser Leu Leu Lys Gly Leu Lys His Ala Asn
    50                  55                  60

Ile Val Leu Leu His Asp Ile Ile His Thr Lys Glu Thr Leu Thr Leu
65                  70                  75                  80

Val Phe Glu Tyr Val His Thr Asp Leu Cys Gln Tyr Met Glu Gln His
                85                  90                  95

Pro Gly Gly Leu His Pro Asp Asn Val Lys Leu Phe Leu Phe Gln Leu
            100                 105                 110

Leu Arg Gly Leu Ser Tyr Ile His Gln Arg Tyr Ile Leu His Arg Asp
        115                 120                 125

Leu Lys Pro Gln Asn Leu Leu Ile Ser Asp Thr Gly Glu Leu Lys Leu
    130                 135                 140

Ala Asp Phe Gly Leu Ala Arg Ala Lys Ser Val Pro Ser His Thr Tyr
145                 150                 155                 160

Ser Asn Glu Val Val Thr Leu Trp Tyr Arg Pro Pro Asp Val Leu Leu
                165                 170                 175

Gly Ser Thr Glu Tyr Ser Thr Cys Leu Asp Met Trp Gly Val Gly Cys
            180                 185                 190
```

-continued

```
Ile Phe Val Glu Met Ile Gln Gly Val Ala Ala Phe Pro Gly Met Lys
        195                 200                 205

Asp Ile Gln Asp Gln Leu Glu Arg Ile Phe Leu Val Leu Gly Thr Pro
    210                 215                 220

Asn Glu Asp Thr Trp Pro Gly Val His Ser Leu Pro His Phe Lys Pro
225                 230                 235                 240


<210> SEQ ID NO 7
<211> LENGTH: 245
<212> TYPE: PRT
<213> ORGANISM: Homo sapiens

<400> SEQUENCE: 7

Phe Gly Lys Ala Asp Ser Tyr Glu Lys Leu Glu Lys Leu Gly Glu Gly
 1               5                  10                  15

Ser Tyr Ala Thr Val Tyr Lys Gly Lys Ser Lys Val Asn Gly Lys Leu
            20                  25                  30

Val Ala Leu Lys Val Ile Arg Leu Gln Glu Glu Glu Gly Thr Pro Phe
        35                  40                  45

Thr Ala Ile Arg Glu Ala Ser Leu Leu Lys Gly Leu Lys His Ala Asn
    50                  55                  60

Ile Val Leu Leu His Asp Ile Ile His Thr Lys Glu Thr Leu Thr Leu
65                  70                  75                  80

Val Phe Glu Tyr Val His Thr Asp Leu Cys Gln Tyr Met Asp Lys His
                85                  90                  95

Pro Gly Gly Leu His Pro Asp Asn Val Lys Leu Phe Leu Phe Gln Leu
            100                 105                 110

Leu Arg Gly Leu Ser Tyr Ile His Gln Arg Tyr Ile Leu His Arg Asp
        115                 120                 125

Leu Lys Pro Gln Asn Leu Leu Ile Ser Asp Thr Gly Glu Leu Lys Leu
    130                 135                 140

Ala Asp Phe Gly Leu Ala Arg Ala Lys Ser Val Pro Ser His Thr Tyr
145                 150                 155                 160

Ser Asn Glu Val Val Thr Leu Trp Tyr Arg Pro Pro Asp Val Leu Leu
                165                 170                 175

Gly Ser Thr Glu Tyr Ser Thr Cys Leu Asp Met Trp Gly Val Gly Cys
            180                 185                 190

Ile Phe Val Glu Met Ile Gln Gly Val Ala Ala Phe Pro Gly Met Lys
        195                 200                 205

Asp Ile Gln Asp Gln Leu Glu Arg Ile Phe Leu Val Leu Gly Thr Pro
    210                 215                 220

Asn Glu Asp Thr Trp Pro Gly Val His Ser Leu Pro His Phe Lys Pro
225                 230                 235                 240

Glu Arg Phe Thr Leu
                245


<210> SEQ ID NO 8
<211> LENGTH: 330
<212> TYPE: PRT
<213> ORGANISM: Mus musculus

<400> SEQUENCE: 8

Phe Gly Lys Ala Asp Ser Tyr Glu Lys Leu Glu Lys Leu Gly Glu Gly
 1               5                  10                  15

Ser Tyr Ala Thr Val Tyr Lys Gly Lys Ser Lys Val Asn Gly Lys Leu
            20                  25                  30
```

```
Val Ala Leu Lys Val Ile Arg Leu Gln Glu Glu Glu Gly Thr Pro Phe
        35                  40                  45

Thr Ala Ile Arg Glu Ala Ser Leu Leu Lys Gly Leu Lys His Ala Asn
    50                  55                  60

Ile Val Leu Leu His Asp Ile Ile His Thr Lys Glu Thr Leu Thr Leu
65                  70                  75                  80

Val Phe Glu Tyr Val His Thr Asp Leu Cys Gln Tyr Met Glu Gln His
                85                  90                  95

Pro Gly Gly Leu His Pro Asp Asn Val Lys Leu Phe Leu Phe Gln Leu
            100                 105                 110

Leu Arg Gly Leu Ser Tyr Ile His Gln Arg Tyr Ile Leu His Arg Asp
        115                 120                 125

Leu Lys Pro Gln Asn Leu Leu Ile Ser Asp Thr Gly Glu Leu Lys Leu
    130                 135                 140

Ala Asp Phe Gly Leu Ala Arg Ala Lys Ser Val Pro Ser His Thr Tyr
145                 150                 155                 160

Ser Asn Glu Val Val Thr Leu Trp Tyr Arg Pro Pro Asp Val Leu Leu
                165                 170                 175

Gly Ser Thr Glu Tyr Ser Thr Cys Leu Asp Met Trp Gly Val Gly Cys
            180                 185                 190

Ile Phe Val Glu Met Ile Gln Gly Val Ala Ala Phe Pro Gly Met Lys
        195                 200                 205

Asp Ile Gln Asp Gln Leu Glu Arg Ile Phe Leu Val Leu Gly Thr Pro
    210                 215                 220

Asn Glu Asp Thr Trp Pro Gly Val His Ser Leu Pro His Phe Lys Pro
225                 230                 235                 240

Glu Arg Phe Thr Val Tyr Ser Ser Lys Ser Leu Arg Gln Ala Trp Asn
                245                 250                 255

Lys Leu Ser Tyr Val Asn His Ala Glu Asp Leu Ala Ser Lys Leu Leu
            260                 265                 270

Gln Cys Ser Pro Lys Asn Arg Leu Ser Ala Gln Ala Ala Leu Ser His
        275                 280                 285

Glu Tyr Phe Ser Asp Leu Pro Pro Arg Leu Trp Glu Leu Thr Asp Met
    290                 295                 300

Ser Ser Ile Phe Thr Val Pro Asn Val Arg Leu Gln Pro Glu Ala Gly
305                 310                 315                 320

Glu Ser Met Arg Ala Phe Gly Lys Asn Asn
                325                 330


<210> SEQ ID NO 9
<211> LENGTH: 330
<212> TYPE: PRT
<213> ORGANISM: Homo sapiens

<400> SEQUENCE: 9

Phe Gly Lys Ala Asp Ser Tyr Glu Lys Leu Glu Lys Leu Gly Glu Gly
 1               5                  10                  15

Ser Tyr Ala Thr Val Tyr Lys Gly Lys Ser Lys Val Asn Gly Lys Leu
            20                  25                  30

Val Ala Leu Lys Val Ile Arg Leu Gln Glu Glu Glu Gly Thr Pro Phe
        35                  40                  45

Thr Ala Ile Arg Glu Ala Ser Leu Leu Lys Gly Leu Lys His Ala Asn
    50                  55                  60

Ile Val Leu Leu His Asp Ile Ile His Thr Lys Glu Thr Leu Thr Leu
```

-continued

```
65                  70                  75                  80

Val Phe Glu Tyr Val His Thr Asp Leu Cys Gln Tyr Met Asp Lys His
                85                  90                  95

Pro Gly Gly Leu His Pro Asp Asn Val Lys Leu Phe Leu Phe Gln Leu
            100                 105                 110

Leu Arg Gly Leu Ser Tyr Ile His Gln Arg Tyr Ile Leu His Arg Asp
        115                 120                 125

Leu Lys Pro Gln Asn Leu Leu Ile Ser Asp Thr Gly Glu Leu Lys Leu
    130                 135                 140

Ala Asp Phe Gly Leu Ala Arg Ala Lys Ser Val Pro Ser His Thr Tyr
145                 150                 155                 160

Ser Asn Glu Val Val Thr Leu Trp Tyr Arg Pro Pro Asp Val Leu Leu
                165                 170                 175

Gly Ser Thr Glu Tyr Ser Thr Cys Leu Asp Met Trp Gly Val Gly Cys
            180                 185                 190

Ile Phe Val Glu Met Ile Gln Gly Val Ala Ala Phe Pro Gly Met Lys
        195                 200                 205

Asp Ile Gln Asp Gln Leu Glu Arg Ile Phe Leu Val Leu Gly Thr Pro
    210                 215                 220

Asn Glu Asp Thr Trp Pro Gly Val His Ser Leu Pro His Phe Lys Pro
225                 230                 235                 240

Glu Arg Phe Thr Leu Tyr Ser Ser Lys Asn Leu Arg Gln Ala Trp Asn
                245                 250                 255

Lys Leu Ser Tyr Val Asn His Ala Glu Asp Leu Ala Ser Lys Leu Leu
            260                 265                 270

Gln Cys Ser Pro Lys Asn Arg Leu Ser Ala Gln Ala Ala Leu Ser His
        275                 280                 285

Glu Tyr Phe Ser Asp Leu Pro Pro Arg Leu Trp Glu Leu Thr Asp Met
    290                 295                 300

Ser Ser Ile Phe Thr Val Pro Asn Val Arg Leu Gln Pro Glu Ala Gly
305                 310                 315                 320

Glu Ser Met Arg Ala Phe Gly Lys Asn Asn
                325                 330
```

<210> SEQ ID NO 10
<211> LENGTH: 330
<212> TYPE: PRT
<213> ORGANISM: Mus musculus

<400> SEQUENCE: 10

```
Phe Gly Lys Ala Asp Ser Tyr Glu Lys Leu Glu Lys Leu Gly Glu Gly
 1               5                  10                  15

Ser Tyr Ala Thr Val Tyr Lys Gly Lys Ser Lys Val Asn Gly Lys Leu
            20                  25                  30

Val Ala Leu Lys Val Ile Arg Leu Gln Glu Glu Glu Gly Thr Pro Phe
        35                  40                  45

Thr Ala Ile Arg Glu Ala Ser Leu Leu Lys Gly Leu Lys His Ala Asn
    50                  55                  60

Ile Val Leu Leu His Asp Ile Ile His Thr Lys Glu Thr Leu Thr Leu
65                  70                  75                  80

Val Phe Glu Tyr Val His Thr Asp Leu Cys Gln Tyr Met Asp Lys His
                85                  90                  95

Pro Gly Gly Leu His Pro Asp Asn Val Lys Leu Phe Leu Phe Gln Leu
            100                 105                 110
```

-continued

```
Leu Arg Gly Leu Ser Tyr Ile His Gln Arg Tyr Ile Leu His Arg Asp
        115                 120                 125

Leu Lys Pro Gln Asn Leu Leu Ile Ser Asp Thr Gly Glu Leu Lys Leu
    130                 135                 140

Ala Asp Phe Gly Leu Ala Arg Ala Lys Ser Val Pro Ser His Thr Tyr
145                 150                 155                 160

Ser Asn Glu Val Val Thr Leu Trp Tyr Arg Pro Pro Asp Val Leu Leu
                165                 170                 175

Gly Ser Thr Glu Tyr Ser Thr Cys Leu Asp Met Trp Gly Val Gly Cys
            180                 185                 190

Ile Phe Val Glu Met Ile Gln Gly Val Ala Ala Phe Pro Gly Met Lys
        195                 200                 205

Asp Ile Gln Asp Gln Leu Glu Arg Ile Phe Leu Val Leu Gly Thr Pro
    210                 215                 220

Asn Glu Asp Thr Trp Pro Gly Val His Ser Leu Pro His Phe Lys Pro
225                 230                 235                 240

Glu Arg Phe Thr Val Tyr Asn Ser Lys Ser Leu Arg Gln Ala Trp Asn
                245                 250                 255

Lys Leu Ser Tyr Val Asn His Ala Glu Asp Leu Ala Ser Lys Leu Leu
            260                 265                 270

Gln Cys Ser Pro Lys Asn Arg Leu Ser Ala Gln Ala Ala Leu Ser His
        275                 280                 285

Glu Tyr Phe Ser Asp Leu Pro Pro Arg Leu Trp Glu Leu Thr Asp Met
    290                 295                 300

Ser Ser Ile Phe Thr Val Pro Asn Val Arg Leu Gln Pro Glu Ala Gly
305                 310                 315                 320

Glu Ser Met Arg Ala Phe Gly Lys Asn Asn
                325                 330
```

ISOLATED HUMAN KINASE PROTEINS

RELATED APPLICATIONS

The present application is a divisional of U.S. application Ser. No. 09/801,861, filed on Mar. 9, 2001 and issued on Dec. 10, 2002 as U.S. Pat. No. 6,492,154, which claims benefit of U.S. Provisional Application No. 60/265,151, filed on Jan. 31, 2001.

FIELD OF THE INVENTION

The present invention is in the field of kinase proteins that are related to the Pftaire kinase subfamily, recombinant DNA molecules, and protein production. The present invention specifically provides novel peptides and proteins, representing two alternative splice forms, that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem*. 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 2 71:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

Pftaire Protein Kinases

The novel human proteins, and encoding gene, provided by the present invention are related to Pftaire serine/threonine kinases. Specifically, two alternative splice forms of the same gene are provided by the present invention, referred to herein as "splice form 1" and "splice form 2". The sequences of a cDNA molecule encoding splice form 1 and a transcript sequence encoding splice form 2 are provided in FIG. 1. The amino acid sequences of each splice form are provided in FIG. 2; splice form 1 is 343 amino acids in length and splice form 2 is 435 amino acids in length.

The proteins of the present invention are similar to Pftaire-1 previously isolated from the mouse (Besset et al., *Mol Reprod Dev* 1998 May;50(1):18–29 and Lazzaro et al., *J Neurochem* 1997 July;69(1):348–64) and human (Nagase et al., *DNA Res* Dec. 31, 1998; 5(6):355–64). Pftaire kinases are related to Cdk and cdc2 kinases, which are expressed in the brain and other mitotic tissues; however, Pftaire expression patterns in the nervous system differ from those of Cdk and cdc2 kinases and Pftaire kinases are likely to have distinct functions (Lazzaro et al., *J Neurochem* 1997 July;69(1):348–64).

Mouse Pftaire-1 shares 50% and 49% amino acid identity with Cdk5 and Pctaire-3, respectively. Two transcripts, approximately 5.5 and 4.9 kb in size, have been detected. These transcripts are highly expressed in the brain, testis and embryo, and expressed at low levels in all other analyzed tissues in the mouse. Pftaire-1 is expressed in late pachytene spermatocytes in the testis and in post-mitotic neuronal cells in both the brain and embryo, suggesting that Pftaire-1 plays key roles in meiosis and neuron differentiation and/or function (Besset et al., *Mol Reprod Dev* 1998 May;50(1):18–29).

Pftaire is highly expressed in both postnatal and adult nervous tissue. Certain terminally differentiated neurons and neuroglia have been shown to express Pftaire mRNA and proteins. Pftaire proteins are found in the nucleus and cytoplasm of neuron cells. These expression patterns suggest that Pftaire kinases play key roles in regulating and maintaining the postmitotic and differentiated condition of nervous system cells (Lazzaro et al., *J Neurochem* 1997 July;69(1):348–64).

Kinase proteins, particularly members of the Pftaire kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the Pftaire kinase subfamily.

SUMMARY OF THE INVENTION

The present invention is based in part on the identification of amino acid sequences of human kinase peptides and proteins, representing two alternative splice forms, that are related to the Pftaire kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in uterus endometrium adenocarcinoma, testis, lung fibroblasts, kidney renal cell adenocarcinoma, and the brain.

DESCRIPTION OF THE FIGURE SHEETS

FIG. 1 provides the nucleotide sequences of a cDNA molecule (for splice form 1; SEQ ID NO:1) and a transcript sequence (for splice form 2; SEQ ID NO:4) that encode the kinase proteins of the present invention. In addition, structure and functional information is provided, such as ATG start, stop and tissue distribution, where available, that allows one to readily determine specific uses of the inventions based on these molecular sequences. Experimental data as provided in FIG. 1 indicates expression in humans in uterus endometrium adenocarcinoma, testis, lung fibroblasts, kidney renal cell adenocarcinoma, and the brain.

FIG. 2 provides the predicted amino acid sequence of splice form 1 (SEQ ID NO:2) and splice form 2 (SEQ ID NO:5) of the kinase of the present invention. In addition structure and functional information such as protein family, function, and modification sites is provided where available, allowing one to readily determine specific uses of the inventions based on this molecular sequence.

FIG. 3 provides genomic sequences that span the gene encoding the kinase proteins of the present invention. (SEQ ID NO:3) In addition structure and functional information, such as intron/exon structure, promoter location, etc., is provided where available, allowing one to readily determine specific uses of the inventions based on this molecular sequence. As illustrated in FIG. 3, SNPs were identified at 26 different nucleotide positions (SNPs were also identified at an additional 30 nucleotide positions 3' of the ORF, as provided in U.S. Ser. No. 60/265,151, filed Jan. 31, 2001).

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the Pftaire kinase subfamily. Utilizing these sequences, additional genomic sequences were assembled and transcript and/or cDNA sequences were isolated and characterized. Based on this analysis, the present invention provides amino acid sequences of human kinase peptides and proteins, representing two alternative splice forms (referred to herein as "splice form 1" and "splice form 2"), that are related to the Pftaire kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the Pftaire kinase subfamily and the expression pattern observed. Experimental data as provided in FIG. 1 indicates expression in humans in uterus endometrium adenocarcinoma, testis, lung fibroblasts, kidney renal cell adenocarcinoma, and the brain. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known Pftaire family or subfamily of kinase proteins.

Specific Embodiments

Peptide Molecules

The present invention provides nucleic acid sequences that encode protein molecules that have been identified as being members of the kinase family of proteins and are related to the Pftaire kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in uterus endometrium adenocarcinoma, testis, lung fibroblasts, kidney renal cell adenocarcinoma, and the brain. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NOS:2 and 5), for example, proteins encoded by the transcript/cDNA nucleic acid sequences shown in FIG. 1 (SEQ ID NOS:1 and 4) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 2 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 2 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 26 different nucleotide positions (SNPs were also identified at an additional 30 nucleotide positions 3' of the ORF, as provided in U.S. Ser. No. 60/265,151 filed Jan. 31, 2001). Some of these SNPs, which are located outside the ORF and in introns, may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate.or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain. A large percentage of pharmaceutical agents are being developed that modulate the activity of kinase proteins, particularly members of the Pftaire subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in uterus endometrium adenocarcinoma, testis, lung fibroblasts, kidney renal cell adenocarcinoma, and the brain. Such uses can readily be determined using the information provided herein, that which is known in the art, and routine experimentation.

The proteins of the present invention (including variants and fragments that may have been disclosed prior to the present invention) are useful for biological assays related to kinases that are related to members of the Pftaire subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in uterus endometrium adenocarcinoma, testis, lung fibroblasts, kidney renal cell adenocarcinoma, and the brain. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in uterus endometrium adenocarcinoma, testis, lung fibroblasts, kidney renal cell adenocarcinoma, and the brain. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in uterus endometrium adenocarcinoma, testis, lung fibroblasts, kidney renal cell adenocarcinoma, and the brain. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in uterus endometrium adenocarcinoma, testis, lung fibroblasts, kidney renal cell adenocarcinoma, and the brain. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in uterus endometrium adenocarcinoma, testis, lung fibroblasts, kidney renal cell adenocarcinoma, and the brain. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in uterus endometrium adenocarcinoma, testis, lung fibroblasts, kidney renal cell adenocarcinoma, and the brain. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in uterus endometrium adenocarcinoma, testis, lung fibroblasts, kidney renal cell adenocarcinoma, and the brain. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NOS:1 and 4, transcript sequence and SEQ ID NO:3, genomic sequence), or any nucleic acid molecule that encodes the protein provided in FIG. 2, SEQ ID NOS:2 and 5. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NOS:1 and 4, transcript sequence and SEQ ID NO:3, genomic sequence), or any nucleic acid molecule that encodes the protein provided in FIG. 2, SEQ ID NOS:2 and 5. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NOS:1 and 4, transcript sequence and SEQ ID NO:3, genomic sequence), or any nucleic acid molecule that encodes the protein provided in FIG. 2, SEQ ID NOS:2 and 5. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 2 (as indicated in FIG. 3), which is supported by multiple lines of evidence, such as STS and BAC map data.

FIG. 3 provides information on SNPs that have been found in the gene encoding the kinase protein of the present invention. SNPs were identified at 26 different nucleotide positions (SNPs were also identified at an additional 30 nucleotide positions 3' of the ORF, as provided in U.S. Ser. No. 60/265,151 filed Jan. 31, 2001). Some of these SNPs, which are located outside the ORF and in introns, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 26 different nucleotide positions (SNPs were also identified at an additional 30 nucleotide positions 3' of the ORF, as provided in U.S. Ser. No. 60/265,151, Attrny. Dkt. No. CL1098-PROV, filed Jan. 31, 2001).

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins:

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 2 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated.

Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in uterus endometrium adenocarcinoma, testis, lung fibroblasts, kidney renal cell adenocarcinoma, and the brain. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in uterus endometrium adenocarcinoma, testis, lung fibroblasts, kidney renal cell adenocarcinoma, and the brain.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 26 different nucleotide positions (SNPs were also identified at an additional 30 nucleotide positions 3' of the ORF, as provided in U.S. Ser. No. 60/265,151 filed Jan. 31, 2001). Some of these SNPs, which are located outside the ORF and in introns, may affect control/regulatory elements. The gene encoding the novel kinase protein of the present invention is located on a genome component that has been mapped to human chromosome 2 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)) This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr*. 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res*. 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 26 different nucleotide positions (SNPs were also identified at an additional 30 nucleotide positions 3' of the ORF, as provided in U.S. Ser. No. 60/265,151 filed Jan. 31, 2001). Some of these SNPs, which are located outside the ORF and in introns, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that the kinase proteins of the present invention are expressed in humans in uterus endometrium adenocarcinoma, testis, lung fibroblasts, and kidney renal cell adenocarcinoma, as indicated by virtual northern blot analysis. In addition, tissue-screening panels indicate expression in the brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS: 1, 3, and 4).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application W095/11995 (Chee et al.), Lockhart, D. J. et al (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 26 different nucleotide positions (SNPs were also identified at an additional 30 nucleotide positions 3' of the ORF, as provided in U.S. Ser. No. 60/265,151 filed Jan. 31, 2001). Some of these SNPs, which are located outside the ORF and in introns, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSecl (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing. recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *